United States Patent
Zoldhelyi et al.

(10) Patent No.: US 8,617,538 B2
(45) Date of Patent: Dec. 31, 2013

(54) MESODERMAL-LIKE CELL POPULATION FOR TREATING ISCHEMIA IN MAMMALS

(75) Inventors: Pierre Zoldhelyi, Houston, TX (US); James T. Willerson, Houston, TX (US); Qui Liu, Houston, TX (US); Zhi-Qiang Chen, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 391 days.

(21) Appl. No.: 12/891,406

(22) Filed: Sep. 27, 2010

(65) Prior Publication Data

US 2011/0104124 A1     May 5, 2011

Related U.S. Application Data

(60) Provisional application No. 61/246,349, filed on Sep. 28, 2009.

(51) Int. Cl.
  *A61K 35/28*    (2006.01)
  *C12N 5/0789*   (2010.01)

(52) U.S. Cl.
  USPC ........................................ 424/93.7; 435/325

(58) Field of Classification Search
  USPC ........................................ 424/93.7; 435/325
  See application file for complete search history.

(56) References Cited

PUBLICATIONS

Prengler et al. Sickle Cell Disease: Ischemia and Seizures. Ann Neurol 2005;58:290-302.*

* cited by examiner

*Primary Examiner* — Taeyoon Kim
(74) *Attorney, Agent, or Firm* — Conley Rose, P.C.

(57) ABSTRACT

Compositions containing an effective amount of mesodermal-like multipotent mammalian mononuclear cells that express both CD34 and M-cadherin cell surface markers are used for preventing, treating or reducing the severity of tissue ischemia or an ischemia associated disorder in a mammal. Such uses may include repopulating an in vivo site with new myocytes and/or vascularizing an ischemic or adjacent tissue. Detection of the level and/or distribution of $CD34^+$/M-cadherin$^+$ mesodermal-like precursor cells in a mammalian tissue sample is used to diagnose, among other things, whether transplantation of autologous $CD34^+$/M-cadherin$^+$ mesodermal-like precursor cells to an ischemic site is indicated.

11 Claims, 63 Drawing Sheets

Adult mesodermal-like progenitor cells

Adult mesodermal-like progenitor cells

Adult mesodermal-like progenitor cells

Adult mesodermal-like progenitor cells

A.

B.

Adult mesodermal-like progenitor cells

Adult mesodermal-like progenitor cells

Adult mesodermal-like progenitor cells

Adult mesodermal-like progenitor cells

GFP$^{+/+}$ cells

Adult mesodermal-like progenitor cells

CD34 bearing cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

CD 73

Adult mesodermal-like progenitor cells

CD 44

Adult mesodermal-like progenitor cells

Adult mesodermal-like progenitor cells

Adult mesodermal-like progenitor cells

Adult mesodermal-like progenitor cells 2.50±0.25%*

*Mean ± SEM, n=4

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells
Immunophenotyping of CD34+/M-cad+ BMCs

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Adult mesodermal-like progenitor cells

Figure 20 A-2
Adult mesodermal-like progenitor cells

|   | A | B | C | D | E | F | G | H |
|---|---|---|---|---|---|---|---|---|
| 1 | POS | POS | NEG | NEG | bFGF | CRG-2 | EGF | Flt-3 Ligand |
| 2 | POS | POS | NEG | NEG | bFGF | CRG-2 | EGF | Flt-3 Ligand |
| 3 | G-CSF | HGF | IGF-1 | IL-4 | IL-6 | IL-10 | LIX | MCP-1 |
| 4 | G-CSF | HGF | IGF-1 | IL-4 | IL-6 | IL-10 | LIX | MCP-1 |
| 5 | Osteopontin | Resistin | SCF | SDF-1 alpha | TIMP-2 | VEGF | VEGF-D | VEGF-R3 |
| 6 | Osteopontin | Resistin | SCF | SDF-1 alpha | TIMP-2 | VEGF | VEGF-D | VEGF-R3 |
| 7 | NEG | NEG | NEG | NEG | NEG | NEG | NEG | POS |
| 8 | NEG | NEG | NEG | NEG | NEG | NEG | NEG | POS |

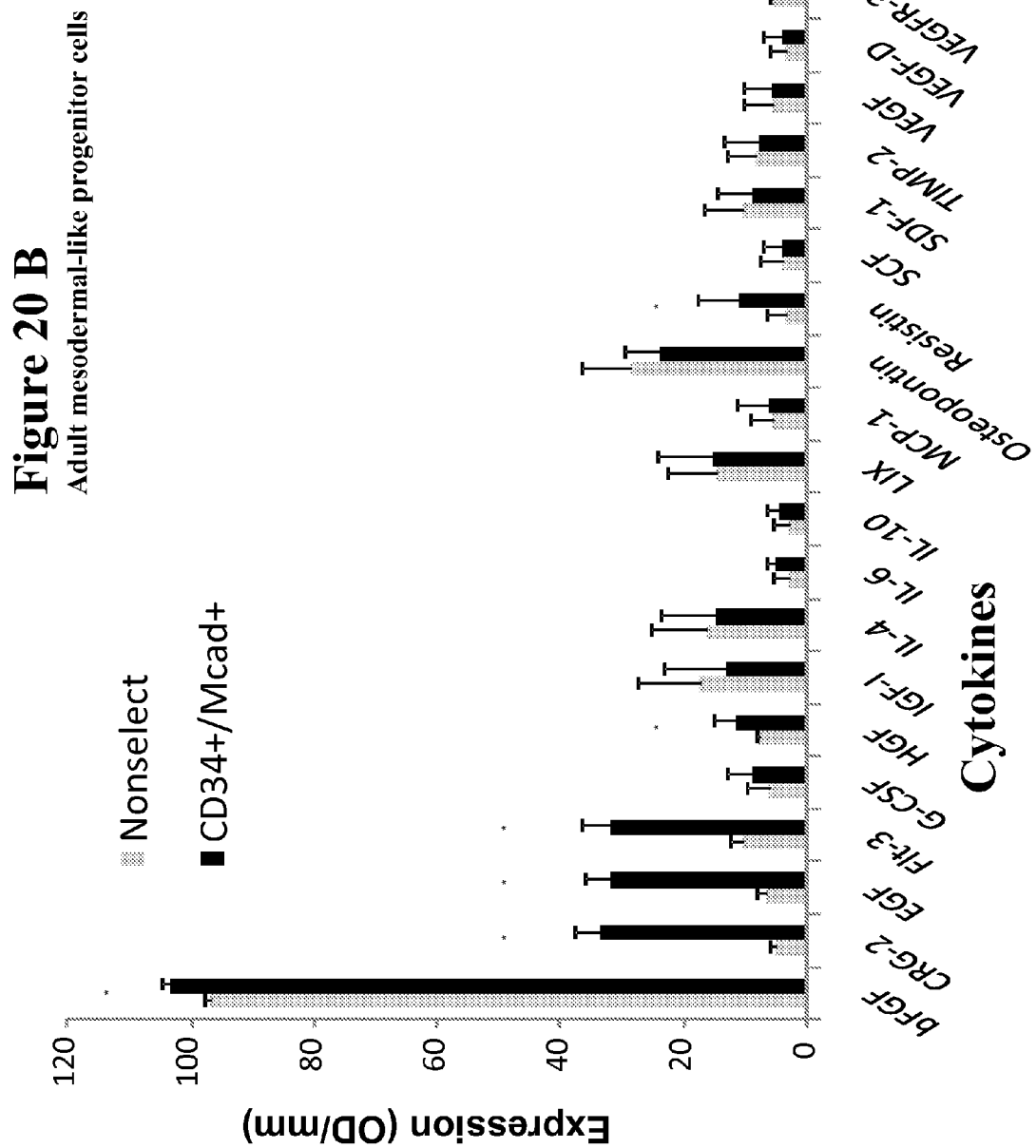

MESODERMAL-LIKE CELL POPULATION FOR TREATING ISCHEMIA IN MAMMALS

CROSS-REFERENCE TO RELATED APPLICATION

This application claims the benefit under 35 U.S.C. §119(e) of U.S. Provisional Patent Application No. 61/246,349 filed Sep. 28, 2009, the disclosure of which is hereby incorporated herein by reference.

BACKGROUND

1. Technical Field

The disclosure generally relates to compositions and methods for treatment of ischemic disorders, particularly ischemic disorders of the extremities associated with compromised blood flow, such as but not limited to limb ischemia. More particularly, the disclosed method features the identification, isolation, expansion and use of mesodermal-like progenitor cells that bear both the CD34 and M-cadherin markers, as a cell therapy.

2. Description of Related Art

Arteriosclerosis is a general term describing any hardening (and loss of elasticity) of medium or large arterial blood vessels characterized by the deposition of fatty substances, primarily cholesterol, and subsequent fibrosis that results from a chronic inflammatory response at the site of the deposit in the artery, resulting in plaque deposition on the inner surface of the arterial wall and degenerative changes within it. Atherosclerosis can eventually lead to plaque ruptures and stenosis (narrowing) of the artery and, therefore, an insufficient blood supply (ischemia) to the tissue or organ it supplies. Medical complications due to atherosclerosis are slow to develop and progress but are cumulative.

Coronary artery disease (CAD) (or atherosclerotic heart disease) is the leading cause of death worldwide and is the end result of the accumulation of plaques within the walls of the arteries that supply the myocardium (the muscle of the heart) with oxygen and nutrients. Vulnerable plaques can suddenly rupture causing the formation of a thrombus (clot) that rapidly slows or stops blood flow, leading to death of the tissues fed by the artery in approximately 5 minutes. Such a catastrophic event is known as an infarction. When it occurs in a coronary artery, it results in a myocardial infarction or heart attack. Since atherosclerosis is a body-wide process, similar events occur also in the arteries to the brain, intestines, kidneys, legs, etc. Another event experienced with advanced CAD is claudication from insufficient blood supply to the legs, typically due to a combination of both stenosis and aneurysmal segments narrowed with clots.

Ischemia is an absolute or relative shortage of the blood supply to a part of the body, when the blood supply is not sufficient to provide adequate oxygenation and the nutritional requirement of the tissue. For example myocardial ischemia is a temporary ischemia of the heart muscle and the cause of angina pectoris, whose symptoms result when the ischemic heart muscle does not function optimally or efficiently, but if the blood flow is improved myocardial ischemia can be reversed. Thus one must distinguish between myocardial ischemia and myocardial infarction. Ischemia can result from many things, such as but not limited to tachycardia, atherosclerosis, hypotension, thromboembolism, sickle cell disease, external compression of a blood vessel or even g-forces. While many of these events result in transient ischemia, if complete ischemia is sustained it can result in cell and tissue necrosis and irreversible damage.

Peripheral artery occlusive disease (PAOD), also known as peripheral vascular disease (PVD,) and most commonly referred to as peripheral artery disease (PAD), encompasses diseases caused by the obstruction of peripheral arteries. This obstruction can be a result of atherosclerosis, inflammatory processes leading to stenosis, an embolism or thrombus formation.

PAD is a common circulatory problem in which narrowed arteries reduce blood flow to the limbs. Lower-extremity PAD affects approximately 8 million Americans. Many people with PAD are asymptomatic or have only mild symptoms with only one in 10 experiencing leg pain when walking, thus PAD may be even more common.

PAD often results from a narrowing of arteries in the legs due to arteriosclerosis. When leg arteries are affected, blood flow to the legs and feet is reduced. Some people may refer to this as poor circulation. But when the blood flow to the legs is significantly reduced, people with PAD may experience pain when walking. Thus, as it advances PAD may become disabling and prevent patients from being able to go to work, and greatly diminishes their quality of life.

Thus a clear and outstanding need exists for a method to treat the more severe symptoms of PAD specifically and ischemia in general. The present disclosure describes just such a technology and treatment method based in regenerative medicine.

BRIEF SUMMARY

In accordance with certain embodiments, a methods are provided for preventing, treating or reducing the severity of tissue ischemia or an ischemia associated disorder in a mammal having, or prone to having, ischemic tissue. In some embodiments, a method of enhancing blood flow in a tissue of a mammal comprises administering to the tissue a therapeutically effective amount of a composition comprising isolated multipotent mammalian mononuclear cells at least 95% of which express both CD34 and M-cadherin cell surface markers, wherein said tissue is ischemic or is prone to ischemia. In some embodiments, an above-described method comprises administering to a host mammal a therapeutically effective amount of a cellular composition comprising isolated multipotent mammalian mononuclear cells (e.g., isolated bone marrow mononuclear cells) which express both CD34 and M-cadherin cell surface markers. In some embodiments, the method comprises administering to a host mammal a therapeutically effective amount of a cellular composition comprising isolated multipotent mammalian mononuclear cells, at least 95% of which express both CD34 and M-cadherin cell surface markers. In some embodiments of an above-described method, the method comprises administering to a host mammal a therapeutically effective amount of a composition comprising isolated multipotent mammalian mononuclear cells, at least 99% of which express both CD34 and M-cadherin cell surface markers. In various embodiments of the above-described methods, less than 10%, or less than 9%, or less than 8%, or less than 7%, or less than 6%, or less than 5%, or less than 4%, or less than 3%, or less than 2%, or less than 1% of the isolated bone marrow mononuclear cells also express Pax3 or Pax7. In some embodiments, an above-described method includes administering a dose of a disclosed composition directly to an ischemic tissue site or an adjacent site in a mammal, wherein the dose comprises $10^2$-$10^{10}$ cells bearing both CD34 and M-cadherin cell surface markers. The administered multipotent mammalian mononuclear cells induce functional new blood vessels in said tissue. In some embodiments, of an above-described method, the mammal has at least one symptom of ischemia in the tissue being treated, and the administered multipotent mammalian mononuclear cells improve at least one such symptom. In some embodiments, the tissue comprises myocardium. In some embodiment, the tissue is vascular tissue in a limb of the mammal. In some embodiments, an angiogenic cytokine is also administered to the tissue.

Also provided in accordance with certain embodiments is a method for inducing functional new blood vessels in a tissue of a mammal by administering to the mammal a therapeutically effective amount of a cellular composition comprising isolated multipotent mammalian mononuclear cells, at least 95% of which express both CD34 and M-cadherin cell surface markers. In some embodiments, the method uses isolated bone marrow mononuclear cells, at least 99% of which express both CD34 and M-cadherin cell surface markers. In some embodiments, less than 10%, or less than 9%, or less than 8%, or less than 7%, or less than 6%, or less than 5%, or less than 4%, or less than 3%, or less than 2%, or less than 1% of the isolated bone marrow mononuclear cells also express Pax3 or Pax7.

Also provided in accordance with certain embodiments is a composition for prevention, treatment or reduction of tissue ischemia or an ischemia associated disorder, comprising a population of isolated mammalian cells in which at least 95% of the cells express both CD34 and M-cadherin cell surface markers. In some embodiments, at least 99% of the isolated bone marrow mononuclear cells express both CD34 and M-cadherin cell surface markers. In various embodiments of, an above-described composition less than 10%, or less than 9%, or less than 8%, or less than 7%, or less than 6%, or less than 5%, or less than 4%, or less than 3%, or less than 2%, or less than 1% of the CD34 and M-cadherin-expressing cells additionally express Pax3 or Pax7. In some embodiments, a pharmaceutical composition comprises an above-described composition in a pharmacologically acceptable carrier.

In accordance with certain embodiments, a process of preparing isolated mesodermal-like progenitor cells comprises (a) obtaining a sample of bone marrow cells, or stem cells from a mammal, or bone marrow cells that have been expanded in vitro; (b) selecting from the sample cells bearing the CD34 marker; (c) from the cells selected in b), selecting cells also bearing the M-cadherin marker, to provide a composition comprising isolated mesodermal-like progenitor cells, at least 95% of which express both CD34 and M-cadherin cell surface markers. In some embodiments, the process also includes (d) excluding from the cells selected in (c) cells bearing Pax3 and/or Pax7 cell surface markers.

In accordance with certain embodiments, a method is provided that comprises administering to a subject having one or more signs or symptoms of ischemia a composition comprising isolated multipotent mammalian mononuclear cells (e.g., isolated bone marrow mononuclear cells), to improve said one or more signs or symptoms of ischemia, wherein at least 95% of said isolated bone marrow mononuclear cells express both CD34 and M-cadherin cell surface markers. In some embodiments, the at least 99% of the isolated multipotent mammalian mononuclear cells, express both CD34 and M-cadherin cell surface markers. In various embodiments of an above-described method, the less than 10%, or less than 9%, or less than 8%, or less than 7%, or less than 6%, or less than 5%, or less than 4%, or less than 3%, or less than 2%, or less than 1% of the isolated multipotent mammalian mononuclear cells expressing both CD34 and M-cadherin also express Pax3 or Pax7.

In accordance with an embodiment of the invention, a diagnostic method for ischemia or at risk of ischemia is provided, which comprises determining the level and/or distribution of cells bearing both CD34 and M-cadherin cell surface markers in a tissue sample from a patient having ischemia or at risk of developing ischemia in said tissue. The resulting level and/or distribution is then compared to that of cells in the same tissue not bearing both said markers; and, based on the comparison, it is determined whether the patient is eligible for transplantation of autologous $CD34^+$/M-cadherin$^+$ mesodermal-like precursor cells at an ischemic site or a site at risk of developing ischemia. In some cases, the presence of cells bearing both CD34 and M-cadherin cell surface marker is indicative of tissue that is self repairing. In some cases, such as post-transplantation of autologous $CD34^+$/M-cadherin$^+$ mesodermal-like precursor cells at an ischemic site or a site at risk of developing ischemia, a similar method is performed to determine whether the transplant was effective to induce new angiogenesis at the site.

In accordance with another embodiment of the invention, a method of predicting the angiogenesis potential of a tumor is provided which comprises determining the level and/or distribution of cells bearing both CD34 and M-cadherin cell surface markers in a tumor tissue sample from a patient. The resulting level and/or distribution is then compared to that of non-tumor cells from adjacent tissue not bearing both said markers; and, based on the comparison, it is determined whether the angiogenesis potential of the tumor is increased as compared to adjacent non-tumor tissue in the patient. Increased angiogenesis potential of said tumor is indicated if the relative level and/or distribution of cells bearing both markers is increased in the tumor tissue sample.

In some embodiments, the presence of CD34 and M-cadherin expressing cells in the tumor tissue sample is indicative of new vessel growth (angiogenesis) in the tumor. For example, in some cases a more malignant (angiogenic) tumor is considered potentially more pathogenic or malignant than tumors that cannot induce angiogenesis and which would be limited in potential size growth.

In some embodiments, the above-described isolated bone marrow mononuclear cells (BMCs) are autologous. In some embodiments the BMCs are heterologous to the mammal. In various embodiments, the isolated BMCs are isolated using a fluorescence activated cell sorter or magnetic bead based system. Various embodiments of an above-described method or composition are used to prevent, treat or reduce the severity of tissue ischemia or an ischemia associated disorder in a mammal having or prone to having ischemic tissue. For example, in many instances the mammalian host subject or patient is a human, companion animal, animal used in sports, farm animal, or a mouse or other laboratory animal model. These and other embodiments, and various features and advantages will be apparent in the description and drawings.

BRIEF DESCRIPTION OF THE DRAWINGS

FIG. 1A shows a representative transverse section (8 μm) of an ischemic leg 7 days after transplantation of bone marrow mononuclear cells. $GFP^{+/+}$ bone marrow mononuclear cells are identifiable in the vasculature and between muscle fibers. FIG. 1B shows that at 21 days, $GFP^{+/+}$ bone marrow mononuclear cells have formed parallel sheet-like structures suggestive of skeletal muscle formation in bundles within the ischemic limbs. Scale bar=20 μM.

Figure 2A:
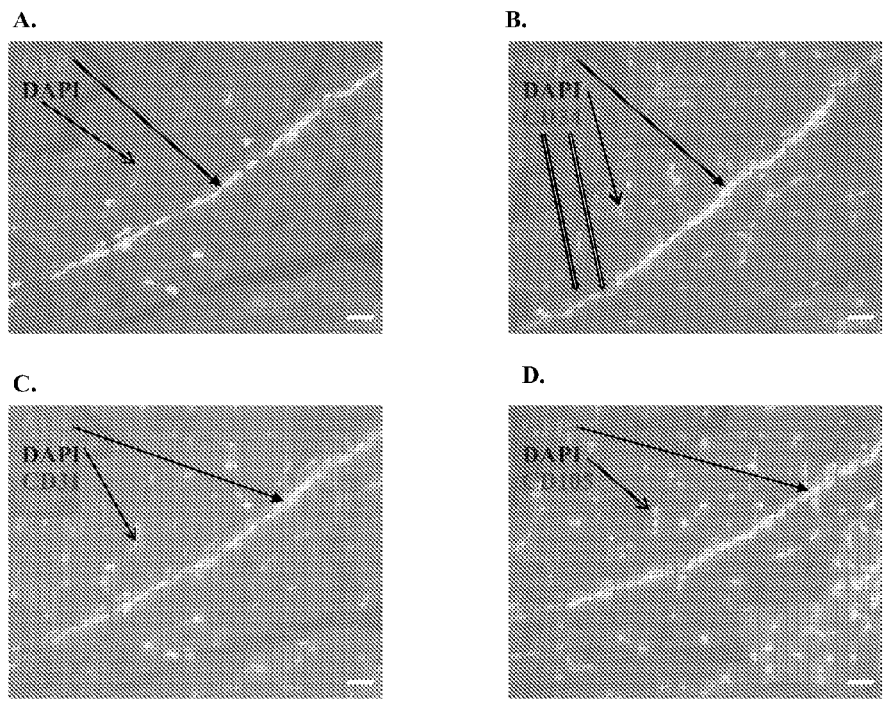
FIGS. 2a and 2b show the formation of CD34 and GFP positive cord-like structures within ischemic hind limbs.
Figure 2B:
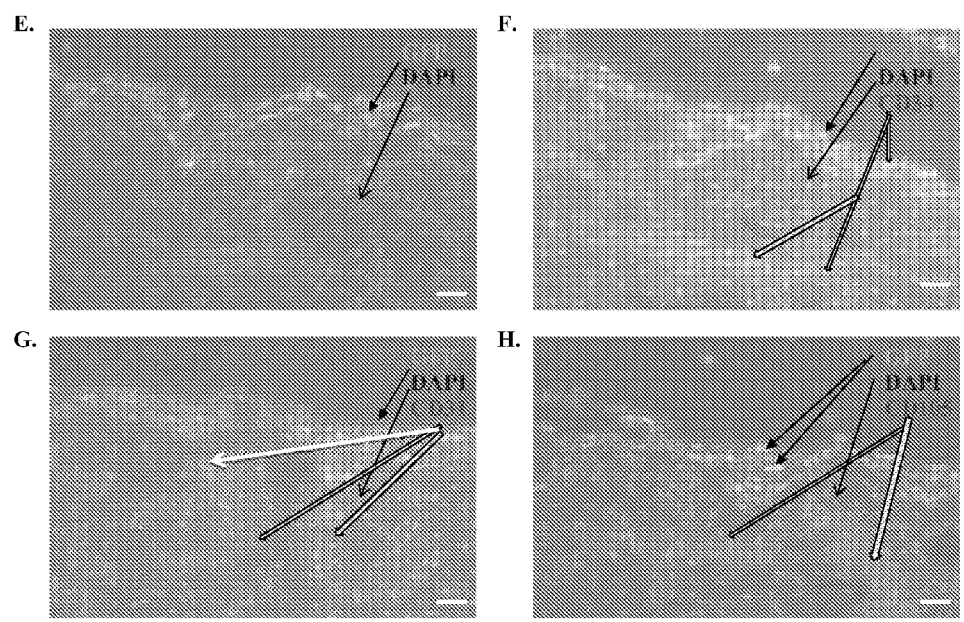

Cord-like structures composed of GFP positive cells were seen at 7 days post treatment as shown in FIG. 2a panels A-D, and at 14 days after treatment (as seen in FIG. 2b panels E-H) with bone marrow mononuclear cell transplantation. Cross sections of the limbs that were also stained without primary antibody are shown in FIGS. 2a panels A and 2b panel E. Limbs immunostained with primary antibodies that bound CD34 (shown at 7 days in FIG. 2a panel B and at 14 days in FIG. 2b panel F), CD31 (shown at 7 days in FIG. 2a panel C and at 14 days in FIG. 2b panel G), or CD105 (as shown at 7 days in FIG. 2a panel D and at 14 days in FIG. 2b panel H). Cell nuclei were also stained with DAPI. Scale bar=20 μM.

Figure 3A:
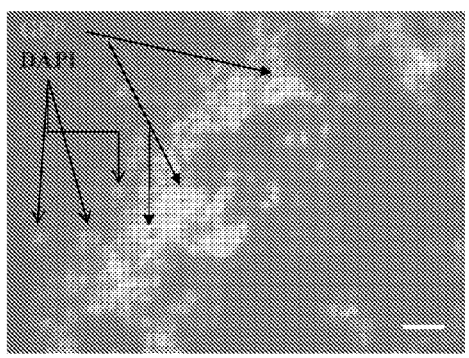
Figure 3A:
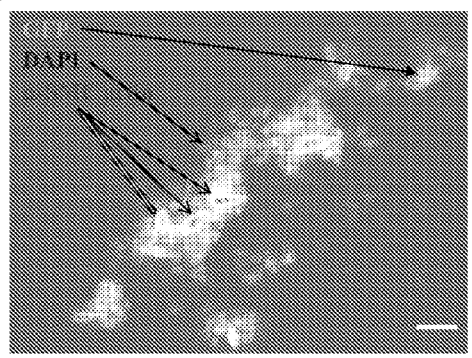
Figure 3B:
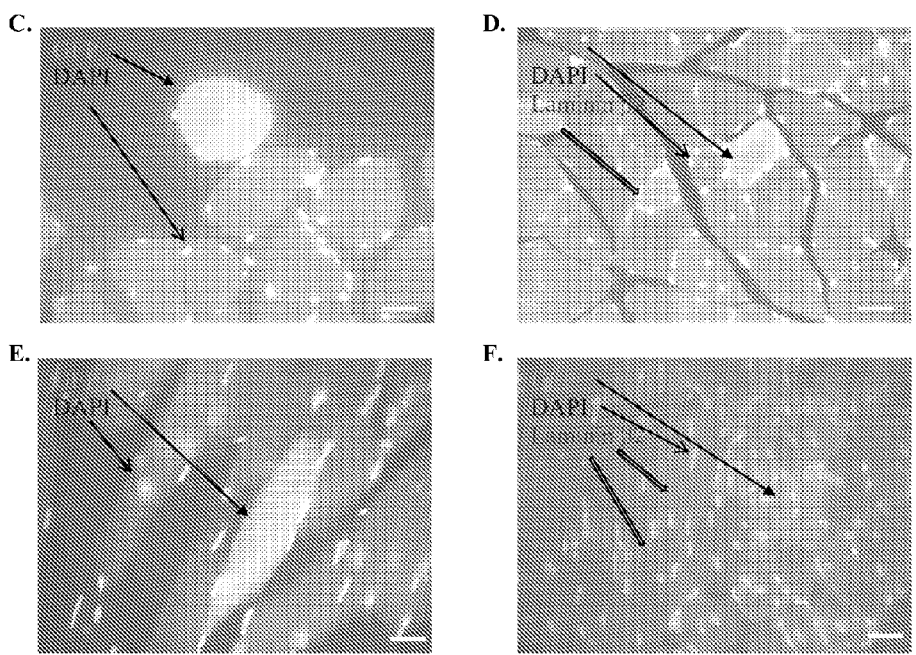

FIGS. 3a and 3b show the differentiation of donor bone marrow mononuclear cells into vessels, skeletal muscle fibers and supporting membranes. Twenty-one days after transplantation, cells formed α-smooth muscle actin-positive arteries (as shown in FIG. 3a panel B) and laminin-β2-positive myofibers (as shown in FIG. 3b panels C and D). At 28 days, a large GFP-positive myofiber and cluster (as shown in FIG. 3b panels E and F) were identified. Cell nuclei were stained with DAPI. Scale bar=20 μM.

Figure 4:
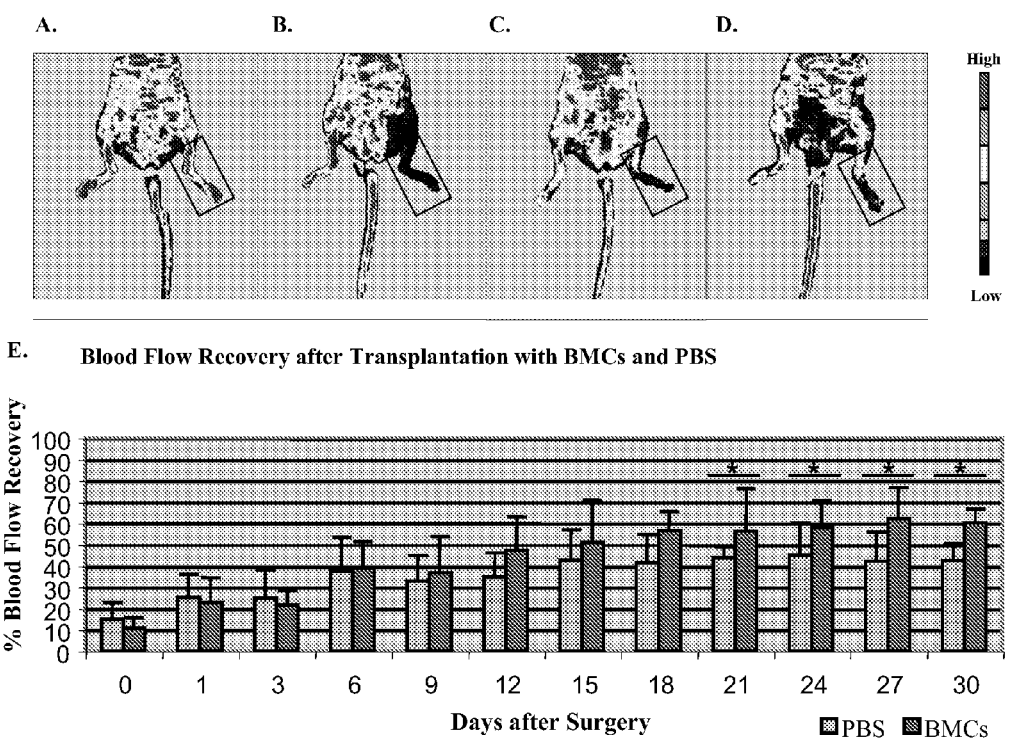

FIG. 4 shows that donor bone marrow mononuclear cells restored blood flow to ischemic hind limbs. Laser Doppler images taken before surgery/treatment (day 0), and at 1, 12, and 27 days (as shown in FIGS. 4A-D, respectively) after transplantation. FIG. 4E shows the percent blood flow recovery ([perfusion of ischemic:non-ischemic limb]×100) was significantly higher (*P<0.05) in bone marrow mononuclear cell (BMC)-injected mice than in control (PBS treated) mice at 21 days after transplantation.

Figure 5:
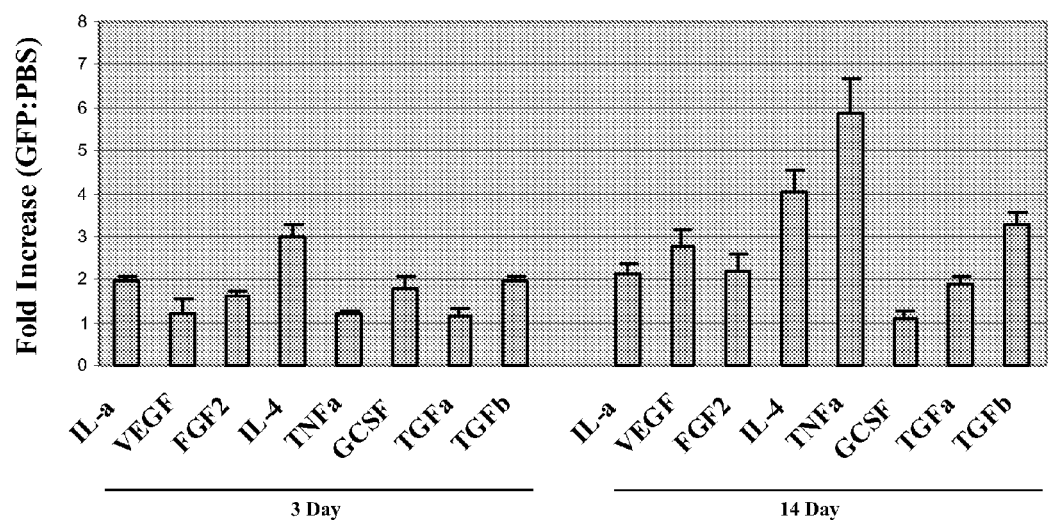

FIG. 5 shows results of an assay for an array of angiogenesis factors. Blood samples were obtained from mice whose ischemic hind limbs were injected with bone marrow mononuclear cells or control (PBS) at 3 and 14 days post surgery/treatment. An array of antibodies was used to identify the presence of antigenic factors in the blood and it was determined that VEGF, $FGF_2$, IL-4, TNFα, and TGFα/β were up regulated in mice receiving bone marrow mononuclear cells at both 3 and 14 days post surgery/treatment.

Figure 6:
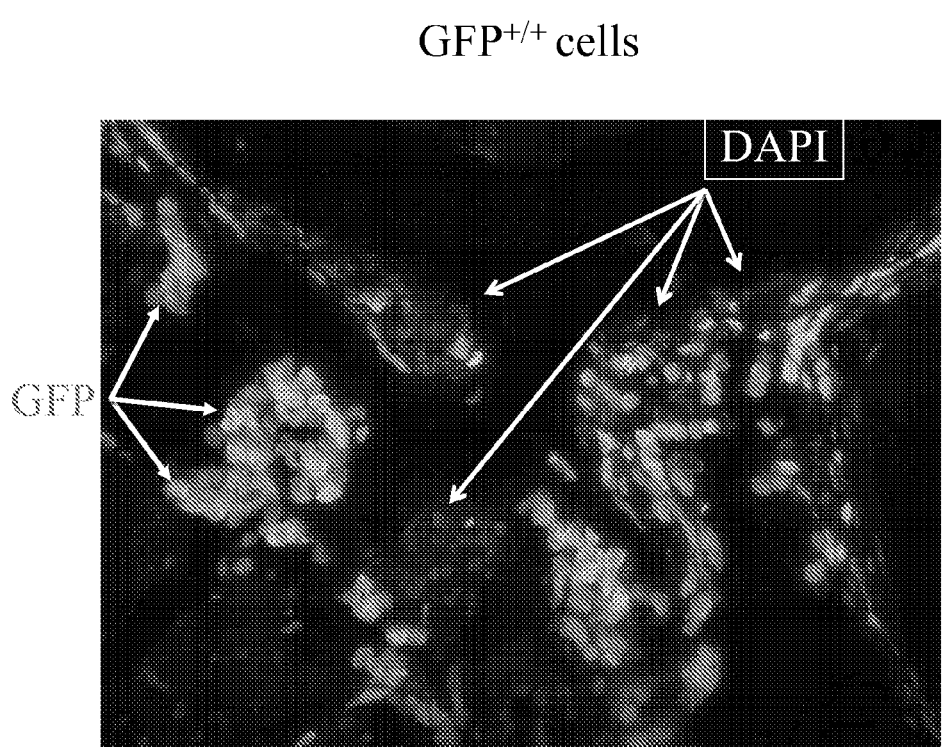

FIG. 6 shows the identification of $GFP^{+/+}$ bone marrow mononuclear cells in mouse ischemic hind limbs 7 days after intra-arterial injection of unfractionated $GFP^{+/+}$ donor bone marrow mononuclear cells. Abundant donor derived $GFP^{+/+}$ cells were observed to accumulate in the vascular and muscular region throughout the ischemic leg.

Figure 7:
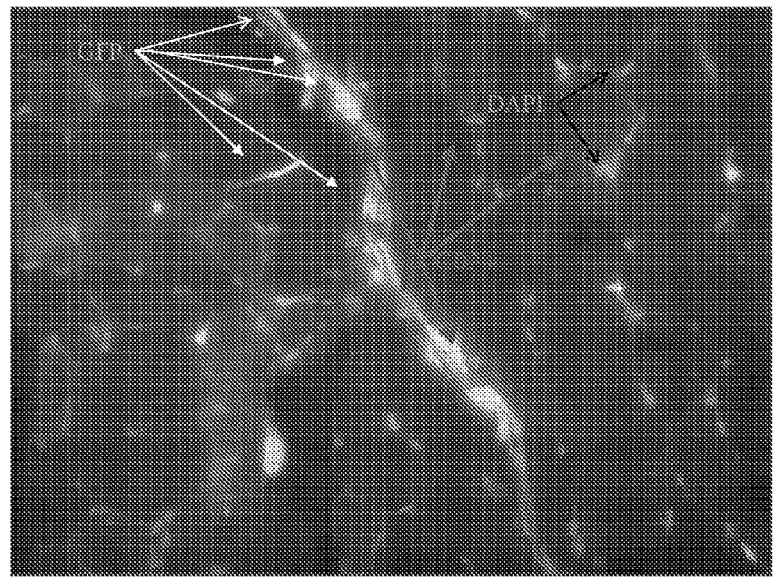

FIG. 7 shows the identification of $CD34^+$ cells present in mouse ischemic hind limbs at 7 days after intra-arterial injection of unfractionated $GFP^{+/+}$ donor bone marrow mononuclear cells, demonstrating that a fraction of donor derived $GFP^{+/+}$ cells stain positive for the endothelial progenitor marker CD34.

Figure 8:
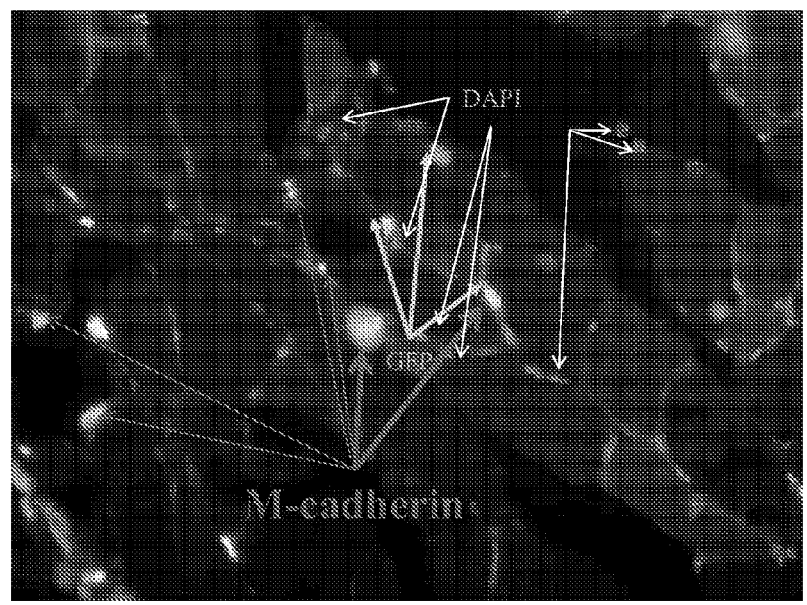

FIG. 8 shows the identification of M-cadherin+ cells present in mouse ischemic hind limbs at 7 days after intra-arterial injection of unfractionated GFP+/+ donor bone marrow mononuclear cells, demonstrating that a fraction of donor derived GFP+/+ cells also stain positive for the skeletal cell marker M-cadherin.

Figure 9:
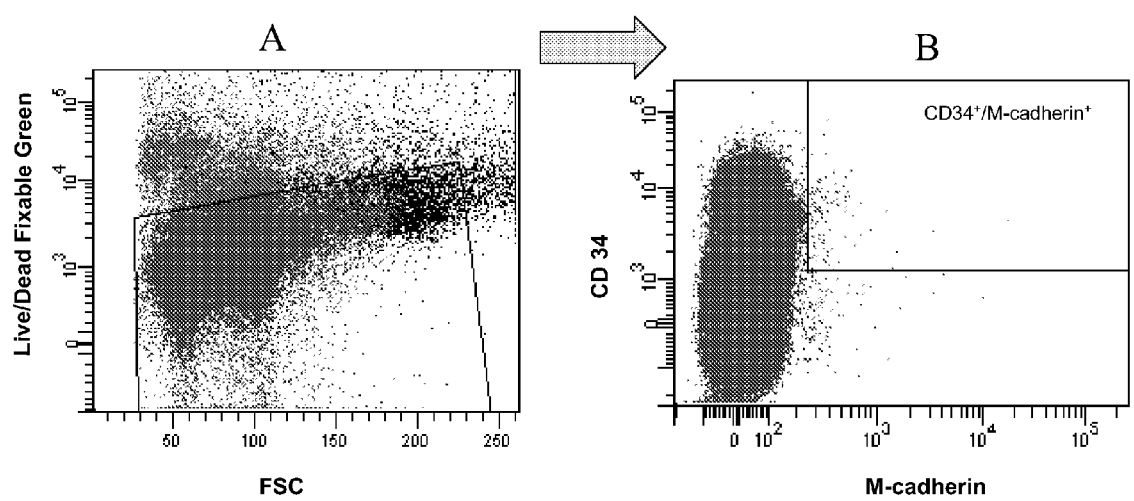

FIG. 9 shows the initial identification of double positive CD34+/M-cadherin+ bone marrow mononuclear cells in mouse bone marrow using a multi-parameter flow cytometric analysis. FIG. 9A is a scattergram that illustrates the gating of live mononuclear cells from freshly isolated mouse bone marrow using a flow cytometer. The scattergram shown in FIG. 9B shows that the double positive CD34+/M-cadherin+ cell population (cells within the interior rectangle) appears to represent a relatively rare subset of bone marrow mononuclear cells (0.02%±0.003%). This figure was obtained using fluorescein (FITC)-conjugated anti-mouse CD34 (eBioscience, San Diego, Calif.), and /or a monoclonal anti-M-cadherin antibody (H-71, purchased from Santa Cruz Biotechnology, Santa Cruz, Calif.)

FIGS. 10A-G show that the double positive $CD34^+$/M-cadherin$^+$ cell population is also express Sca-1 and other endothelial progenitor cell markers, including $VEGFR_2$ and Tie-2. Additionally, the double positive $CD34^+$/M-cadherin$^+$ cell population appeared to be enriched for mesenchymal cell markers CD29 and CD73 and in the key stem cell mobilization molecules, CXCR4 and CD44. The percent PE+ cells are those cells (as a % of the total counted) that bound sufficient labeled antibody to surpass cutoff.

Figure 11:
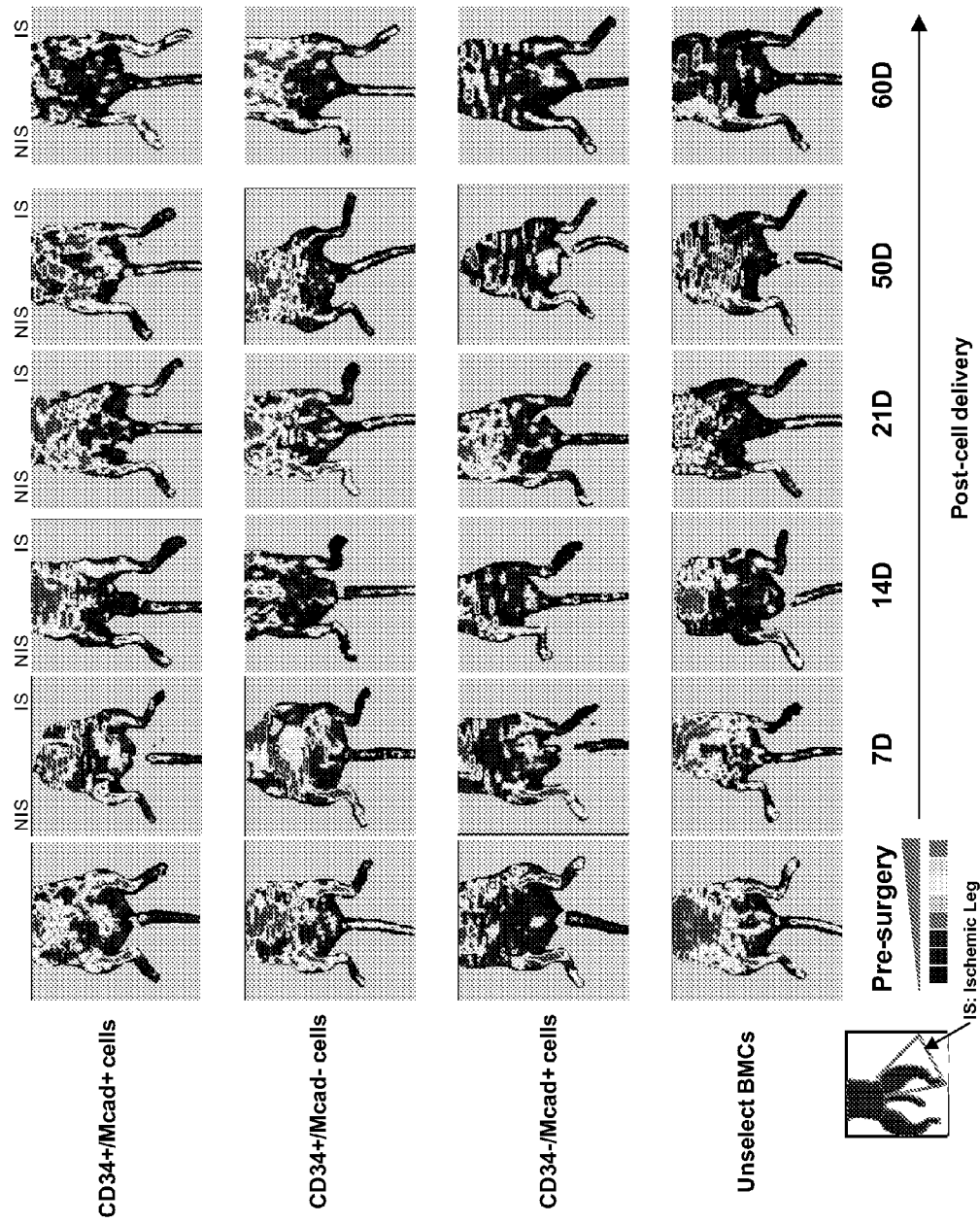

FIG. 11 illustrates the recovery of blood flow in the ischemic limbs of $ApoE^{-/-}$ mice treated with $CD34^+$/M-cad$^+$ BMCs. Representative laser Doppler perfusion images taken at indicated intervals for the 4 treatment groups (n=9-11/group). Blood perfusion in the ischemic hindlimbs was markedly increased in the $CD34^{+/}$M-cad$^+$ BMC group compared with other cell treatment groups. IS=ischemic legs, NIS=nonischemic legs.

Figure 12:
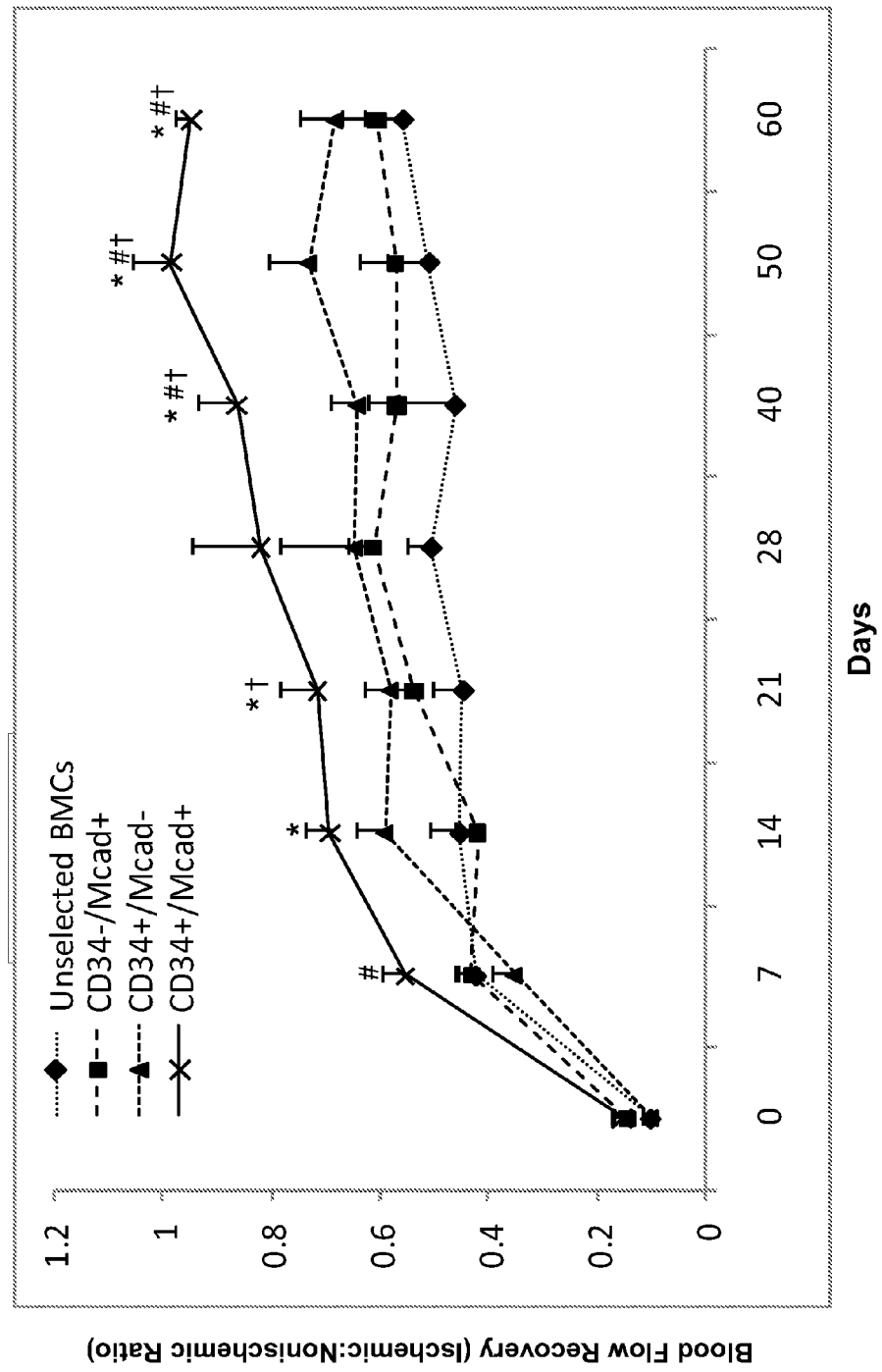

FIG. 12 graphically represents quantitative analysis of hindlimb blood perfusion. The increase in ischemic:nonischemic ratio was significantly higher in the $CD34^+$/M-cad$^+$ BMC group compared with other treatment groups at multiple time points. Data are expressed as mean±SEM, n=9-11/group. *P<0.01, $CD34^+$/Mcad$^+$ vs unselected BMC group; #P<0.05, $CD34^+$/Mcad$^+$ vs $CD34^+$/Mcad$^-$; †P<0.05, $CD34^+$/Mcad$^+$ vs $CD34^-$/Mcad.$^+$ Maximal blood flow perfusion was set at 1.0 compared to the contralateral leg after femoral artery ligation.

Figure 13A:
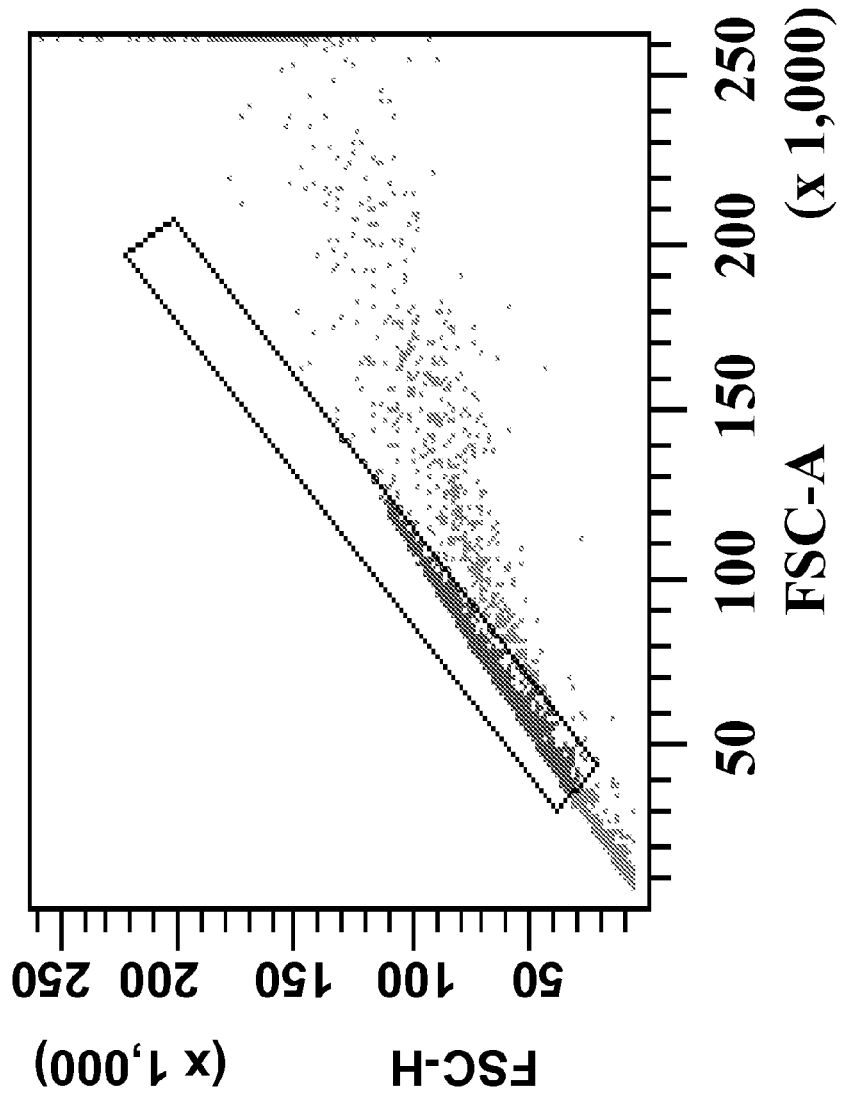
Figure 13B:
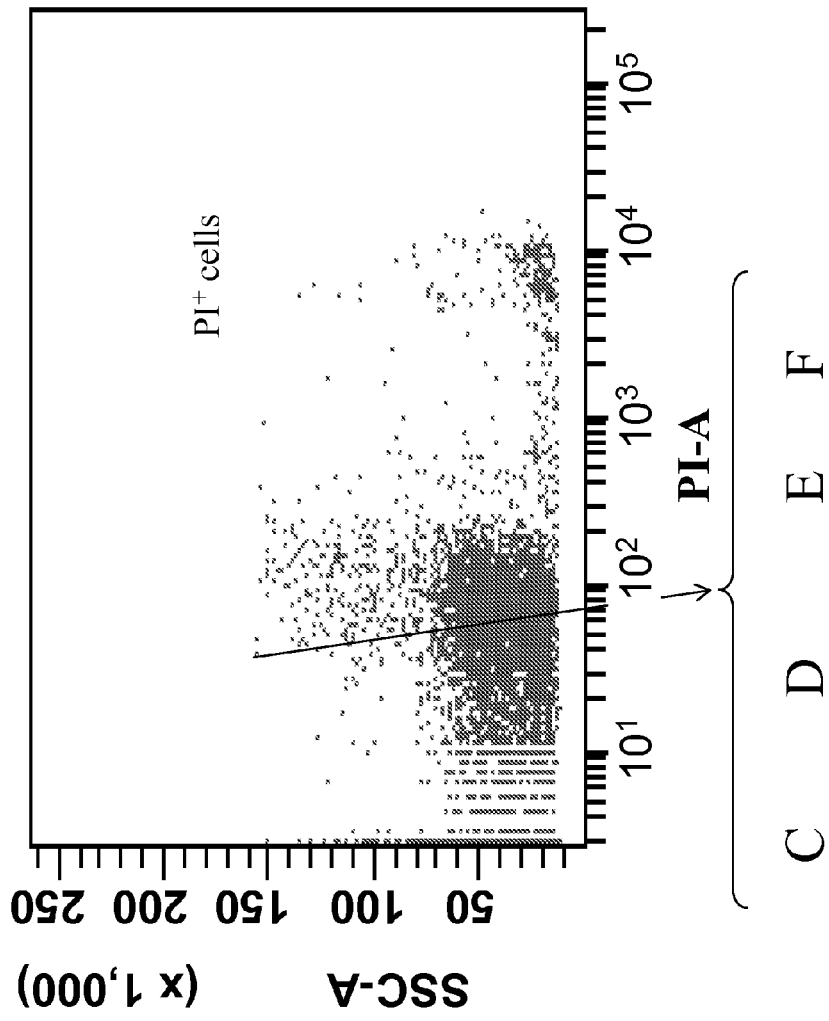
Figure 13C:
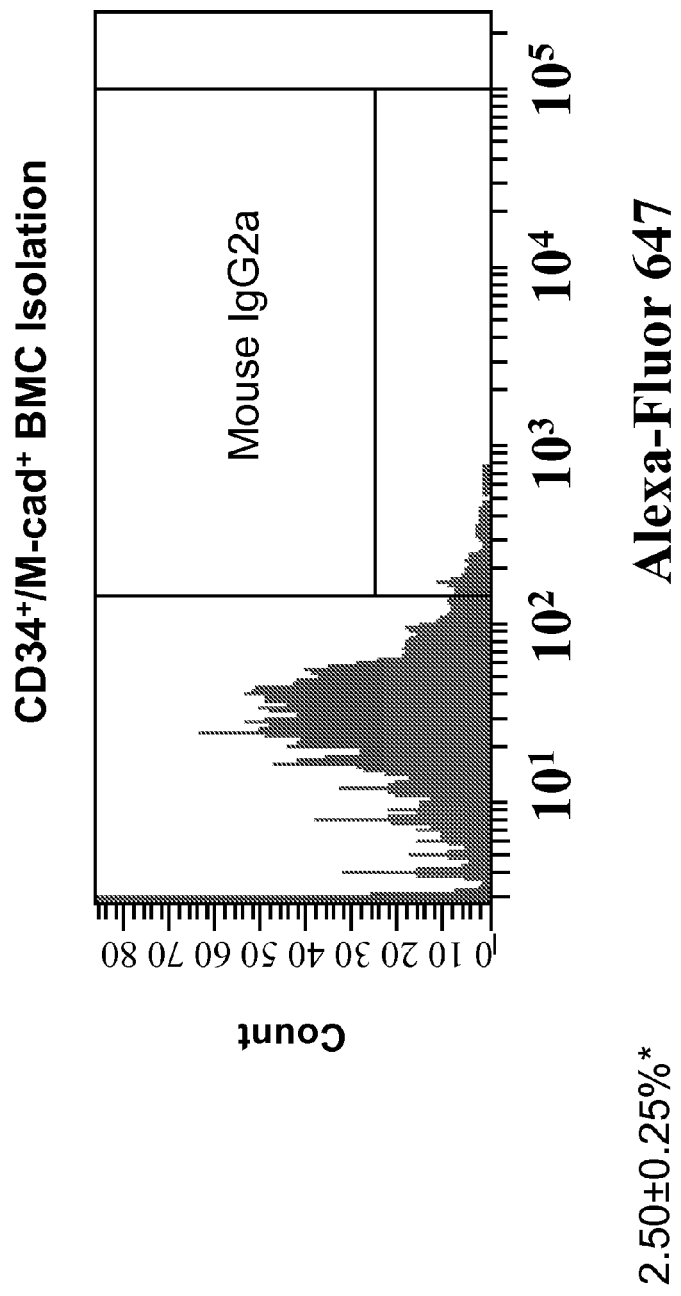
Figure 13D:
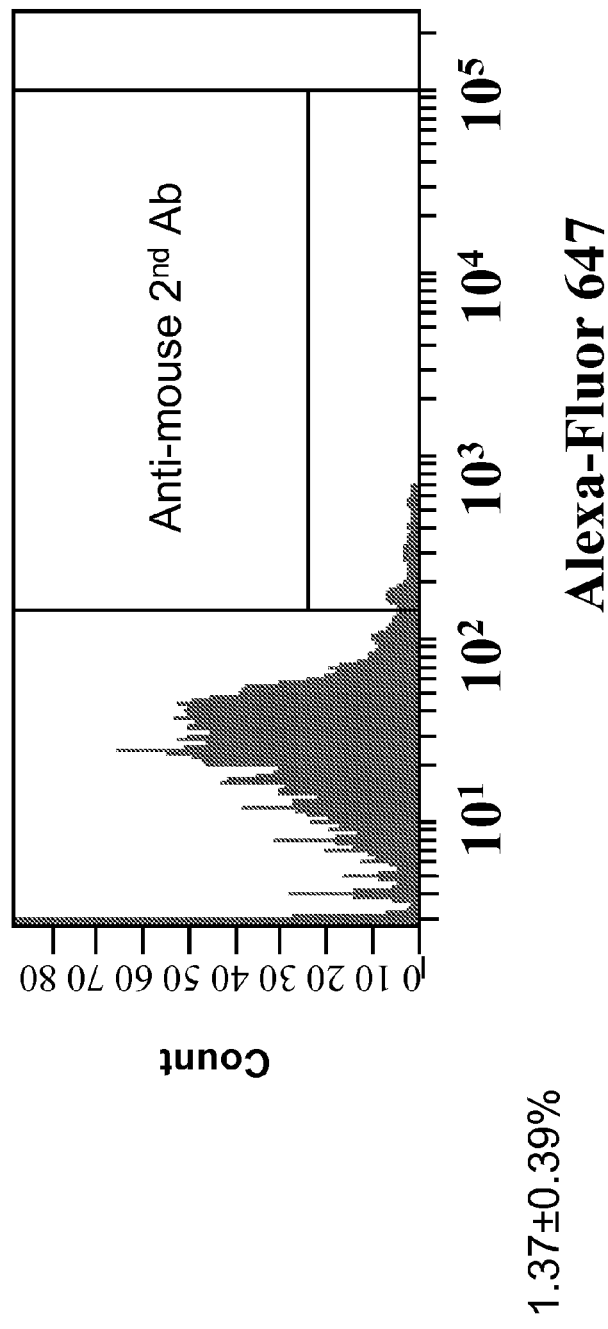
Figure 13E:
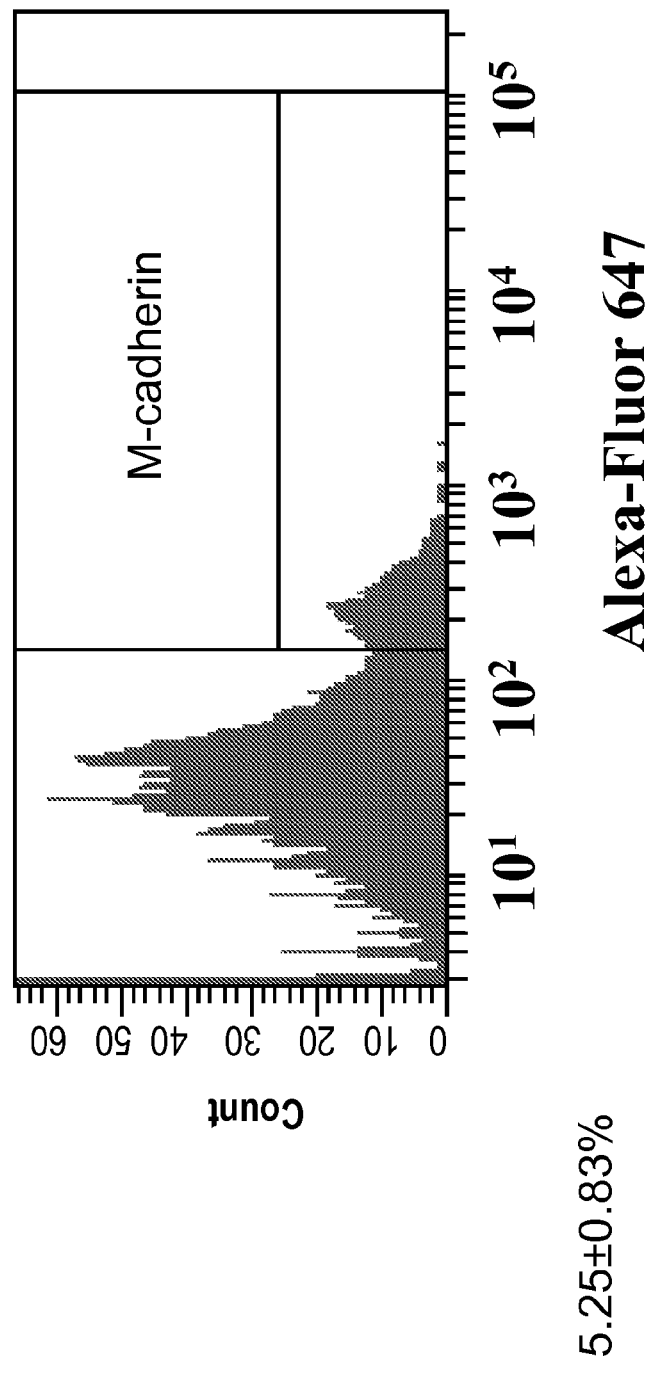
Figure 13F:
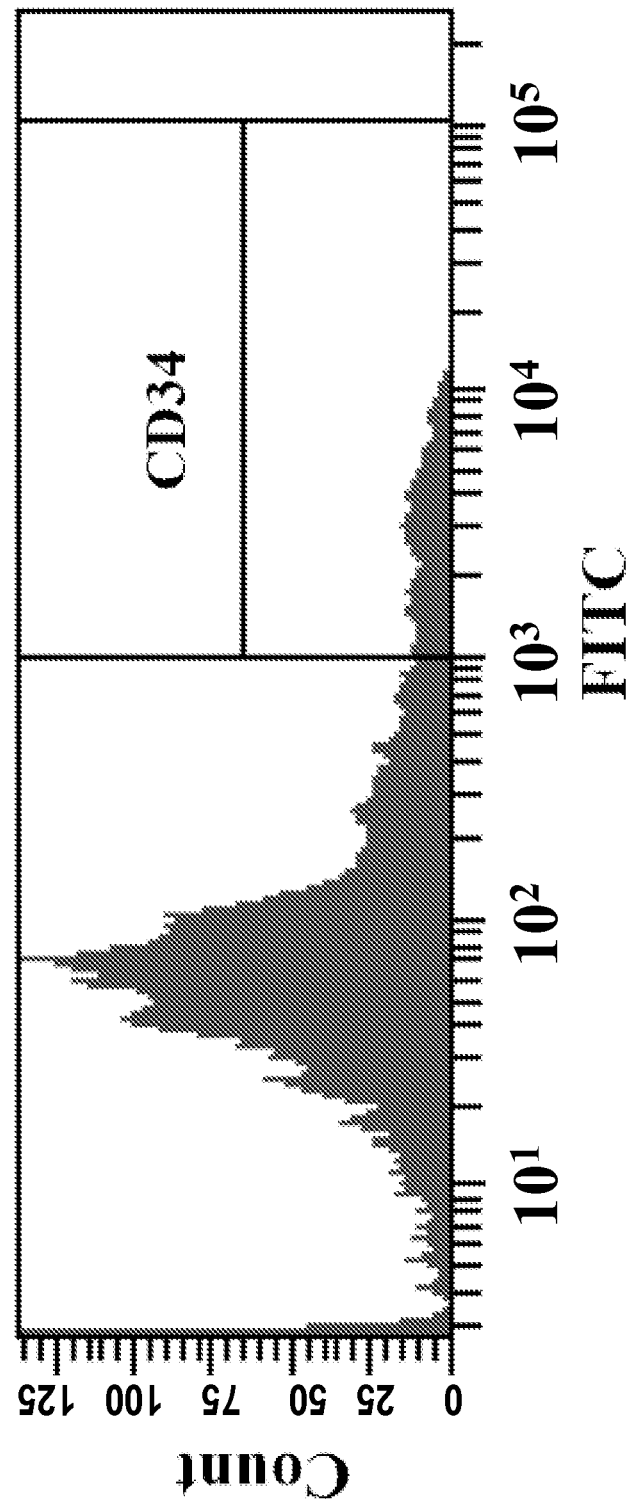

FIGS. 13A-F illustrate the identification and enumeration of bone marrow mononuclear cells first using forward scatter characteristics (FIG. 13A) and then using staining with propidium iodide (PI) to identify viable cells (FIG. 13B). These cells were then stained using fluorescent dye labeled antibodies selective for mouse IgG2a (FIG. 13C), an anti-mouse 2$^{nd}$ antibody control (FIG. 13D), M-cadherin antibody (FIG. 13E), or CD34 antibody (FIG. 13F).

Figure 14:
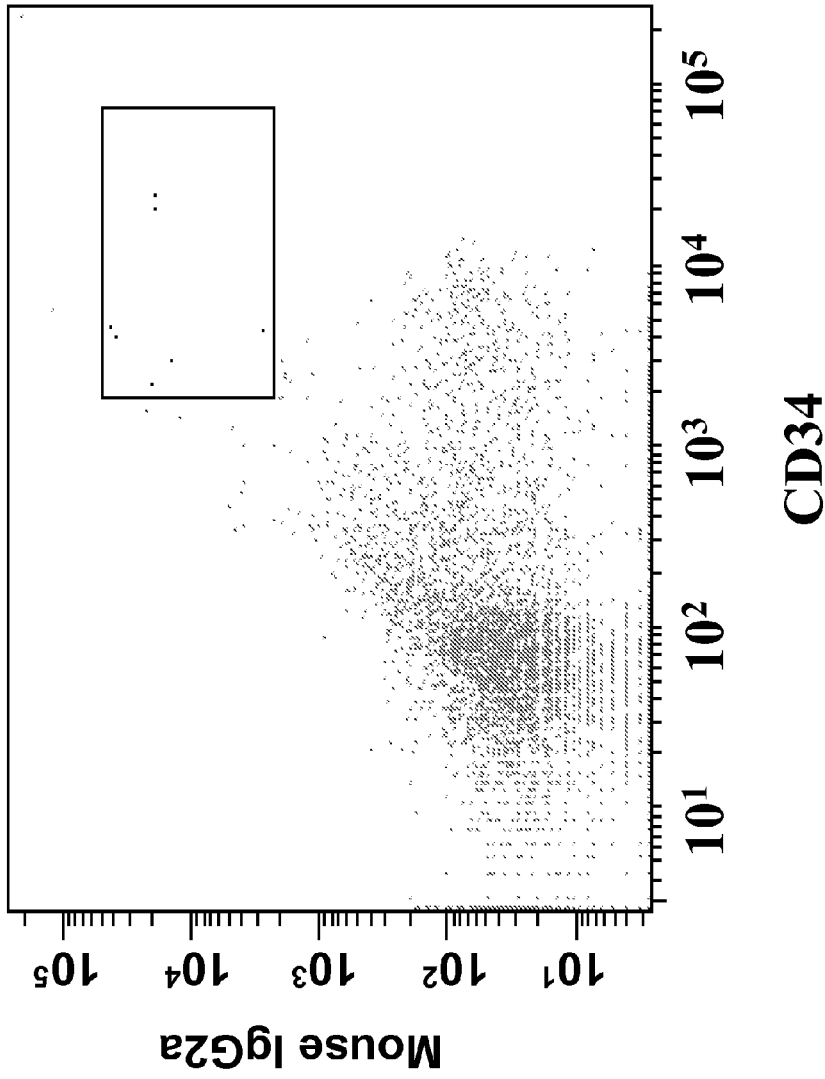
Figure 14:
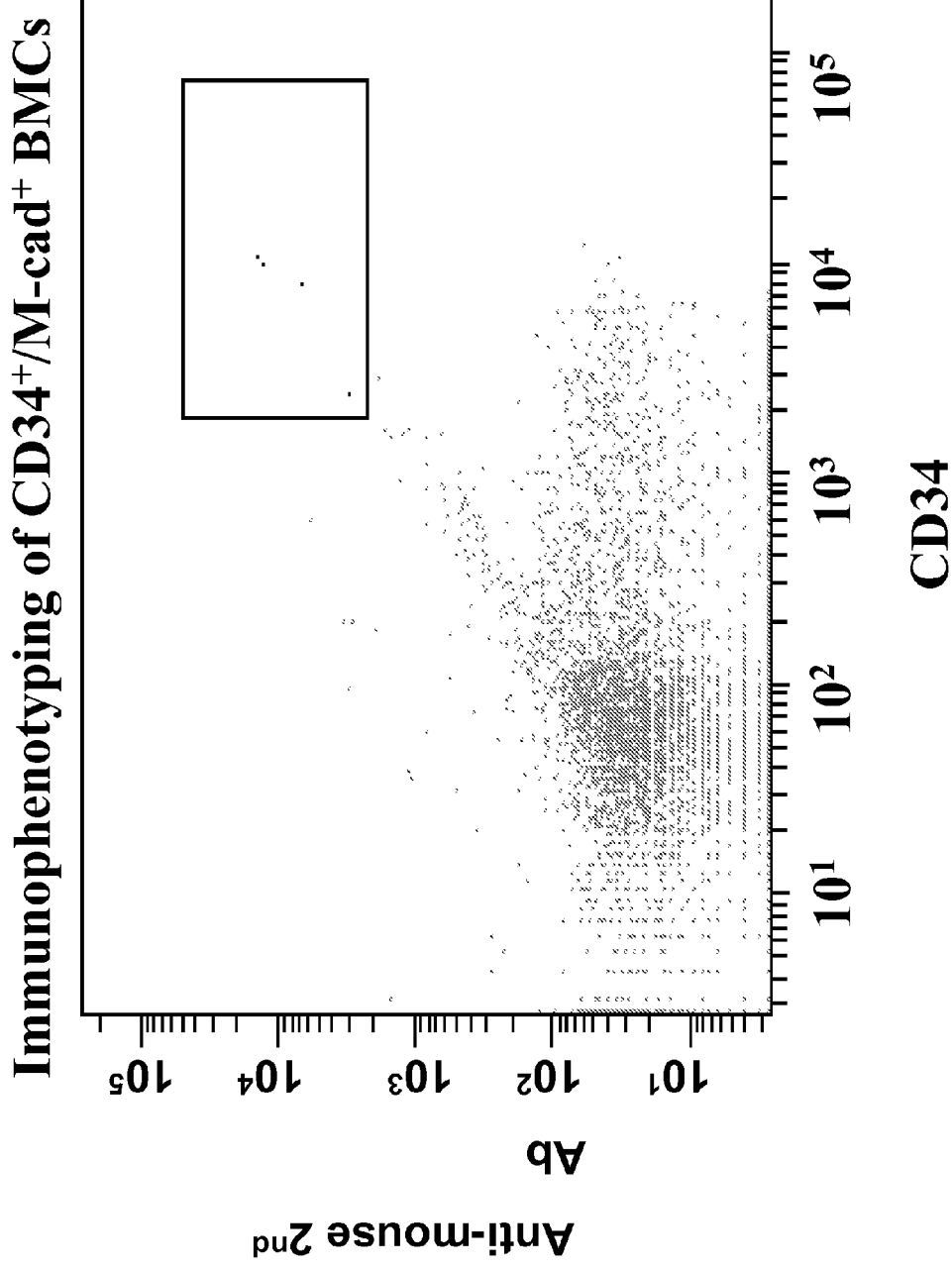
Figure 14:
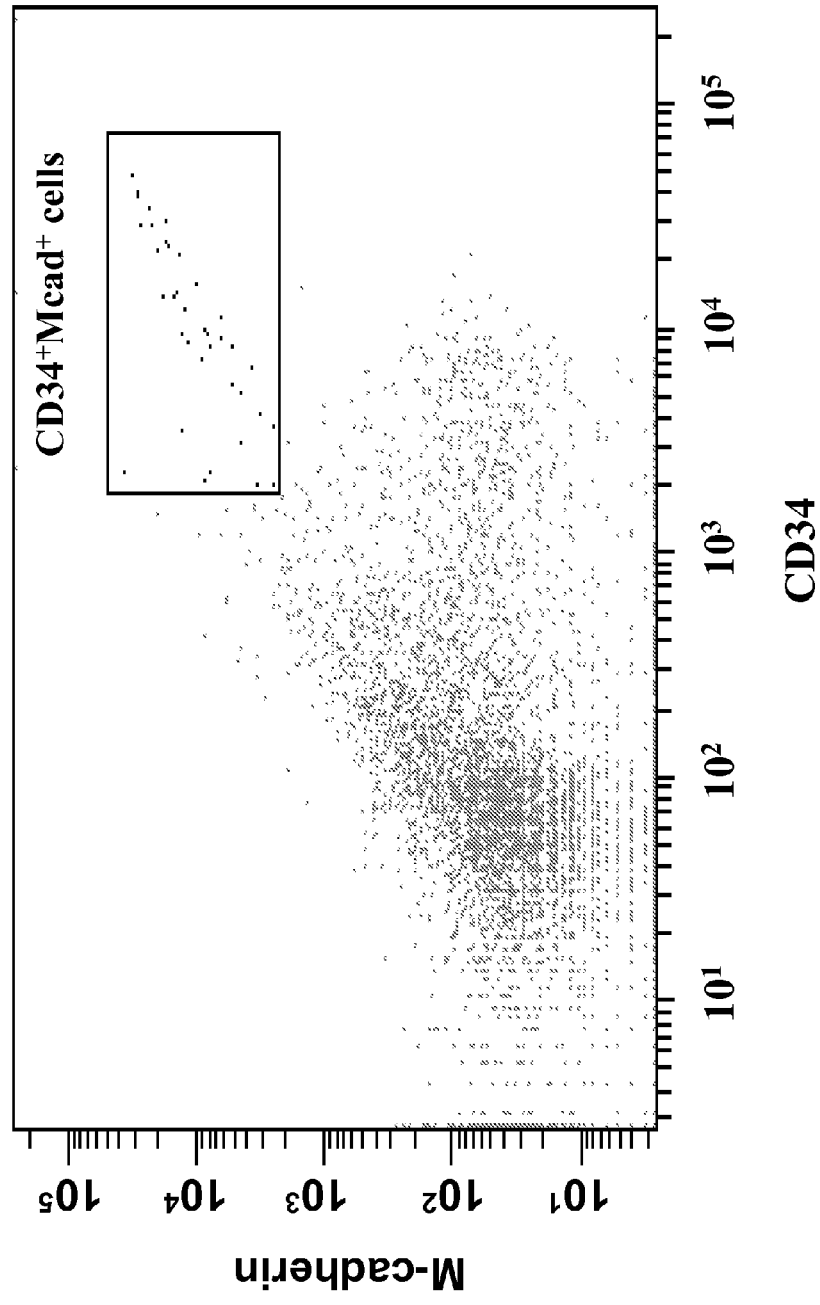
Figure 14:
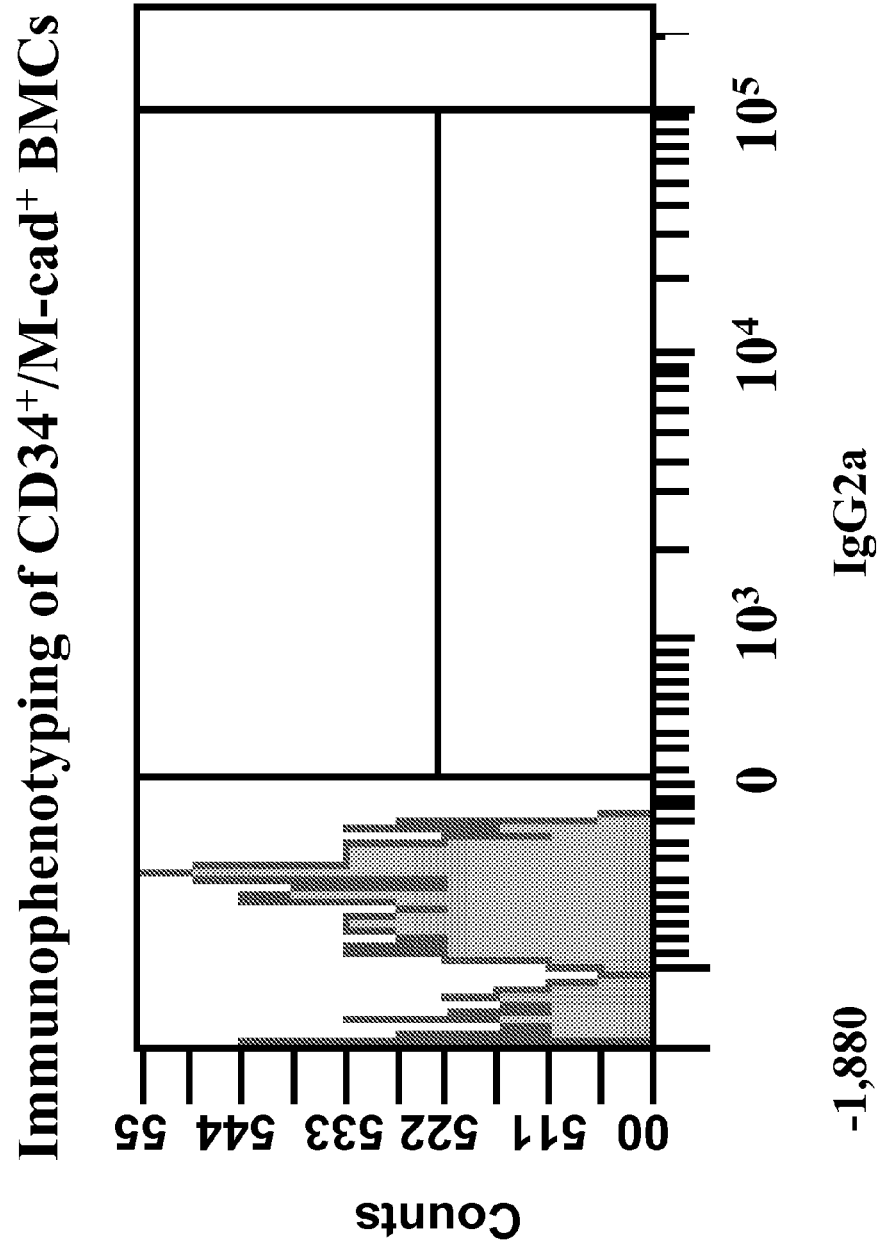
Figure 14:
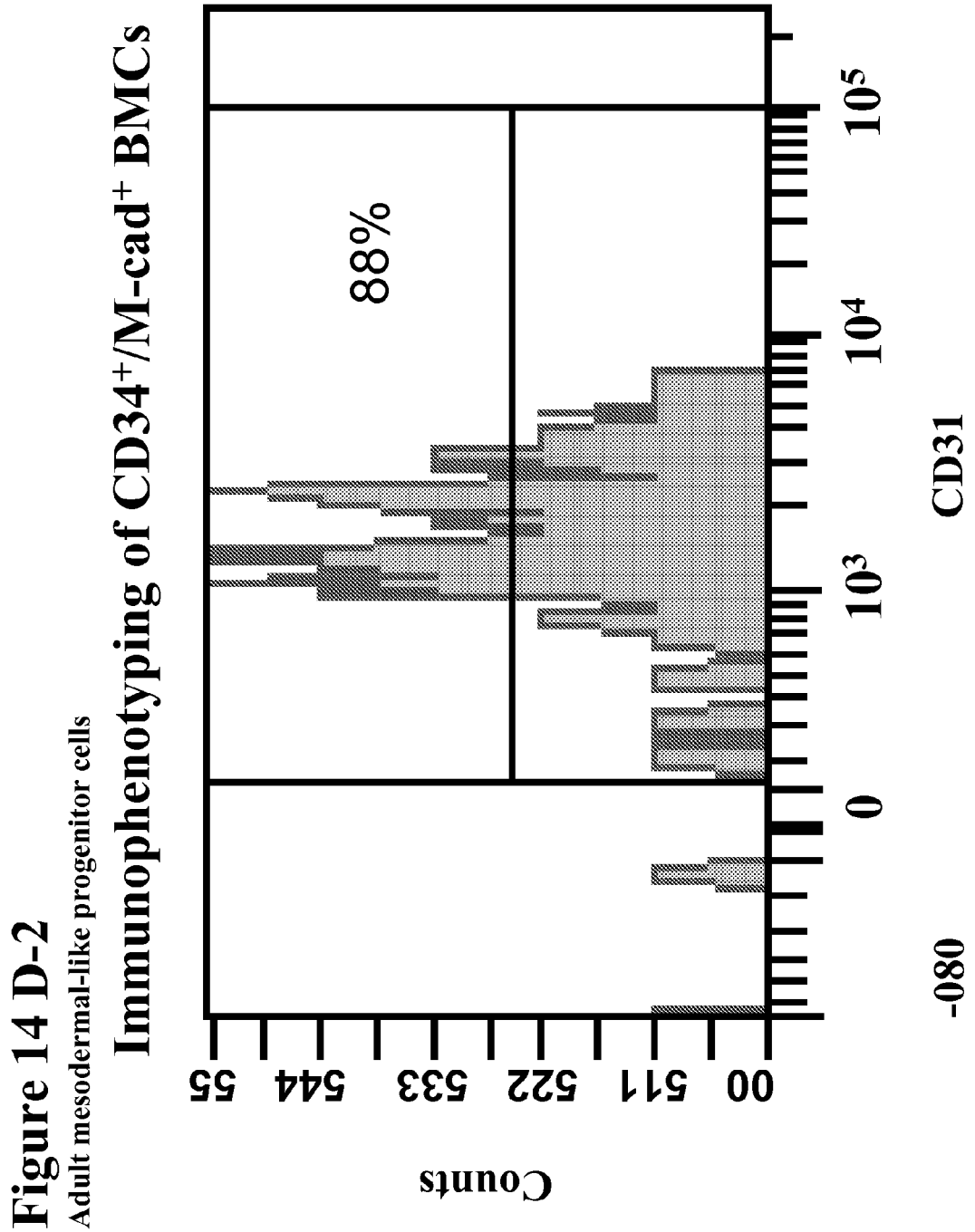
Figure 14:
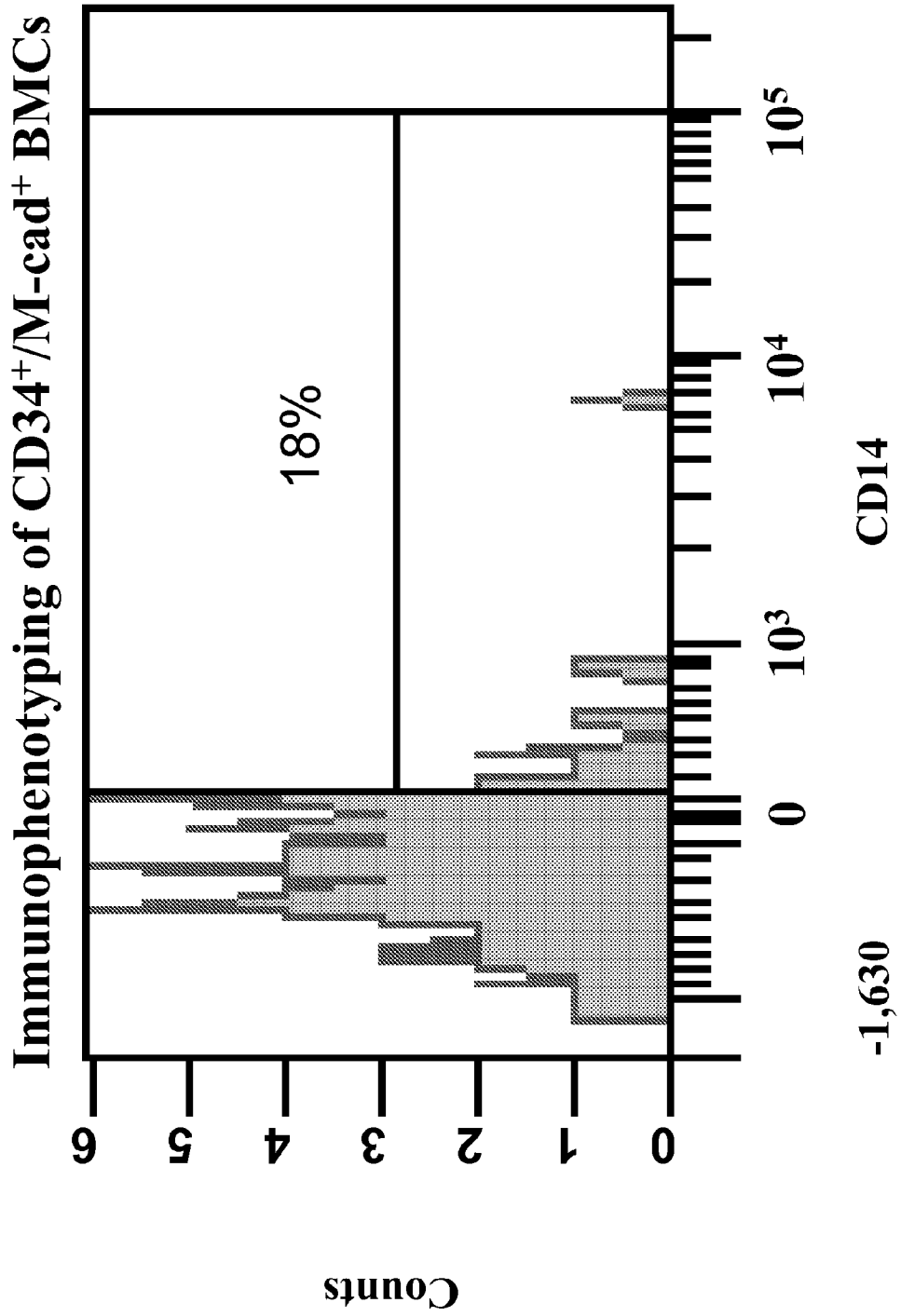
Figure 14:
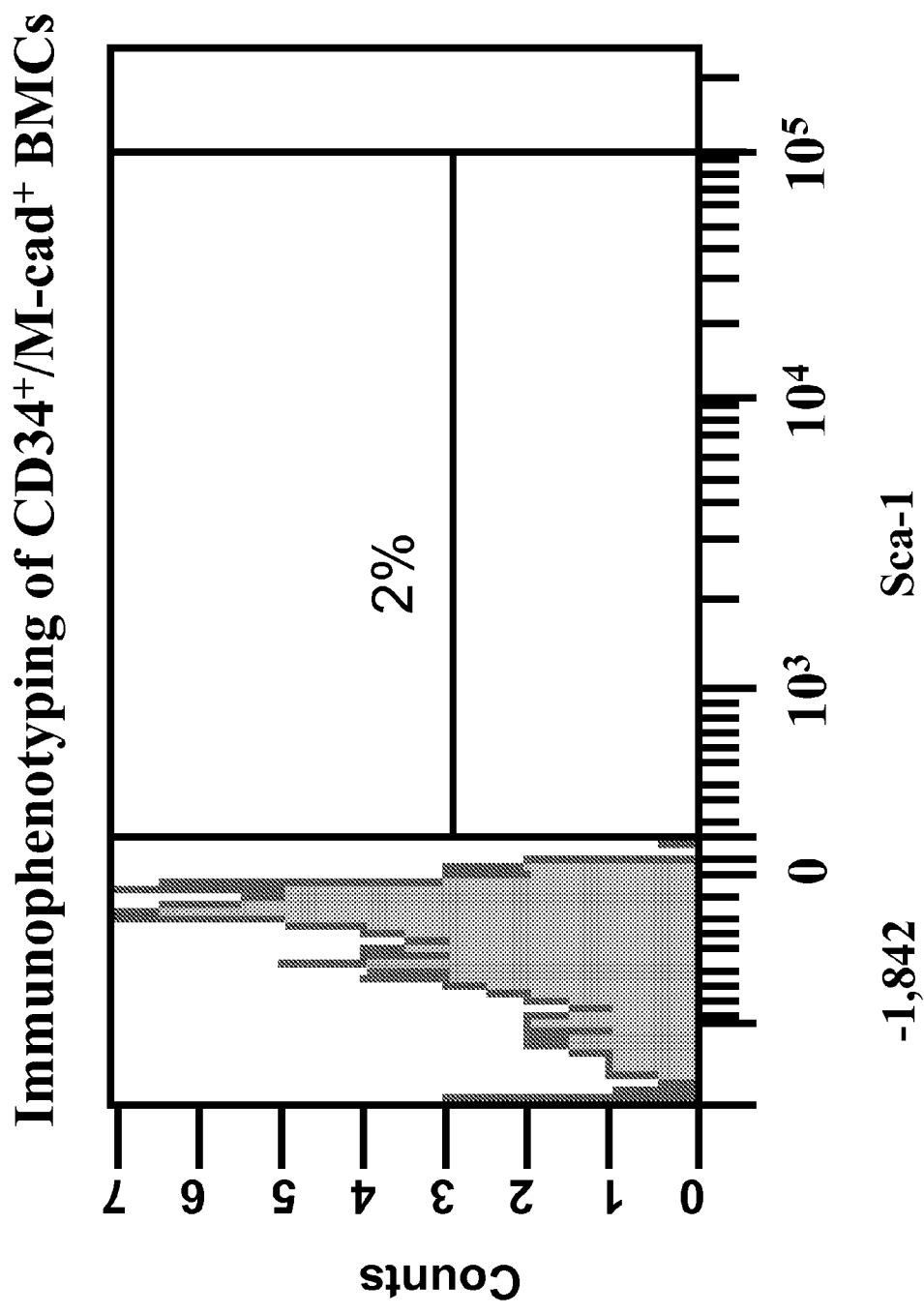
Figure 14:
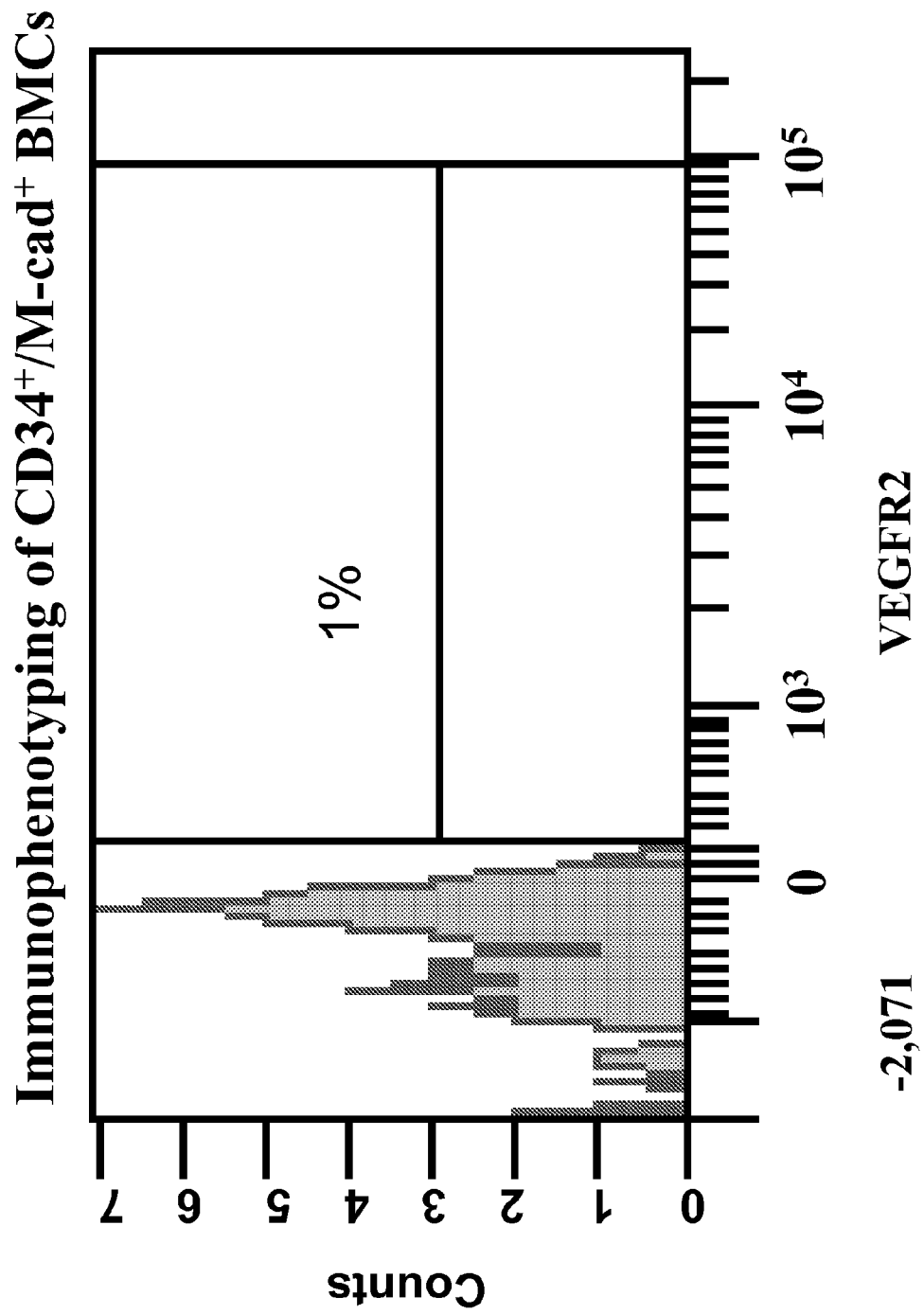
Figure 14:
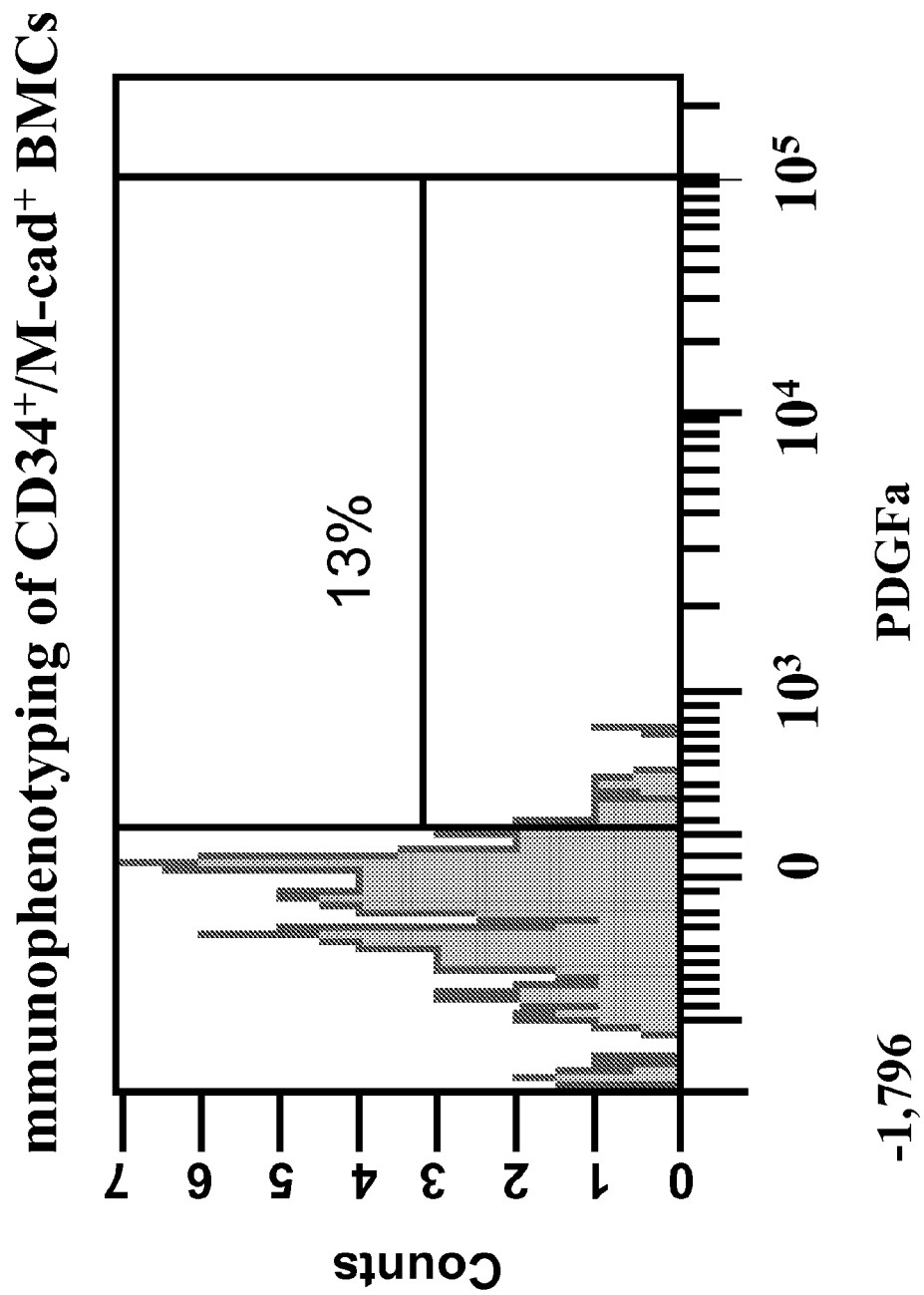
Figure 14:
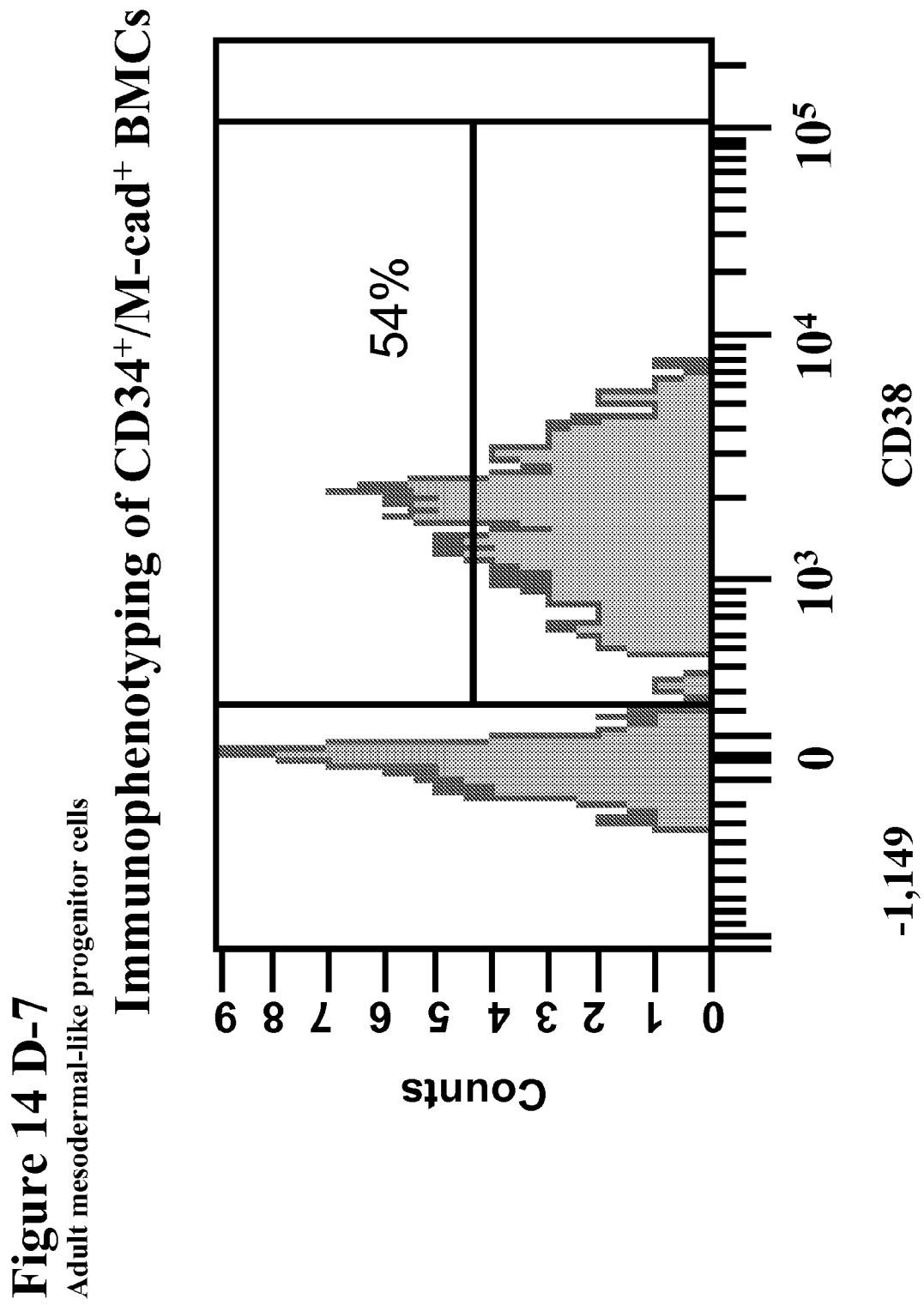
Figure 14:
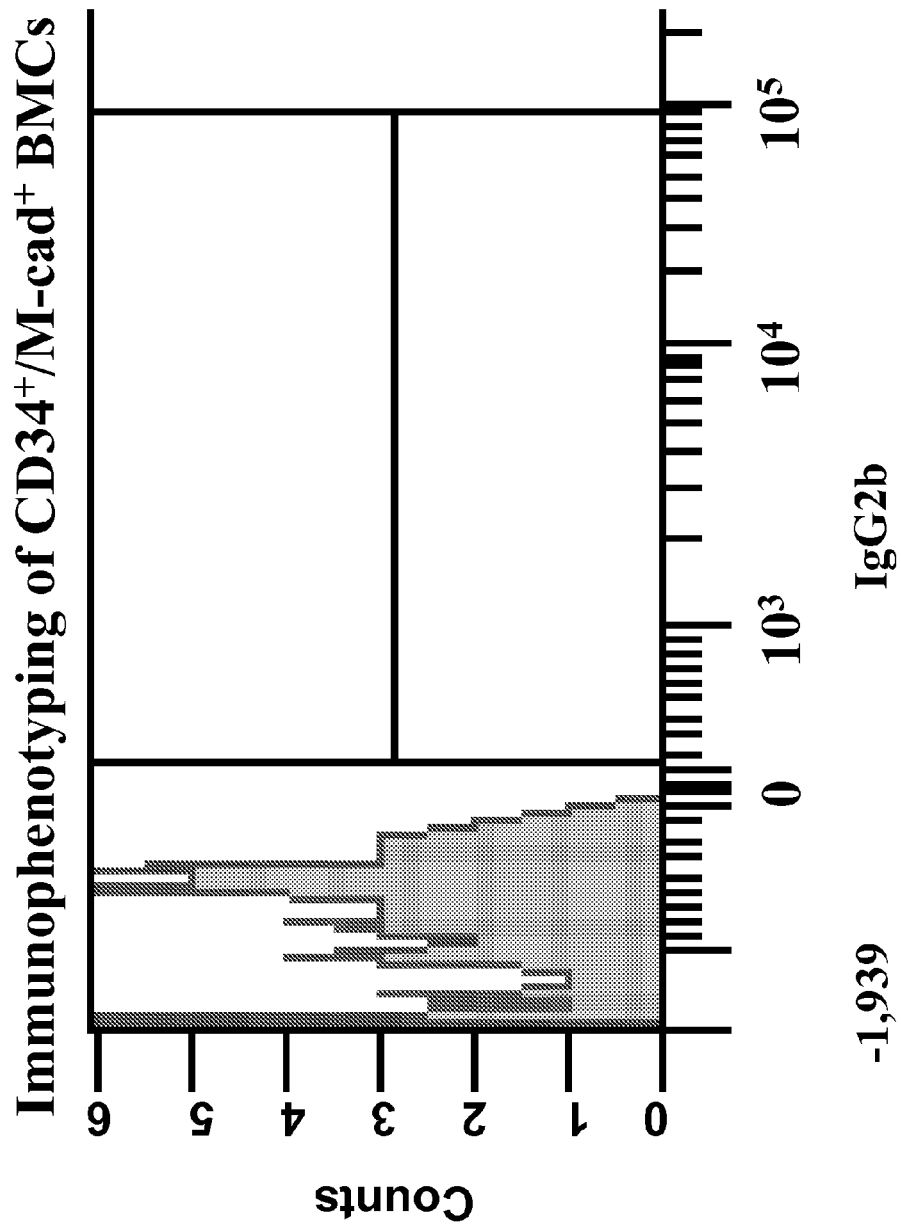
Figure 14:
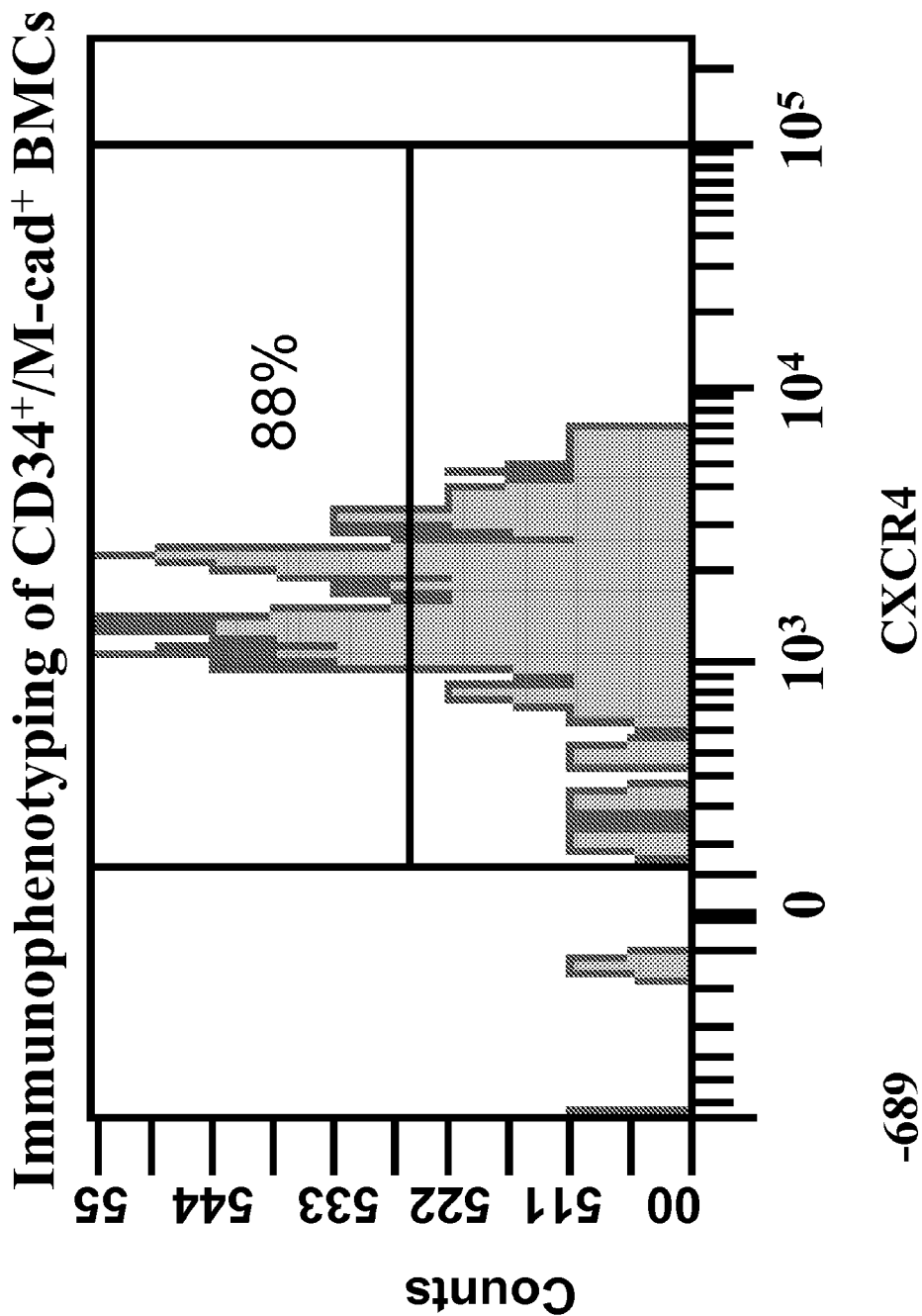
Figure 14:
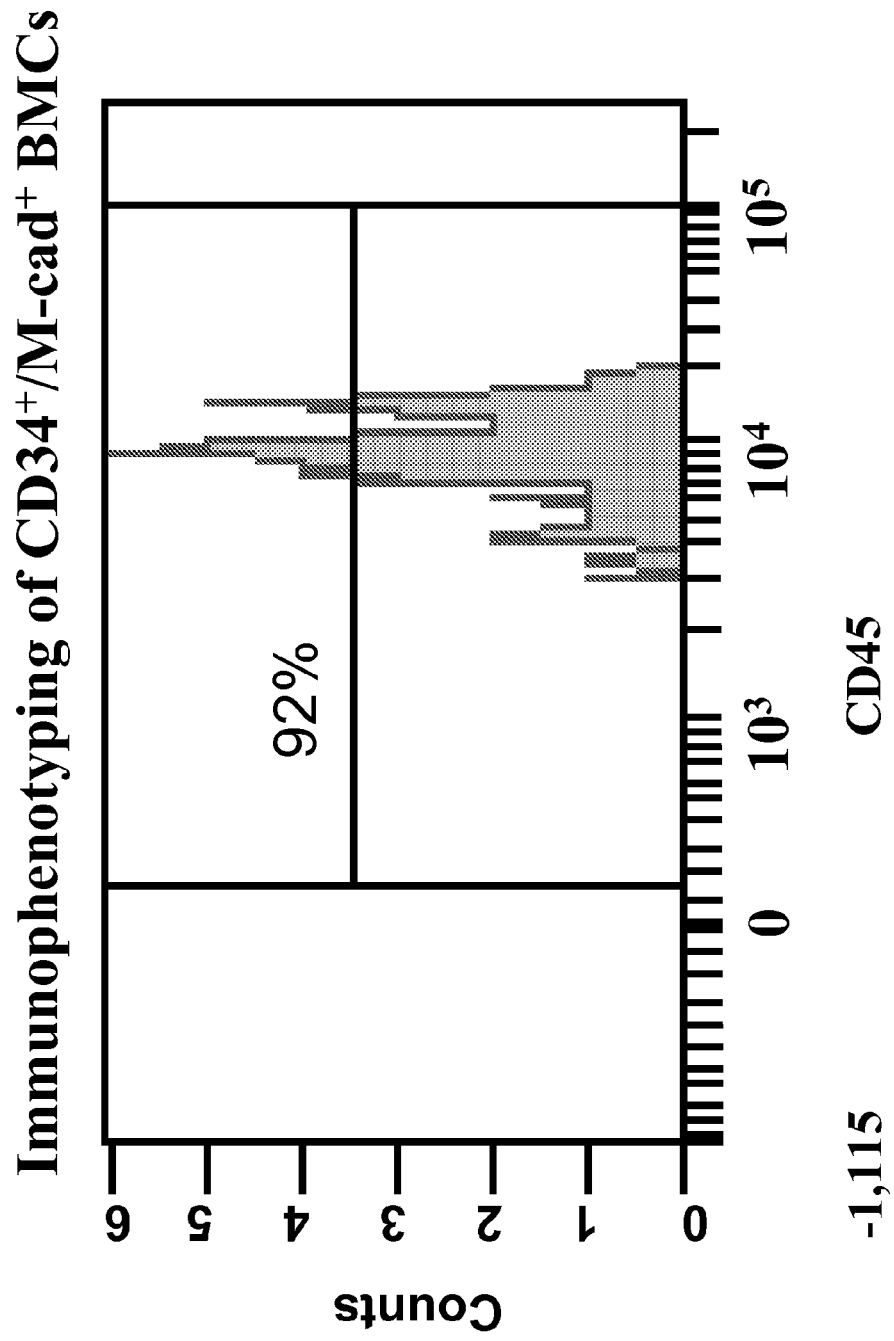
Figure 14:
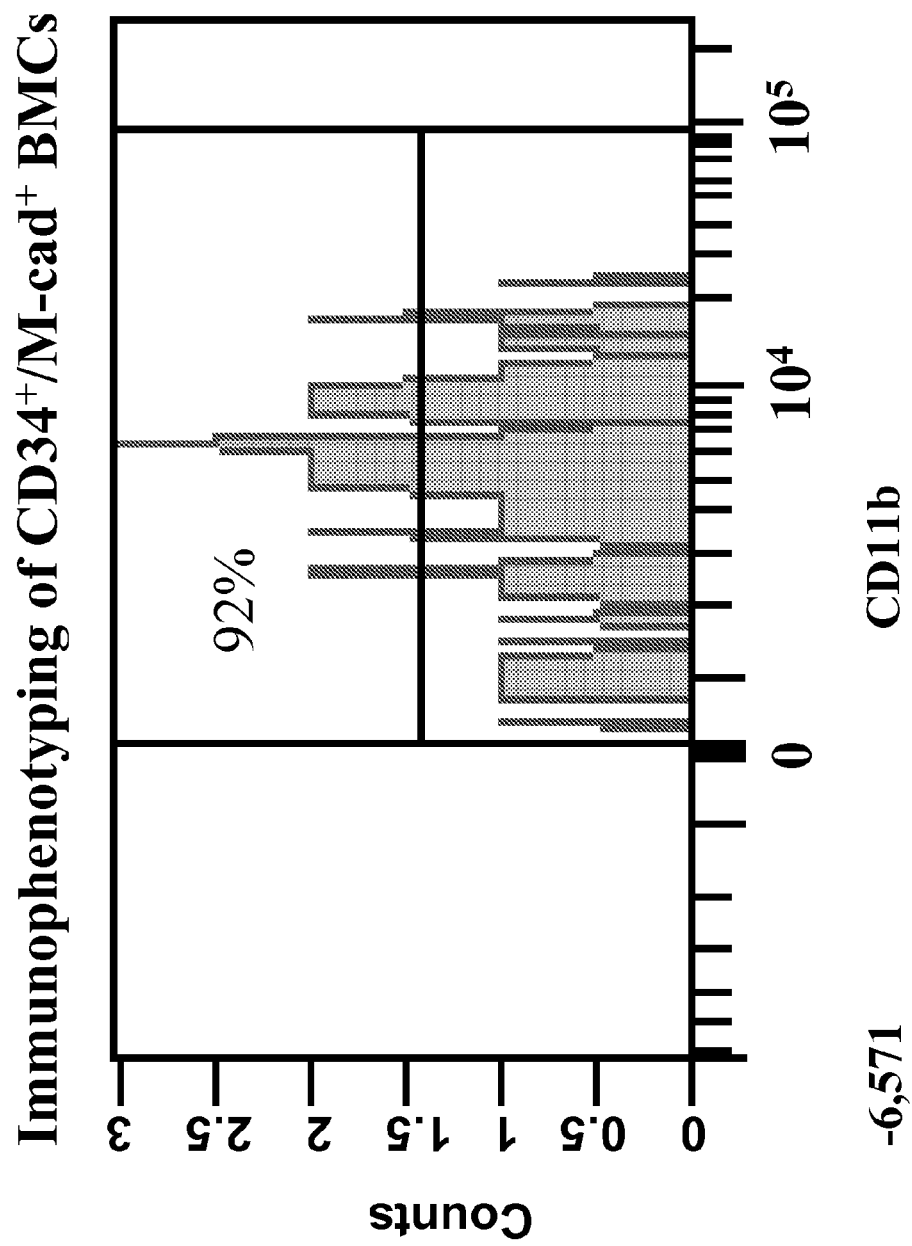
Figure 14:
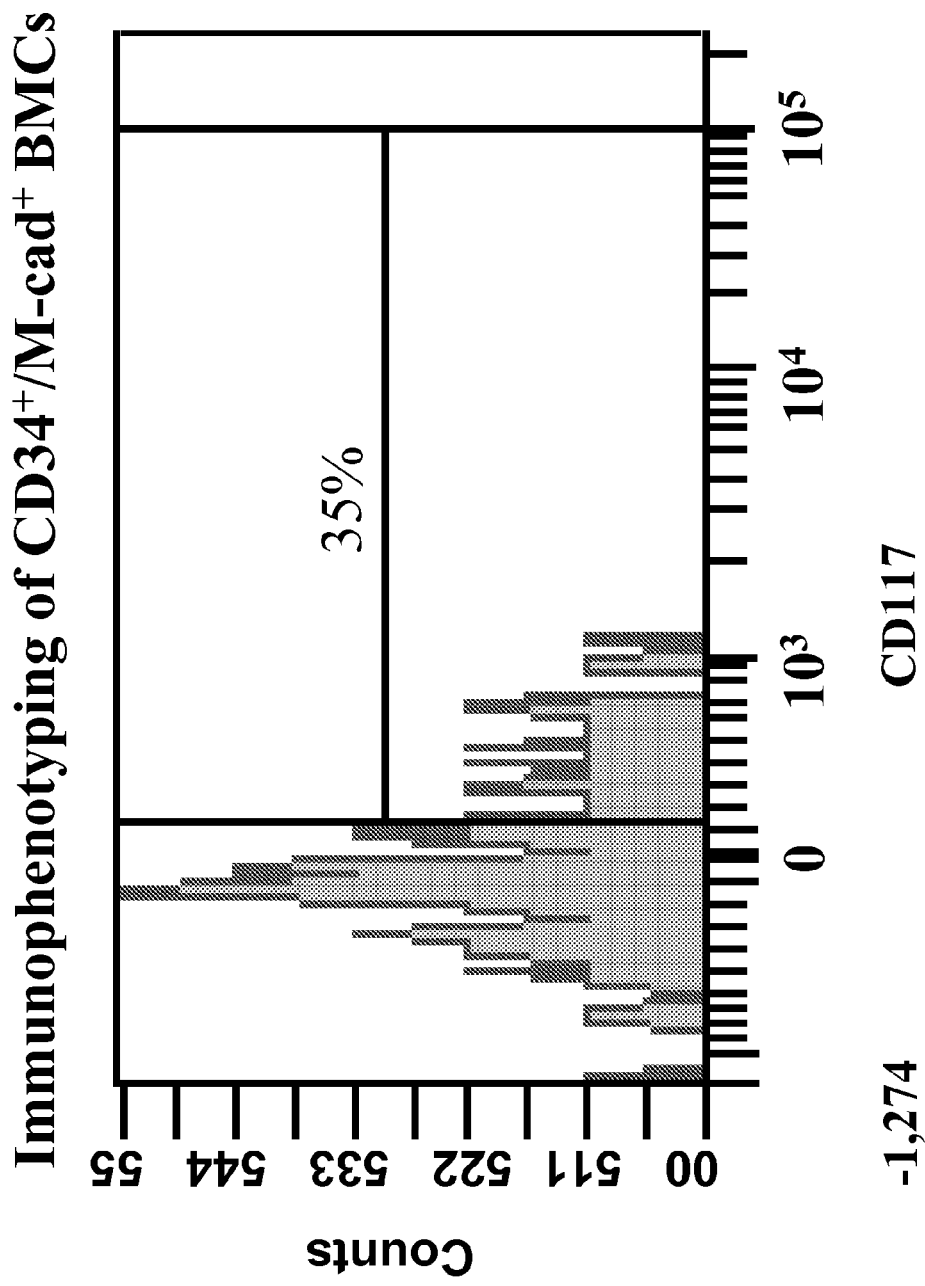
Figure 14:
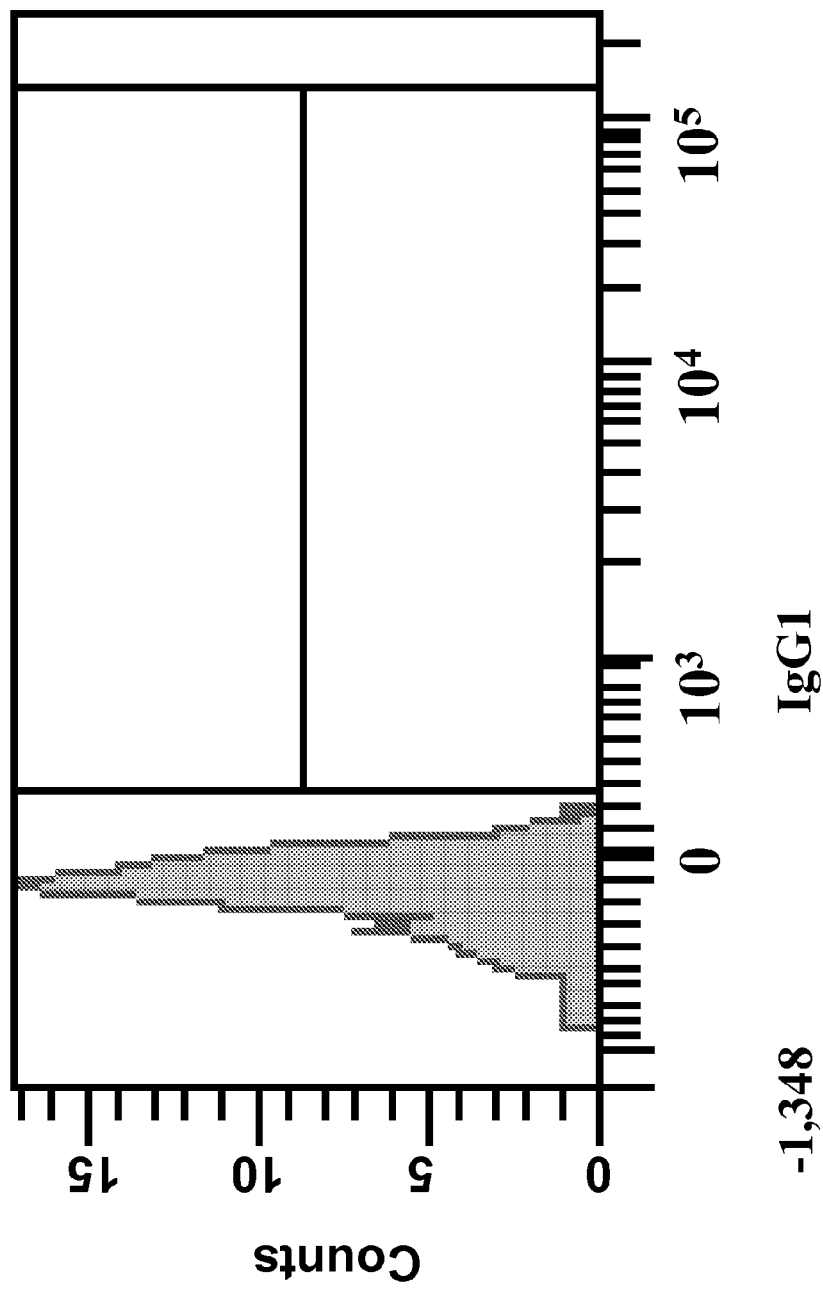
Figure 14:
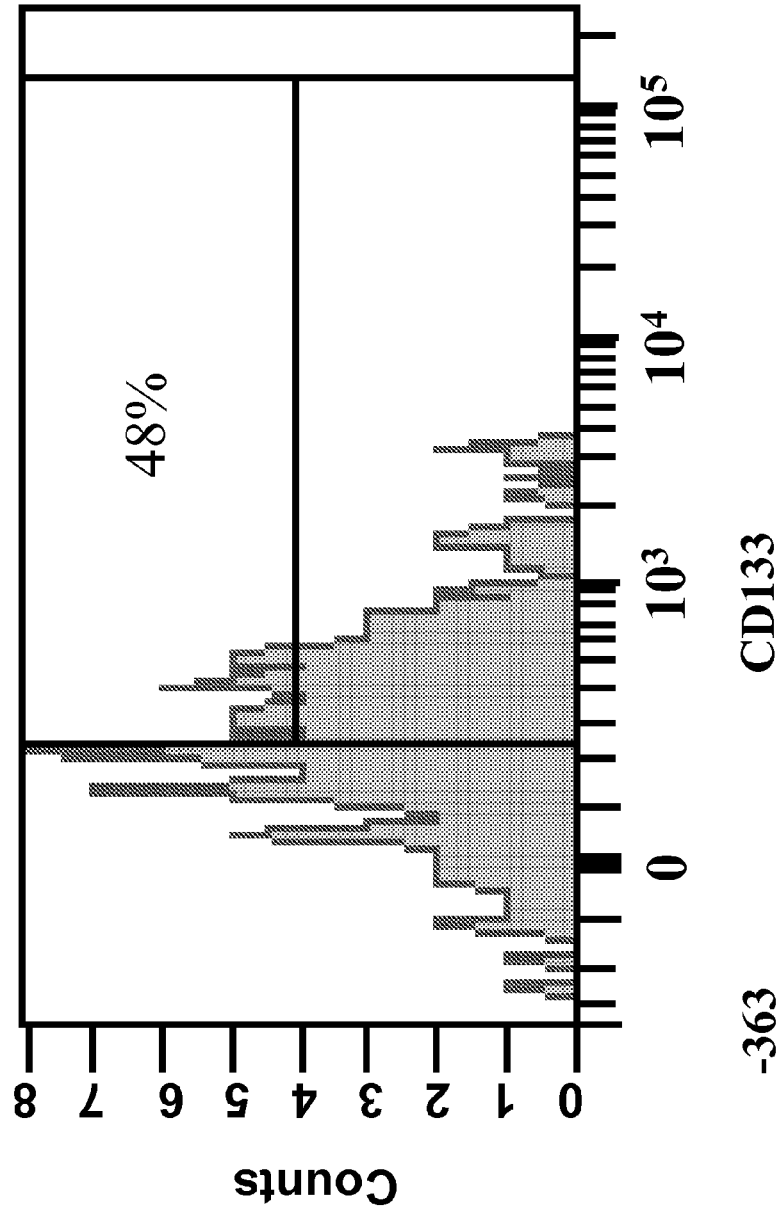
Figure 14:
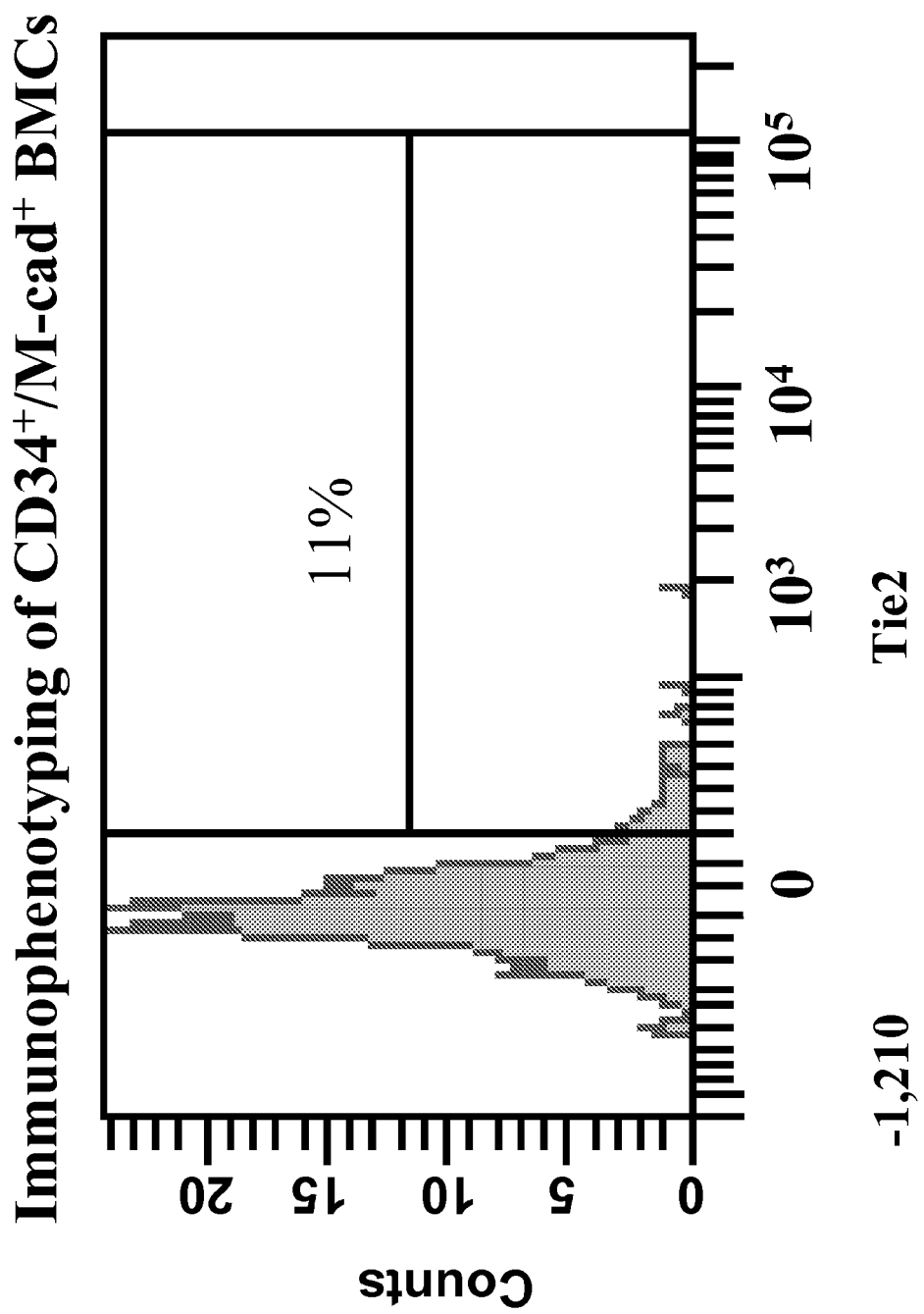
Figure 14:
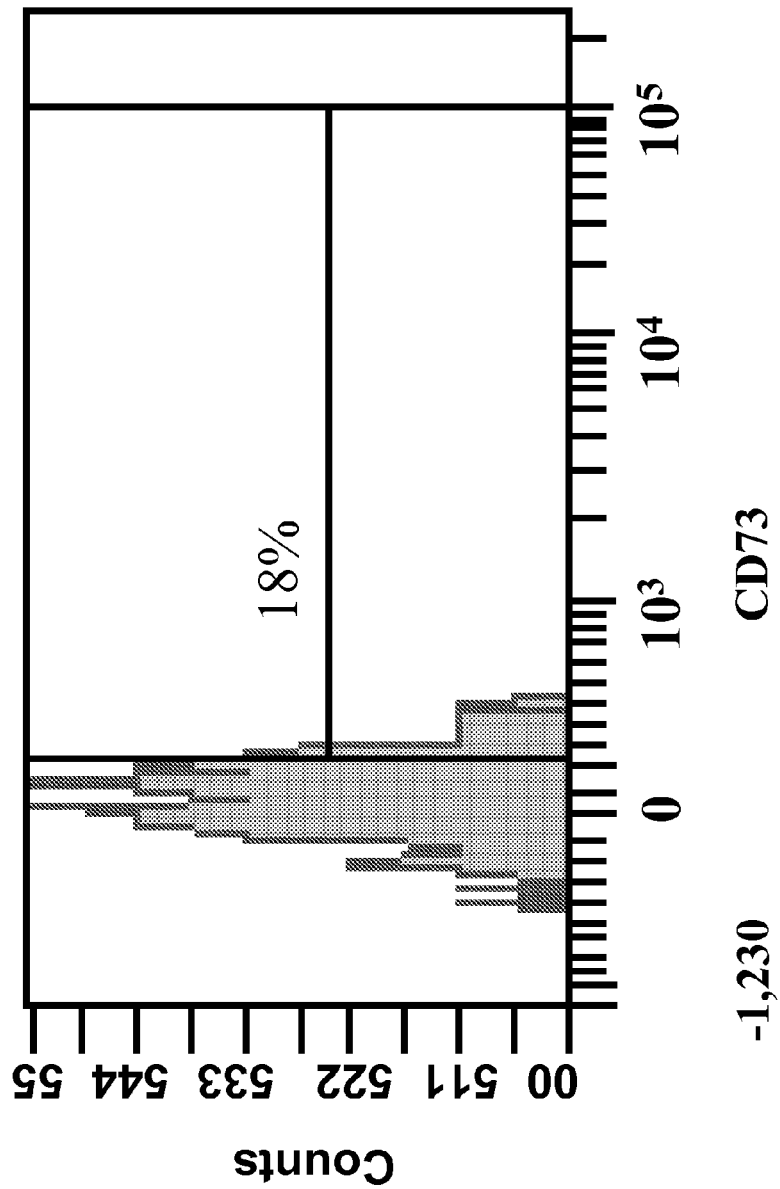

FIG. 14 demonstrates the results of additional immunophenotyping of double positive $CD34^+$/M-cadherin$^+$ cells. The scattergrams A-C, along the top, illustrate the results obtained when $CD34^+$ bone marrow mononuclear cells were stained with a second labeled antibody. The smaller interior boxes were drawn to represent double positive cells, cells that express both CD34 and the ligand of the second antibody. These larger scattergrams illustrate that isolated $CD34^+$ cells did not contain many cells that also stained with labeled mouse IgG2a antibodies (scattergram A: top left interior box) or the anti-mouse 2$^{nd}$ antibody specificity control (scattergram B, top center graph interior box: control) but that some did stain with M-cadherin antibodies (scattergram C, right center graph interior box: double positive $CD34^+$/M-cadherin$^+$ cells). The lower group of smaller graphs (D), illustrate immunophenotyping of these double positive $CD34^+$/M-cadherin$^+$ cells, using labeled antibody selective for, as shown on the top row, left to right: IgG2a, CD31, CD14, Sca-1, VEGFR2, PDGFα, and CD38; as shown on the middle row, left to right: IgG2b, CXCR4, CD45, CD11b, and CD117; as shown on the bottom row, left to right: IgG1, CD133, Tie2, and CD73.

Figure 15:
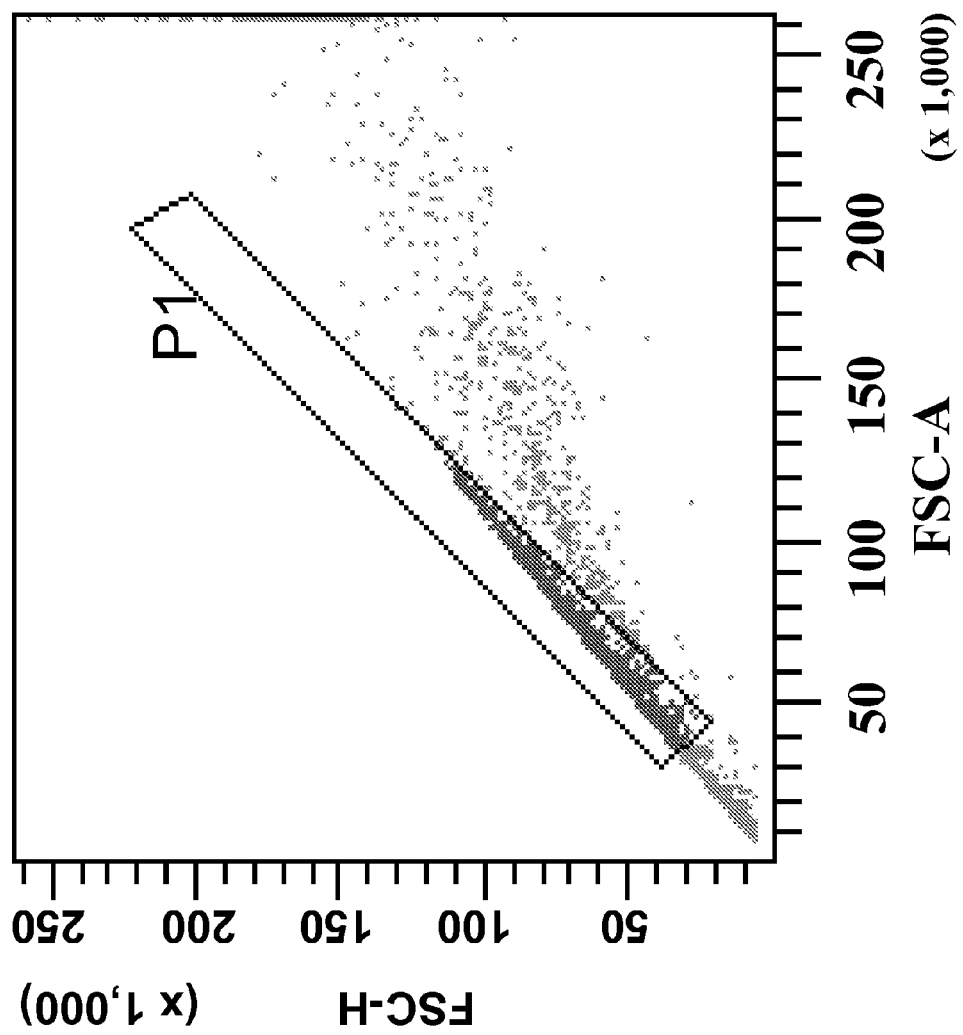
Figure 15:
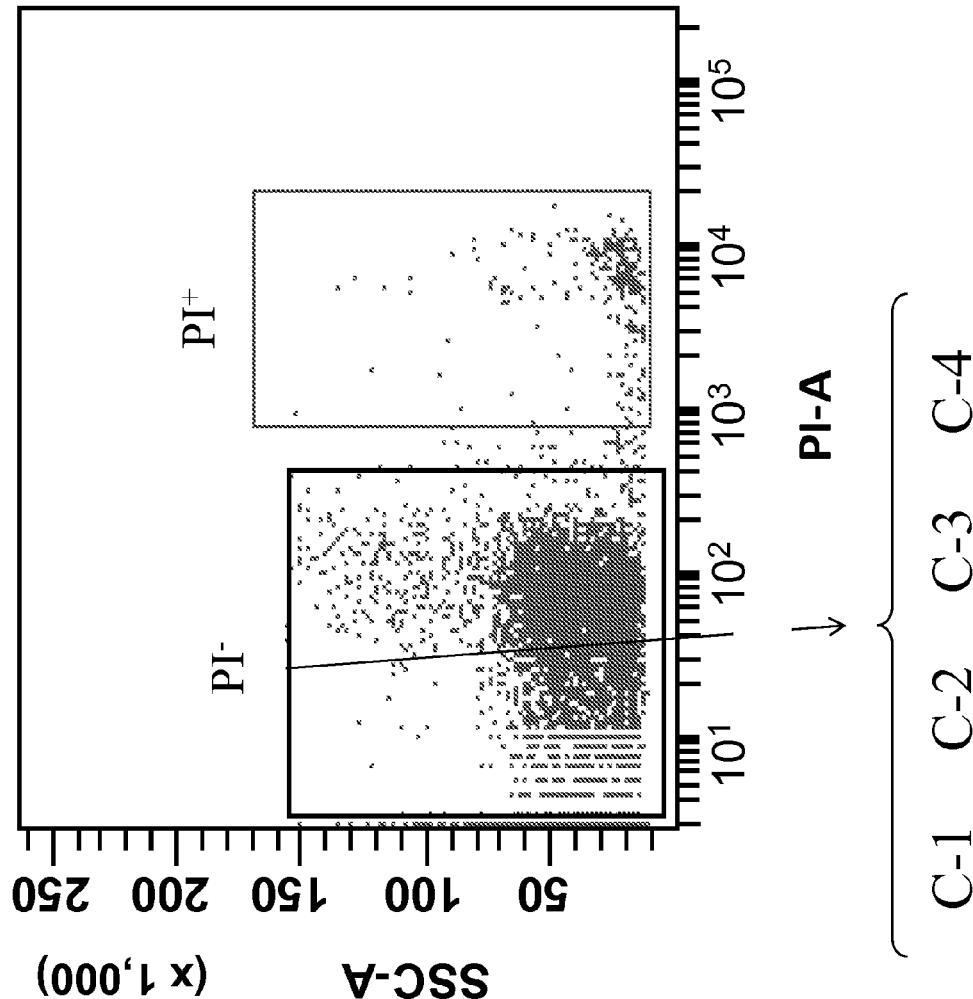
Figure 15:
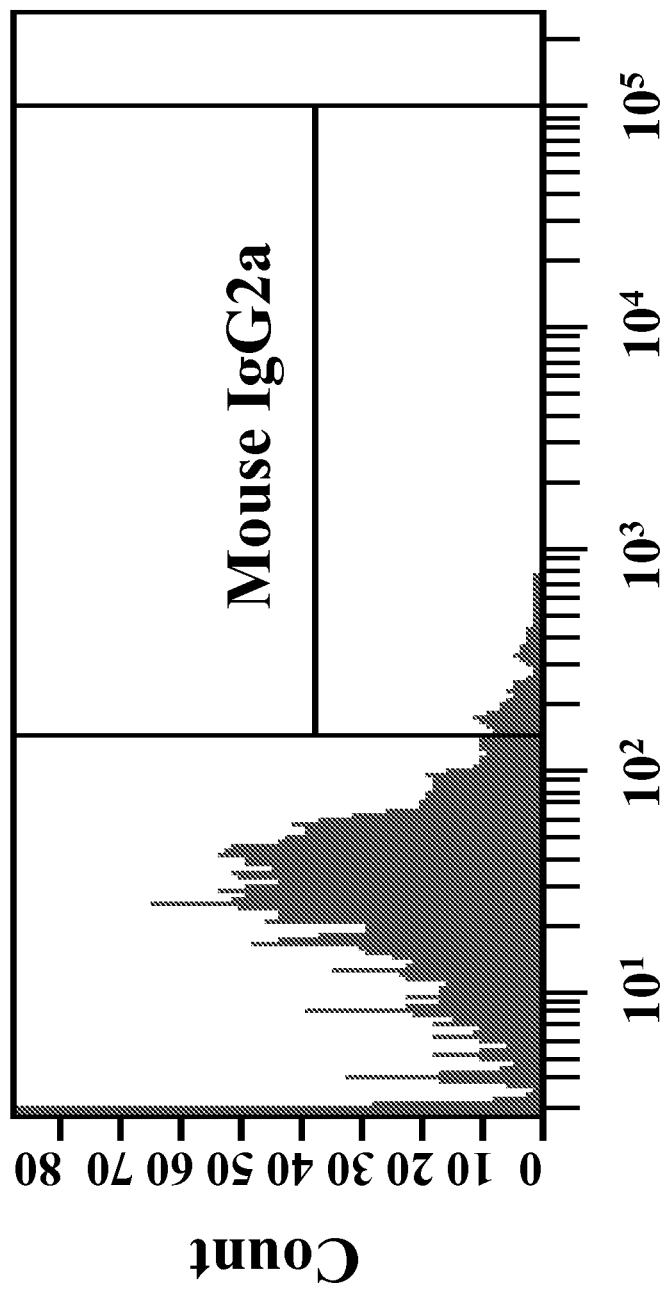
Figure 15:
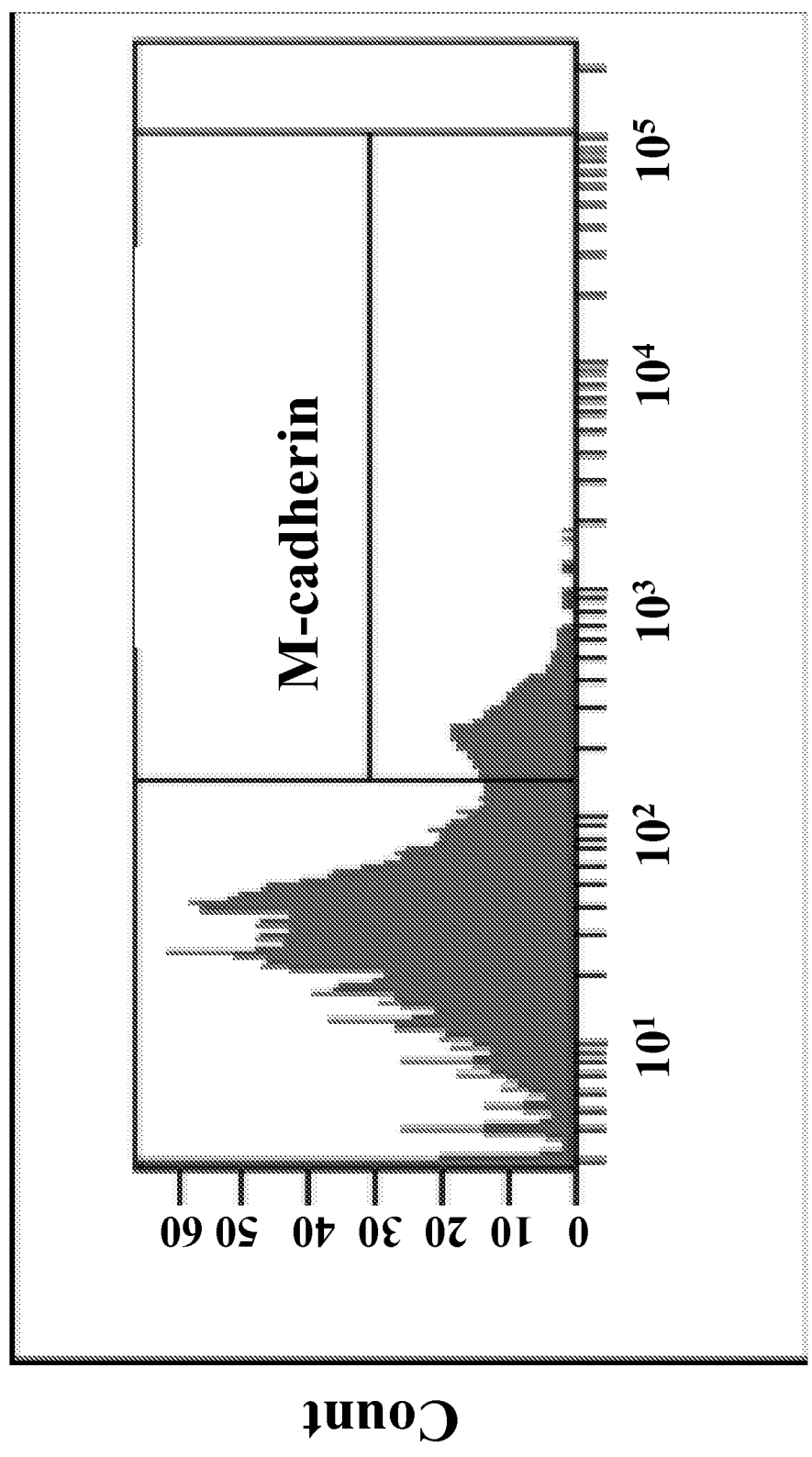
Figure 15:
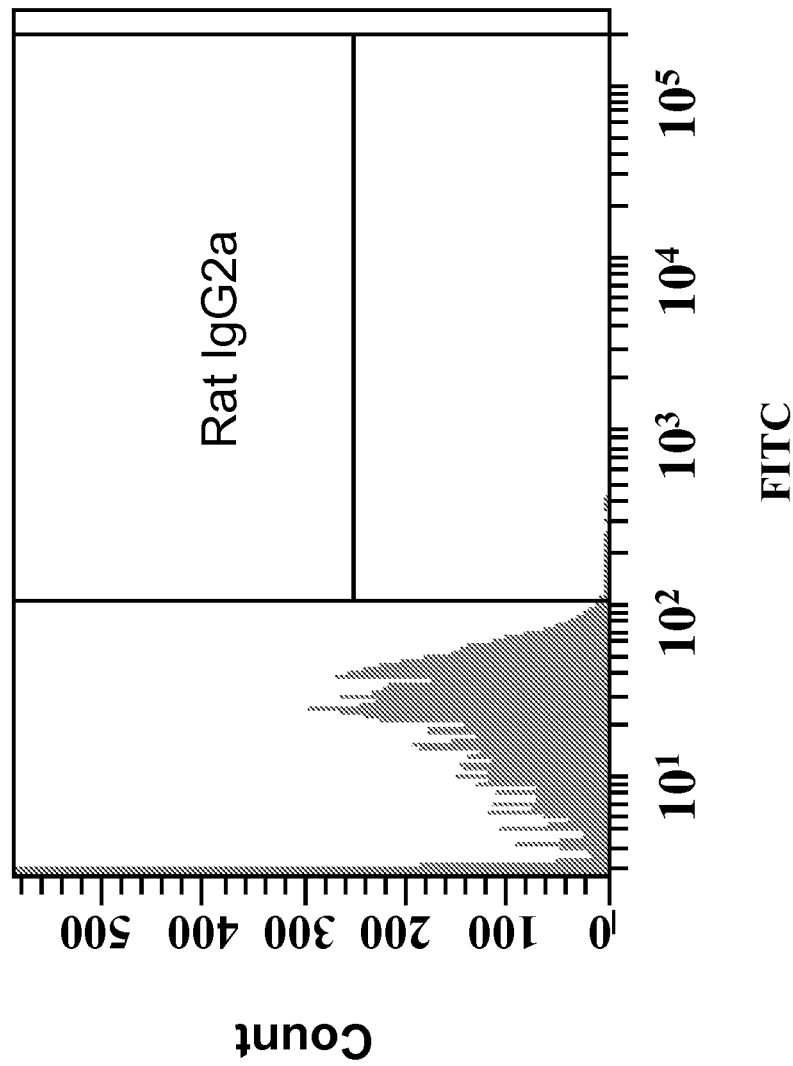
Figure 15:
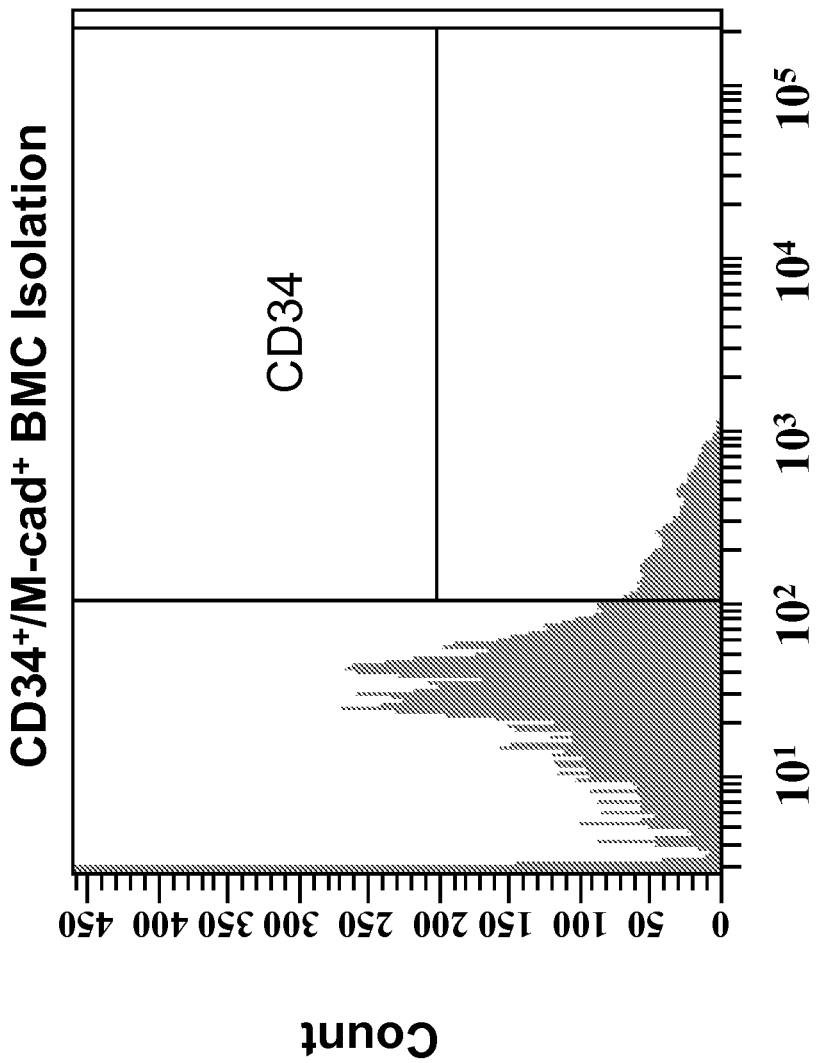

FIG. 15 illustrates a preferred method of identifying $CD34^+$/M-cadherin$^+$ bone marrow progenitor cells. Panel A, Scatter plot of BMCs collected from C57BL6/J mice. The P1 gate was used to discriminate doublets. Panel B, BMC viability. Propidium iodium (PI) was used to exclude dead cells (PI$^+$ cells) from further analysis. Panel C, Identification of M-cadherin+ and CD34+ subsets. Indirect staining with M-cadherin antibody (BD Biosciences, San Diego, Calif.) revealed a small fraction of M-cadherin+ BMCs compared with isotype- and fluorochrome-matched controls. CD34+ BMCs were detected by an FITC-conjugated anti-CD34 monoclonal antibody (eBioscience, San Diego, Calif.).

Figure 16:
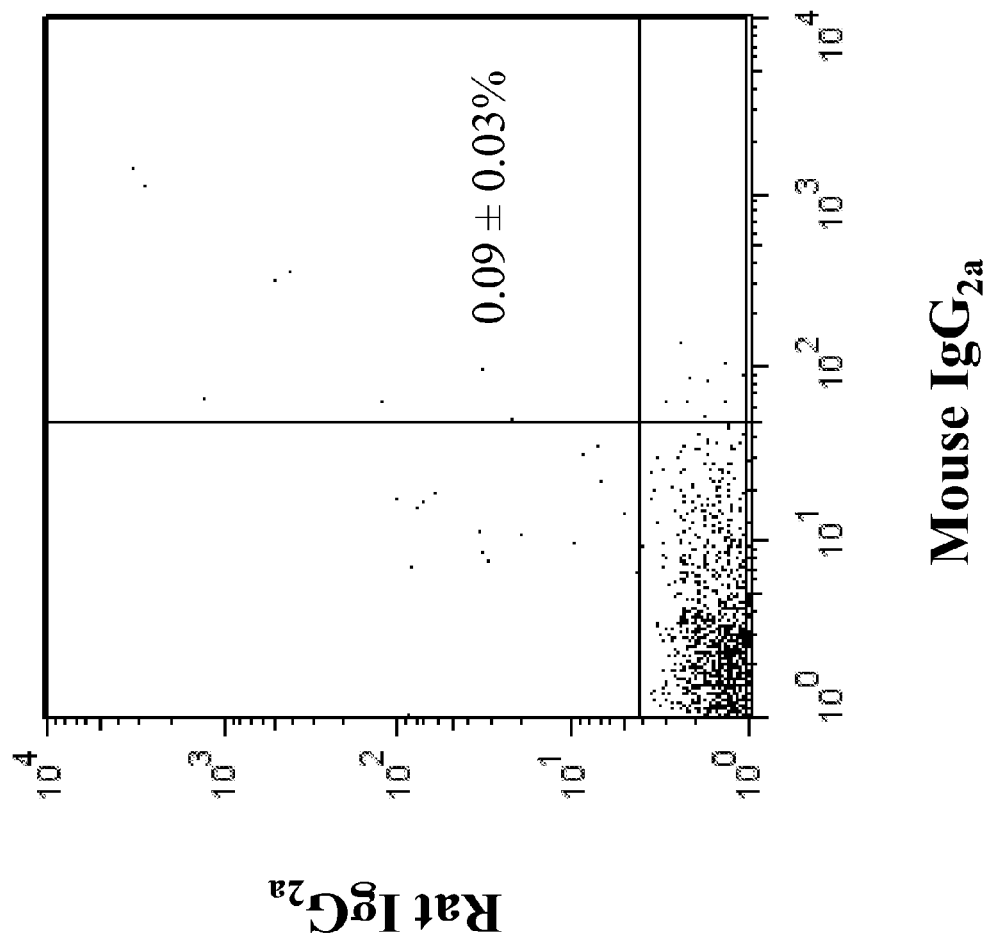
Figure 16:
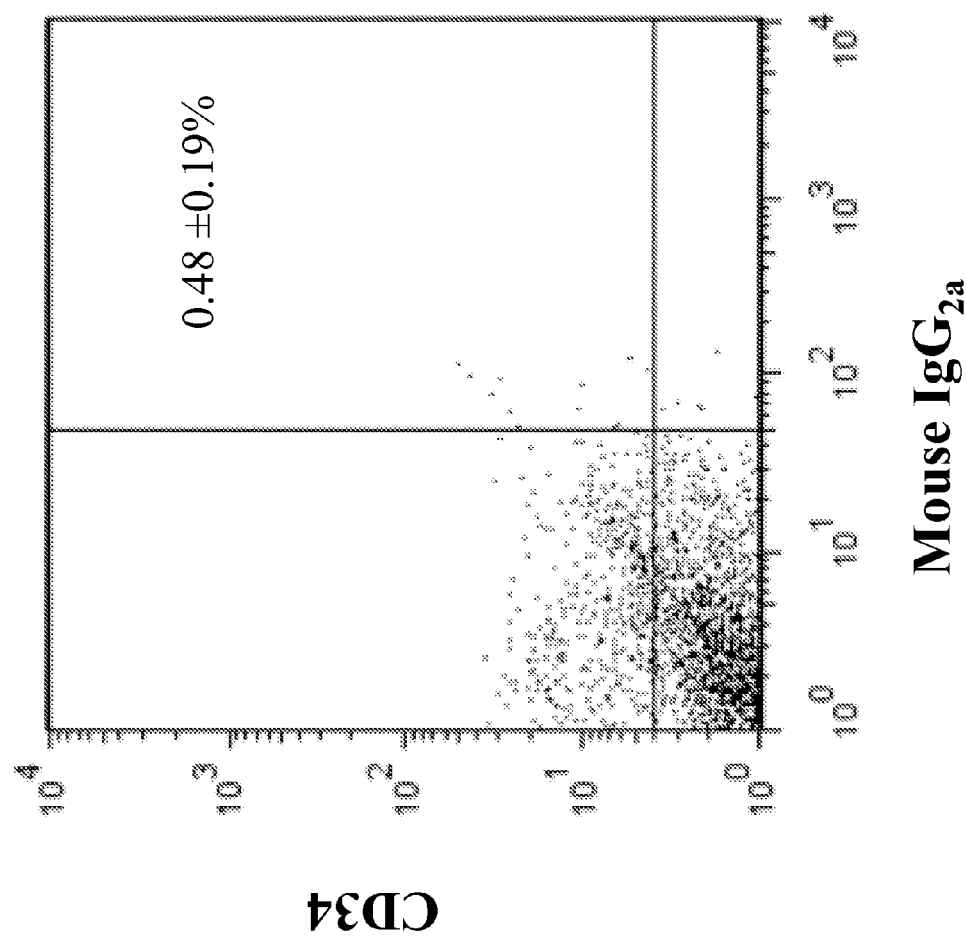
Figure 16:
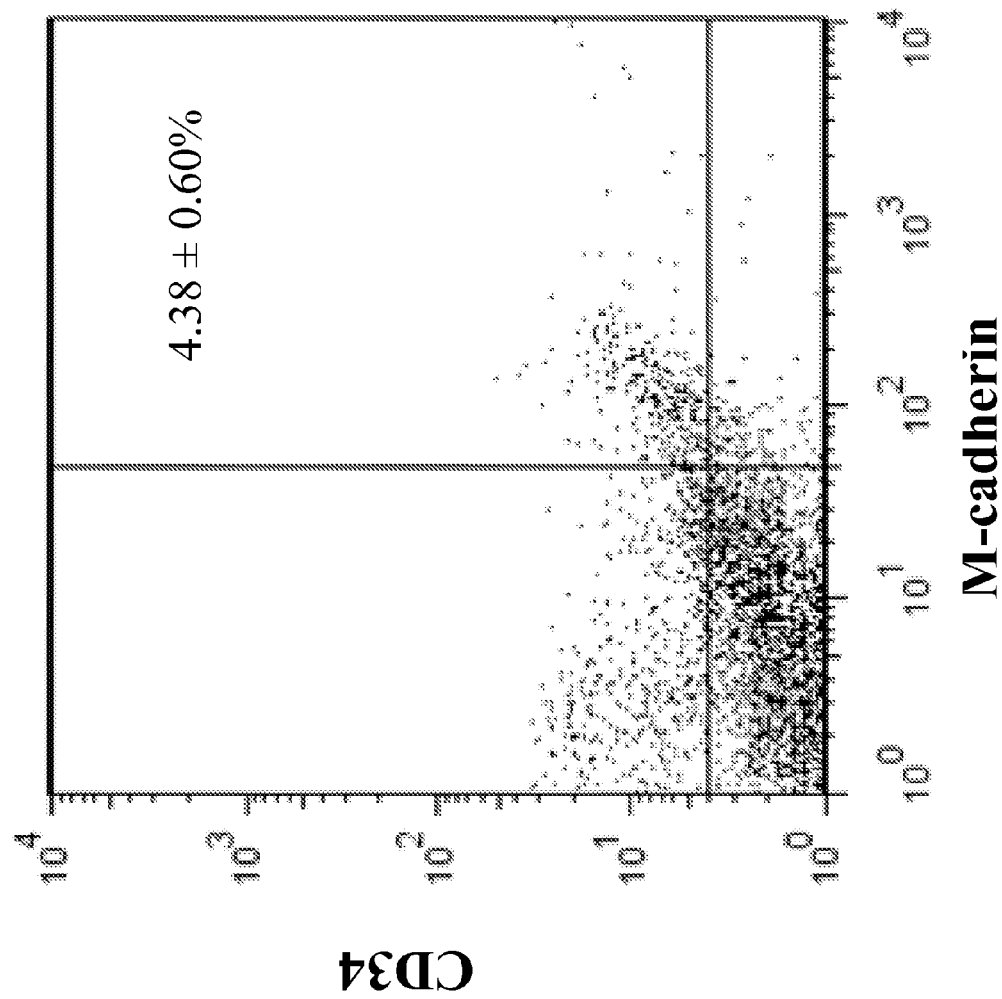
Figure 16:
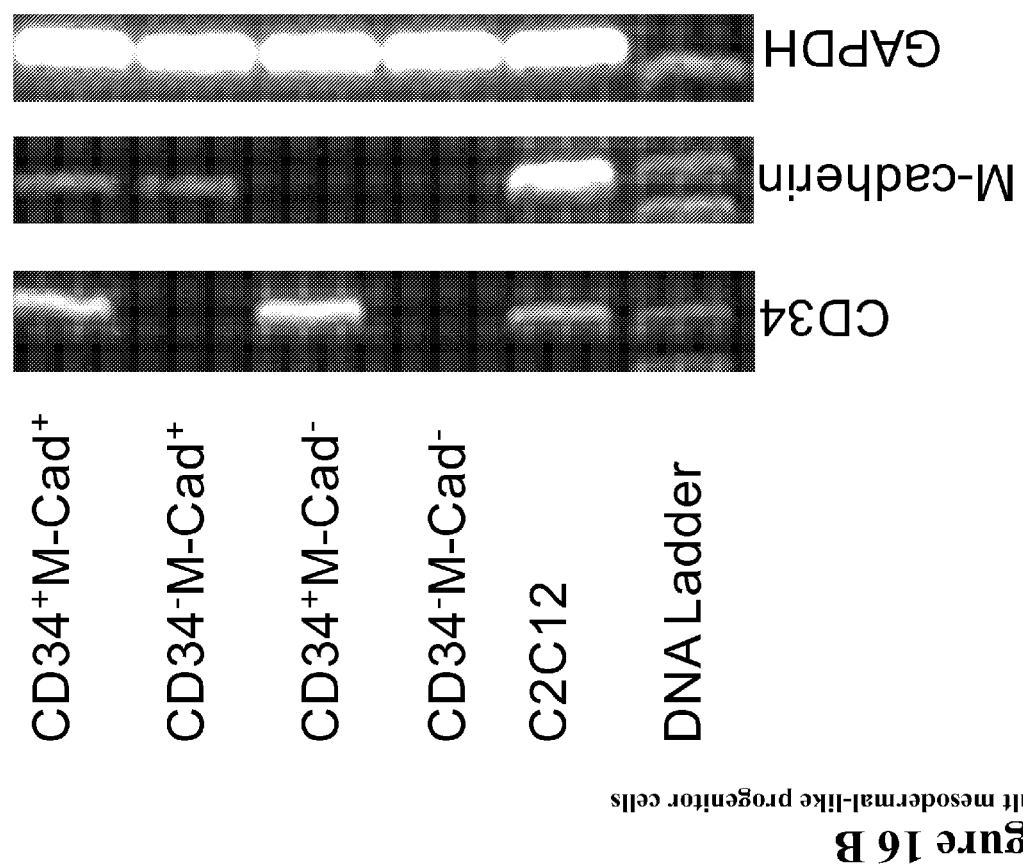
Figure 16:
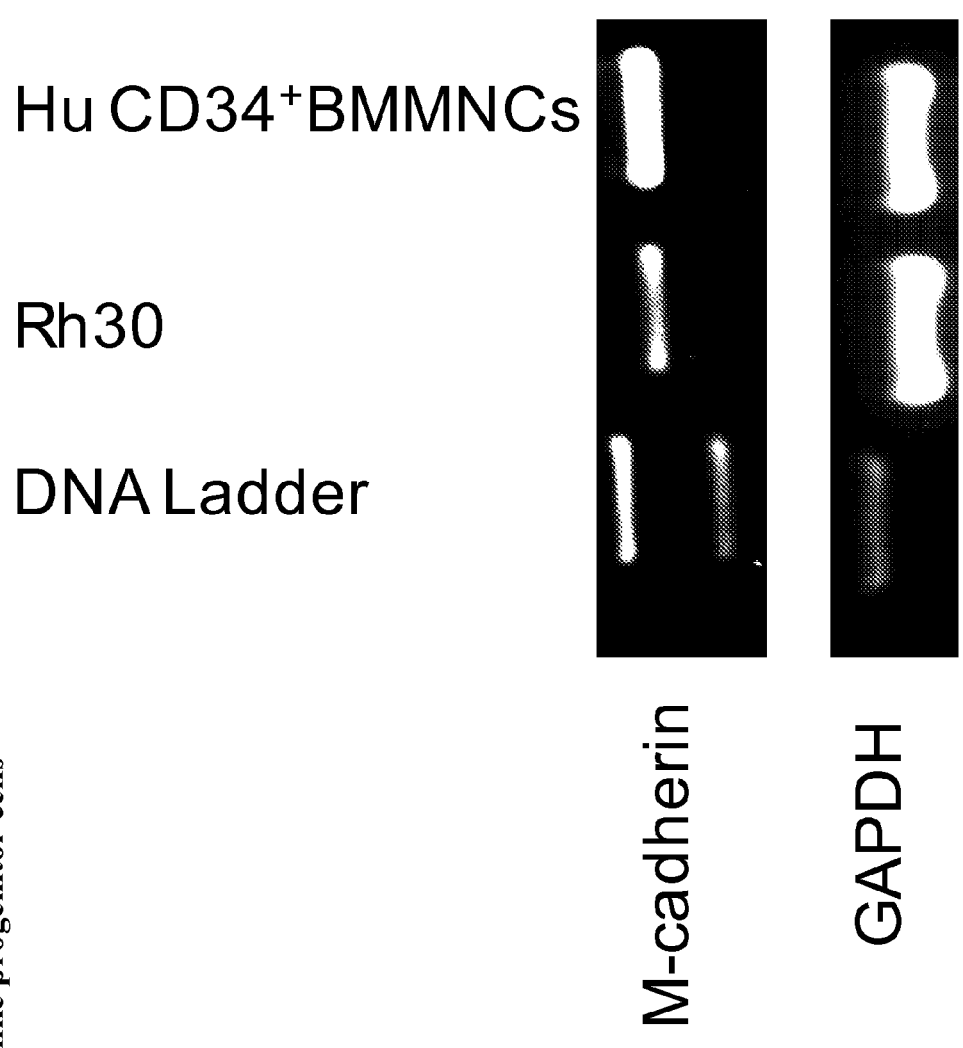

FIG. 16 Panel A illustrates the identification of a CD34+/M-cadherin+ subpopulation from freshly isolated BMCs. Panel B, RT-PCR analysis of CD34 and M-cadherin mRNA in a sorted mouse CD34+/M-cadherin+ BMC subpopulation. Panel C, The detection of M-cadherin mRNA in human CD34+ BMMNCs by RT-PCR.

Figure 17:
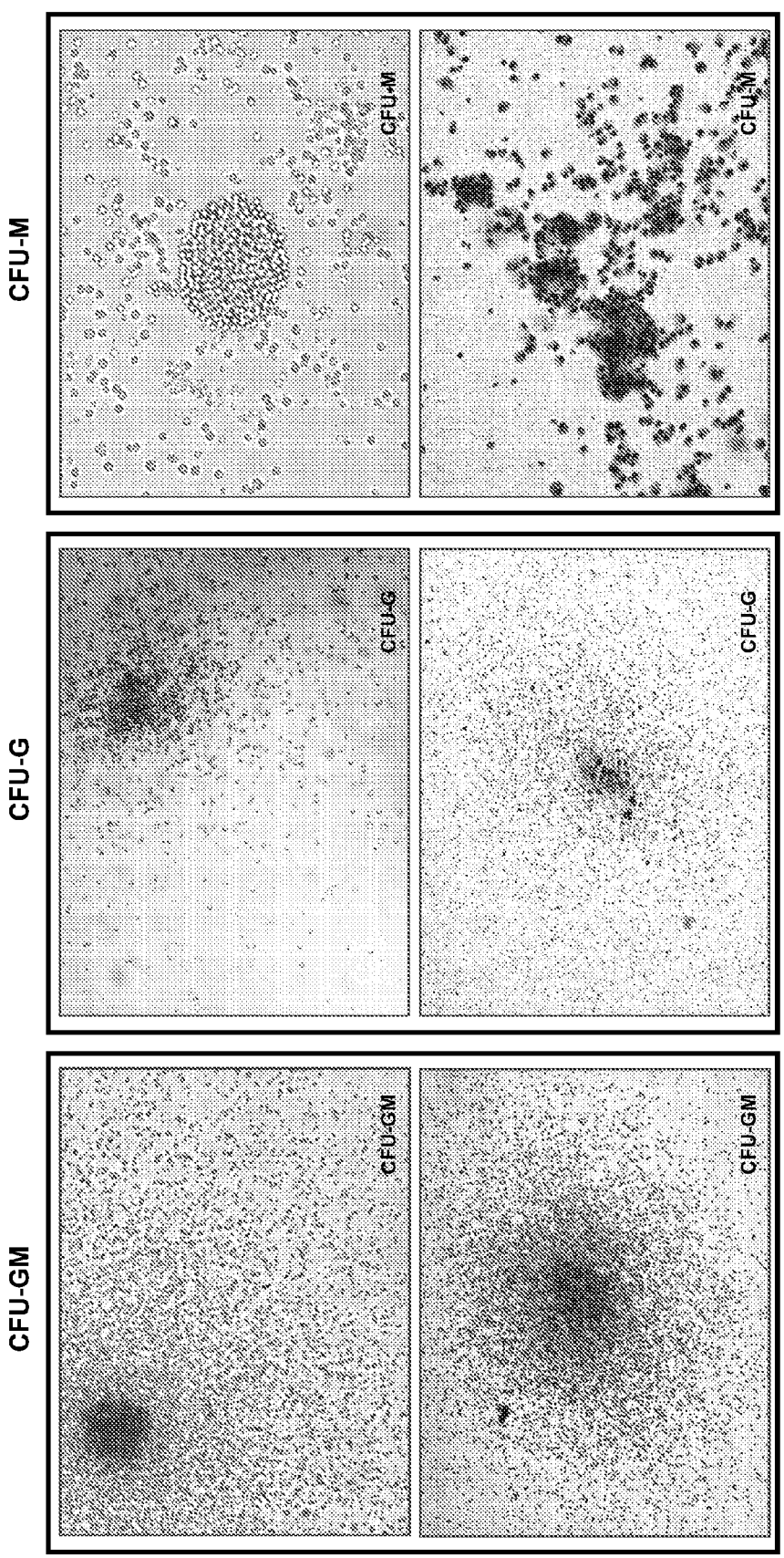

FIG. 17 illustrates that CD34+/M-cad+ BMCs give rise to hematopoietic progenitors. Representative photomicrographs of CD34+/M-cad+ BMCs reveal both granulocytic and monocytic lineages (CFU-GM, CFU-G and CFU-M). Top row, photomicrographs taken under inverted light microscope; bottom row, May-Grünwald-Giemsa stain. Magnification: 40×, CFU-GM and CFU-G; 100×, CFU-M.

Figure 18:
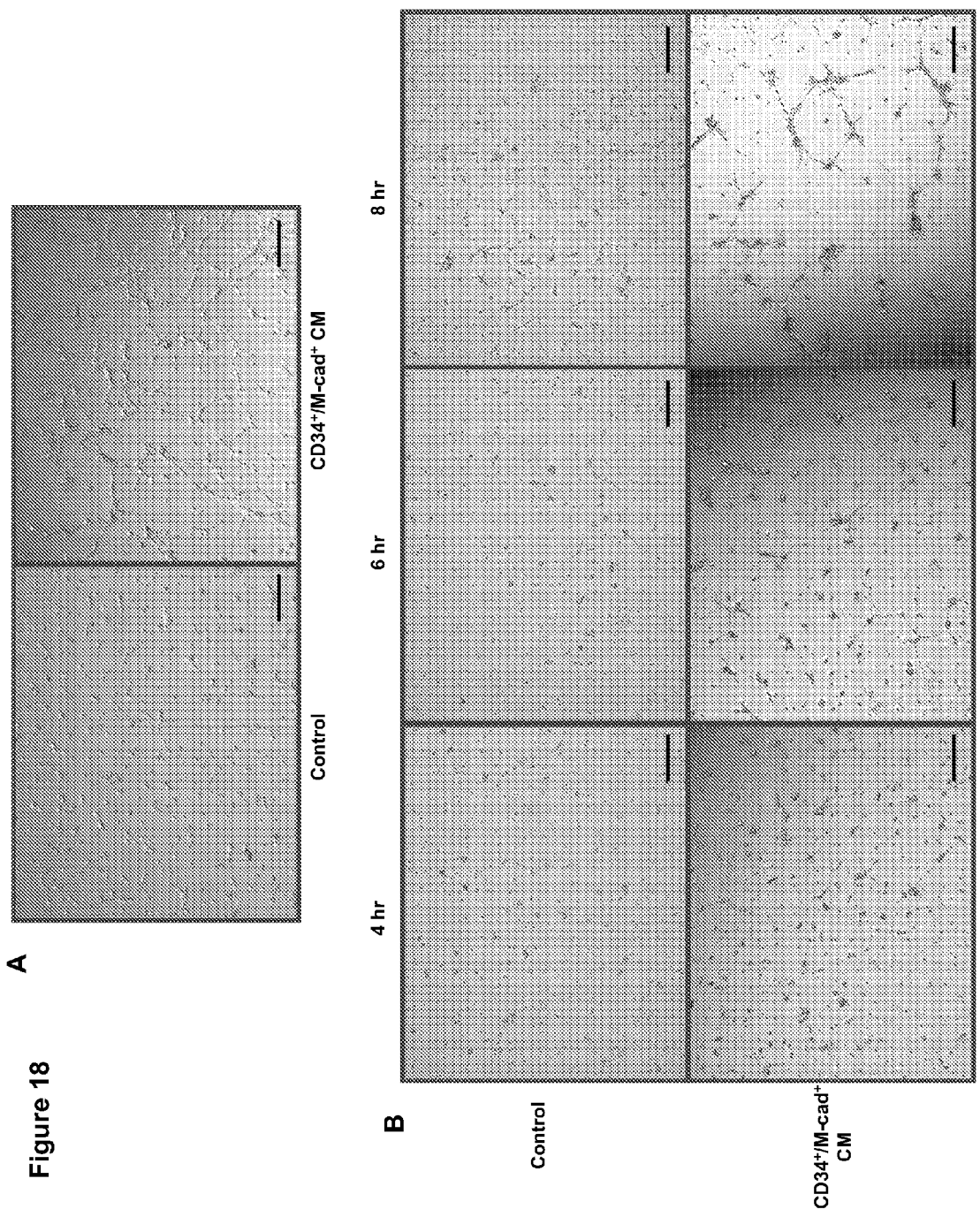

FIG. 18 illustrates CD34+/M-cad+-CM enhanced endothelial cell capillary tube and network formation. Panel A, Serum-starved SVEC4-10 cells were mixed with collagen matrix and incubated under normal (20% $O_2$, 5% $CO_2$, 37° C.) conditions for 3 hrs in CD34+/M-cad+-CM or in control medium. Panel B, Hypoxic (1% $O_2$, 5% $CO_2$, 37° C.), serum-starved SVEC4-10 cells were mixed with collagen matrix and incubated with CD34+/M-cad+-CM or control medium for up to 8 hrs. Timed-incubation revealed that capillary-like tube formation was greater in the CD34+/M-cad+-CM-treated group than in the control-medium-treated group. Scale bar=50 μm.

Figure 19:
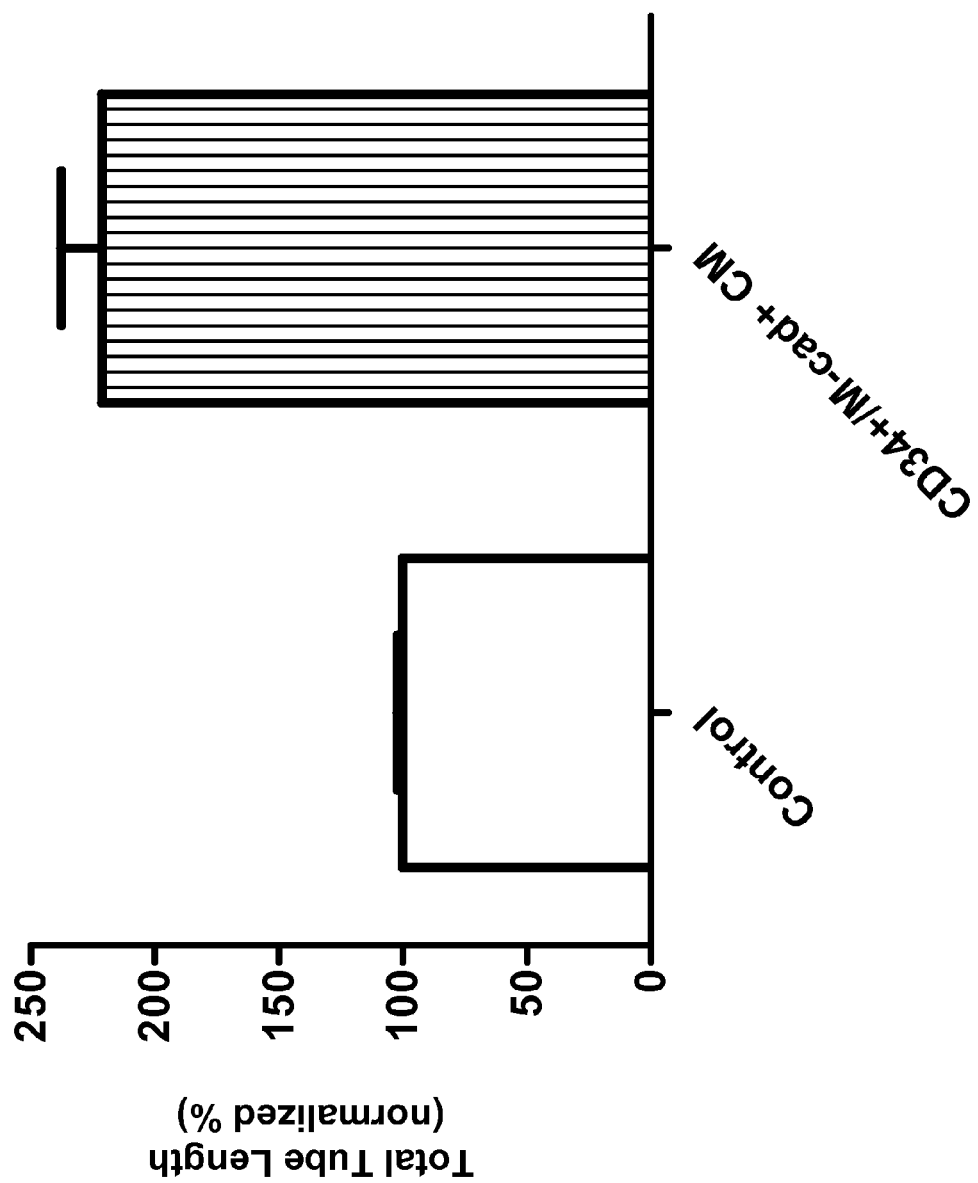
Figure 19:
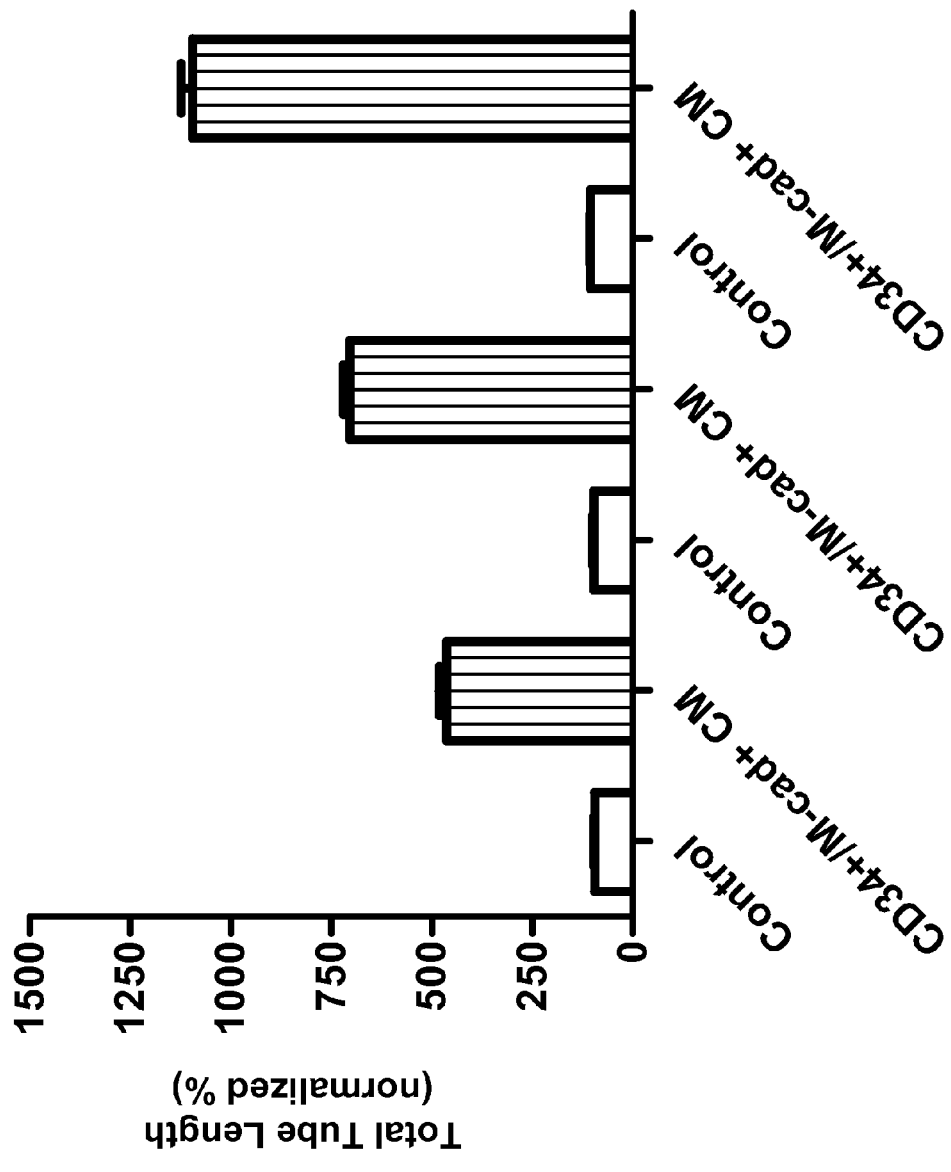

FIG. 19, panel A is a quantification of tube length formation in SVEC4-10 cells after incubation with control medium or CD34+/M-cad+-CM under normoxic conditions (n=3, ***$P<0.001$). Panel B, Quantification of tube length formation in SVEC4-10 cells at 4, 6 and 8 hours after incubation with control medium or CD34+/M-cad+-CM, under hypoxic conditions (n=3, *$P<0.05$, **$P<0.01$). Tube length was measured as μm/mm.$^2$ Results were normalized as compared to control (set at 100%) and reported as mean±SEM.

Figure 20:
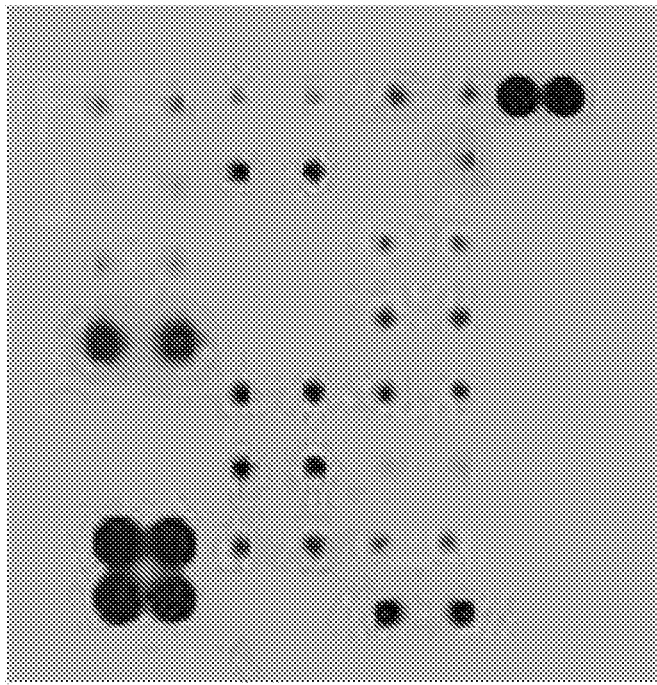
Figure 20:
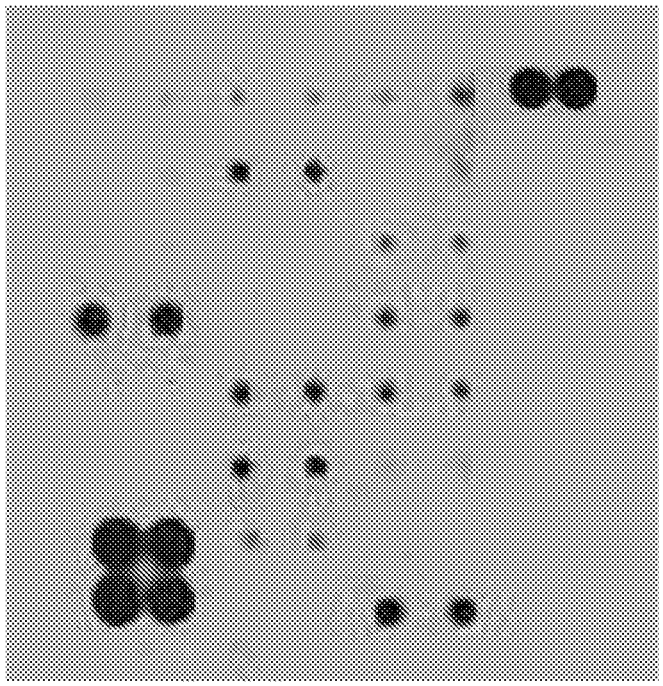

FIG. 20, illustrates increased cytokine secretion in CD34+/M-cad+ BMCs vs unselected BMCs. Panel A, Representative membranes and corresponding analysis key for CM from each indicated cell population. Panel B, CM from CD34+/M-cad+ BMCs showed significant secretion levels of key stimulatory cytokines compared with CM from unselected BMCs. The cytokine arrays (n=3) were quantified by using the S.09 analysis tool (RayBiotech, Inc). Data are expressed as mean±SEM. *$P<0.05$, CD34+/M-cad+ BMC vs. unselected BMCs.

DETAILED DESCRIPTION

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise The term "about" when referring to a numerical value or range is intended to include larger or smaller values resulting from experimental error that can occur when taking measurements. Such measurement deviations are usually within plus or minus 10 percent of the stated numerical value.

Any use of the term "optionally" with respect to any element of a claim is intended to mean that the subject element is required, or alternatively, is not required. Both alternatives are intended to be within the scope of the claim.

As used herein, and unless otherwise indicated, the terms "treat", "treating", and "treatment" contemplate an action that occurs while a patient is suffering from ischemia that reduces the severity of one or more symptoms or effects of ischemia, or a related disease or disorder. Where the context allows, the terms "treat", "treating", and "treatment" also refers to actions taken toward ensuring that individuals at increased risk of ischemia are able to receive appropriate neurosurgical or other medical intervention prior to onset of ischemia. As used herein, and unless otherwise indicated, the terms "prevent", "preventing", and "prevention" contemplate an action that occurs before a patient begins to suffer from ischemia, that delays the onset of, and/or inhibits or reduces the severity of, ischemia. As used herein, and unless otherwise indicated, the terms "manage", "managing", and "management" encompass preventing, delaying, or reducing the severity of a recurrence of ischemia in a patient who has already suffered from such a disease or condition. The terms encompass modulating the threshold, development, and/or duration of the ischemia or changing how a patient responds to the ischemia.

As used herein, and unless otherwise specified, a "therapeutically effective amount" of a compound or composition is an amount sufficient to provide any therapeutic benefit in the treatment or management of ischemia or to delay or minimize one or more symptoms associated with ischemia. A therapeutically effective amount of a compound or composition means an amount of the compound or composition, alone or in combination with one or more other therapies and/or therapeutic agents that provides any therapeutic benefit in the treatment or management of ischemia, or related diseases or disorders. The term "therapeutically effective amount" can encompass an amount that alleviates ischemia, improves or reduces ischemia, improves overall therapy, or enhances the therapeutic efficacy of another therapeutic agent.

As used herein, and unless otherwise specified, a "prophylactically effective amount" of a compound or composition is an amount sufficient to prevent or delay the onset of ischemia, or one or more symptoms associated with ischemia, or prevent or delay its recurrence. A prophylactically effective amount of a compound or composition means an amount of the compound or composition, alone or in combination with one or more other treatment and/or prophylactic agent that provides a prophylactic benefit in the prevention of ischemia. The term "prophylactically effective amount" can encompass an amount that prevents ischemia, improves overall prophylaxis, or enhances the prophylactic efficacy of another prophylactic agent.

Temperatures, ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range, as if each numerical value and sub-range is explicitly recited. For example, a dose comprising $10^2$-$10^{10}$ cells should be interpreted to include not only the express limits of $10^2$ and $10^{10}$, but also to include every intervening value such as $10^5$, $10^8$, and all sub-ranges such as $10^4$-$10^6$, and so forth.

The section headings used herein are for organizational purposes only and are not to be construed as limiting the subject matter described.

The inventors have discovered that the administration of mesodermal-like precursor cells bearing both the CD34 and M-cadherin cell surface markers, directly into an ischemic tissue or limb effectively prevented or reversed many of the symptoms of ischemia. The term "mesodermal-like" generally refers to adult bone marrow cells with broad differentiation potential similar to the mesodermal cell layer of early embryogenesis. Such cells have myoendothelial regenerative potential (i.e., the potential to develop diverse lineages including endothelial, smooth muscle, and skeletal muscle cells, and have many cell surface markers in common with mesodermal cell lineages. For the purposes of this disclosure, mesodermal-like cells are multipotent cells in the adult bone marrow that express both CD34 and M-cadherin and can develop into mesenchymal cell lineages, including skeletal and smooth muscle cells, and endothelial progenitor cells/endothelial cells, thereby giving rise to new blood vessels, for example.

Methods and compositions for the treatment or prevention of ischemic and vascular disorders, which are disclosed herein, are based on that discovery. The compositions comprise an effective amount of mesodermal-like precursor cells. These cells are identified by the co-expression of both CD34 and M-cadherin (CD34$^+$/M-cadherin$^+$) cell markers and are obtained from, for example, autologous or heterologous bone marrow cells or bone marrow cells that have been expanded in vitro, stem cells, embryonic endothelial cells or muscle cells, embryonic stem cell lines and hematopoietic stem cells, or any other suitable source. The cells are enriched using fluorescence activated cell sorter (FACS™), magnetic bead based systems, magnetic activated cell sorter (MACS™) or any other known cell enrichment, purification and isolation technique that is suitable for this purpose.

Overview of CD34 Marker Protein

CD34 is a cell surface glycoprotein molecule present on certain cells within the body. CD34 is also the name for the gene that encodes the CD34 protein (see OMIM: 142230, MGI: 88329, HomoloGene: 1343). The CD34 protein is a member of a family of single-pass transmembrane sialomucin proteins that are expressed on early hematopoietic and vascular-associated tissue. CD34 is also an important adhesion molecule and is required for T cells to enter lymph nodes. It is expressed on lymph node endothelia and L-selectin, to which it binds, is on the T cell. Human [*Homo sapiens*] CD34 is described, in among others, the following database entries: Entrez 947, Ensembl ENSG00000174059, Uniprot P28906, Refseq NM_001025109 (mRNA), NP_001020280 (protein), the human CD34 gene is located on chromosome 1: 206.12-206.15 Mb. Mouse [*Mus* sp.] CD34 gene is described, in among others, the following database entries: Entrez 12490, Ensembl ENSMUSG00000016494, Uniprot Q3TJP6, Refseq NM_133654 (mRNA). The mouse CD34 protein is described in NP_598415 (CD34 antigen isoform 1), NP_001104529 (CD34 antigen isoform 2), AAB22109, AAB22108 and AAB19246. The mouse CD34 gene is located on chromosome Chr 1: 196.64-196.66 Mb. CD34 proteins have also been described in other mammals, for example: the rat [*Rattus norvegicus*] CD34 protein is described in NP_001100672, EDL95047, ACA42446 (CD34 antigen isoform 1), ACA42447 (CD34 antigen isoform 2); dog [*Canis familiaris*] CD34 protein is described in NP_001003341, AAB48004, ABA54265, AAB41055 and Q28270; cat [*Felis catus*] CD34 protein is described, in among others, database entries NP_001009318 and AAN15932; horse [*Equus caballus*] CD34 protein has been predicted and is described, in among others, database entry XP_001491646; domestic cattle/cow [*Bos taurus*] CD34 protein is described, in among others, database entries BAA78476 and NP_776434; swine [*Sus scrofa*] CD34 protein is described, in among others, database entries NP_999251 and AAL67838; domestic goats [*Capra hircus*] CD34 protein is described, in among others, database entry AAF76145; as well as in primates such as macaques [*Macaca* sp.] CD34 protein is described, in among others, database entries BAE02003, BAE02006, AAX99326 and the predicted XP_001111016; common marmosets [*Callithrix jacchus*] CD34 protein is described, in among others, database entry BAD04017; and in chimpanzees [*Pan troglodytes*] CD34 protein has been predicted and is described, in among others, database entries XP_001167718 (similar to CD34 isoform 1), XP_001167752 (similar to CD34 isoform 2) and XP_514160 (similar to CD34 isoform 3). Thus it appears that CD34 and its function is well conserved in mammals, as well as in other animals.

CD34 functions as a cell-cell adhesion molecule and plays a role in leukocyte migration and is thought to play a role in early hematopoiesis by mediating the attachment of stem cells to the bone marrow extracellular matrix or directly to stromal cells. It may also act as a scaffold for the attachment of lineage specific glycans, allowing stem cells to bind to lectins expressed by stromal cells or other marrow components, thus mediating the attachment of stem cells to bone marrow extracellular matrix or directly to stromal cells CD34 is selectively expressed on hematopoietic progenitor cells and the small vessel endothelium of a variety of tissues. Cells expressing CD34 (CD34$^+$ cell) are normally found in the umbilical cord and bone marrow as hematopoietic cells, in endothelial progenitor cells, in endothelial cells of blood vessels but not lymphatics (except pleural lymphatics), mast cells, a sub-population dendritic cells (which are factor XIIIa negative) in the interstitium and around the adnexa of dermis of skin, as well as cells in soft tissue tumors.

Overview of M-Cadherin Marker Protein

M-cadherin is a cell surface protein (also known as M-cadherin (myotubule), CDH15, Cadherin 15, CDH3, CDH14, CDHM: see OMIM: 114019, MGI: 106672, HomoloGene: 3622) that is a member of the cadherin superfamily of genes which encode calcium-dependent intercellular adhesion glycoproteins. Cadherins consist of an extracellular domain containing 5 cadherin domains, the extracellular Ca2+-binding domains, a transmembrane region and a conserved cytoplasmic domain. There are multiple classes of cadherin molecule, each designated with a prefix (generally noting the type of tissue with which it is associated). Human [*Homo sapiens*] M-cadherin is described, in among others, the following database entries: Entrez 1013, Ensembl ENSG00000129910, Uniprot P55291, Refseq NM_004933 (mRNA), NP_004924; P55291, AAH08951; EAW66741; EAW66742 (protein), the human M-cadherin gene is located on chromosome 16: 87.77-87.79 Mb. Mouse [*Mus* sp.] M-cadherin is described, in among others, the following database entries: Entrez 12555, Ensembl ENSMUSG00000031962, Uniprot P33146, Refseq NM_007662 (mRNA), NP_031688; AAC23585; P22146 (protein) and the mouse M-cadherin gene is located on chromosome 1: 196.64-196.66 Mb. Additionally, M-cadherin proteins have been described in other mammals, for example: rat [*Rattus norvegicus*] M-cadherin protein is described, in among others, database entries BAD15082 and NP_997496; dog [*Canis familiaris*] M-cadherin protein has been predicted and is described, in among others, database entry XP_536750; horse [*Equus caballus*]

M-cadherin protein has been predicted and is described, in among others, database entry XP_001917095; domestic cattle/cow [*Bos taurus*] M-cadherin protein is described, in among others, database entry NP_001095536; and platypus (*Ornithorhynchus anatinus*) M-cadherin protein has been predicted and is described, in among others, database entry XP_001511591. It appears, therefore, that M-cadherin and its function is well conserved in mammals, as well as in other animals.

M-cadherin is expressed on myoblasts and upregulated in myotubule-forming cells, such as satellite cells. Muscle satellite cells are a self-renewing pool of stem cells that give rise to daughter myogenic precursor cells in adult skeletal muscle, where they function in postnatal tissue growth and regeneration. It is believed that all satellite cells express transcription factors Pax3 and Pax7 (paired box proteins 3 and 7:Relaix, F., et al, 2005. "A Pax3/Pax7-dependent population of skeletal muscle progenitor cells." Nature 435, 948-953, 2005) and that activated satellite cells express myogenic transcription factors, such as Myf5 and MyoD as well as muscle-specific filament proteins such as desmin as they differentiate. M-cadherin is thought to be essential for the control of morphogenetic processes, specifically myogenesis, homophilic cell adhesion and may provide a trigger for terminal muscle cell differentiation. However, it has been shown using M-cadherin knock-out mice, those in whom M-cadherin genes are disrupted, that these mice were viable, fertile and showed no gross developmental defects suggesting that M-cadherin serves no absolutely required function during muscle development or regeneration (Hollnagel A, Grund C, Franke W W, Arnold H H. The cell adhesion molecule M-cadherin is not essential for muscle development and regeneration. Mol Cell Biol. 2002 July; 22(13):4760-70).

New Compositions and Methods

Ischemia is an inadequate flow of blood to a part of the body, usually caused by constriction or blockage of the blood vessels supplying it. If complete ischemia is sustained it can result in cell and tissue necrosis and irreversible damage. The heart, kidneys, and brain are among the organs that are the most sensitive to inadequate blood supply and ischemia is a feature of heart diseases, transient ischemic attacks, cerebrovascular accidents (stroke), ruptured arteriovenous malformations, and peripheral artery occlusive disease. Peripheral artery occlusive disease (PAOD) is also known as peripheral vascular disease (PVD) and most commonly referred to as peripheral artery disease (PAD) are terms that encompass diseases caused by the obstruction of peripheral arteries as a result of atherosclerosis, inflammatory processes leading to stenosis, an embolism or thrombus formation. Arteriosclerotic PAD complicates diabetes, hypertension, and hypercholesterolemia and may lead to ischemic leg pain, loss of muscular function, nonhealing foot ulcers, and ultimately, amputation of the affected limb.

The ischemic diseases prevented, treated or reduced by the methods and compositions of disclosed herein are ischemia and ischemia related disorders in mammals. The word mammal means any mammal that is susceptible to ischemia. Some examples of such mammals include, for example, companion animals, such as, but not limited to, dogs and cats; farm animals, such as, but not limited to, horses, pigs, cattle, sheep and goats; laboratory animals, such as, but not limited to, mice, rats, hamsters, rabbits and guinea pigs; animals used in sports, such as, but not limited to, horses and dogs; primates, such as, but not limited to, monkeys, apes, chimpanzees and humans. In some embodiments, humans are preferably treated according to a method disclosed herein and/or using a composition disclosed herein.

It has also been discovered that some of the endothelial cells identified within new vasculature of treated mammalian patients are very likely descended from $CD34^+$/M-cadherin$^+$ mesodermal-like precursor cells. Accordingly, the inventors have devised methods that use $CD34^+$/M-cadherin$^+$mesodermal-like precursor cells for preventing, treating or reducing the severity of endothelial dysfunction, or a vascular condition, or a circulatory condition, such as a condition associated with loss, injury or disruption of the vasculature within an anatomical site or system. The term "vascular condition" or "vascular disease" refers to a state of vascular tissue where blood flow is, or can become, impaired. Examples of vascular conditions that may be treated with the compositions and methods disclosed herein include, but are not limited to, atherosclerosis, preeclampsia, peripheral vascular disease, erectile dysfunction, cancers, renal failure, heart disease, and stroke. In various embodiments, $CD34^+$/M-cadherin$^+$ mesodermal-like precursor cells are used for preventing, treating or reducing the severity loss of circulation or endothelial dysfunction in an individual by inducing functional new blood vessels in a tissue of a mammal in need of such revascularization.

The compositions containing a population of isolated $CD34^+$/M-cadherin$^+$ mesodermal-like precursor cells are also useful in methods of preventing, treating or reducing the severity of ischemia related disorders such as stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), thrombosis or diabetes, among other disorders.

In some instances, the vascular condition or vascular disease arises from damaged myocardium. As used herein "damaged myocardium" refers to myocardial cells that have been exposed to ischemic conditions. These ischemic conditions may be caused by a myocardial infarction, or other cardiovascular disease. The lack of oxygen causes the death of the cells in the surrounding area, leaving an infarct that can eventually scar. In some cases, damaged or potentially damages myocardium is treated by direct administration into a target area before damage occurs (e.g., when damage is suspected of occurring) or as quickly as possible after damage occurs. Hence, in some cases, the administration of an effective amount of isolated $CD34^+$/M-cadherin$^+$ mesodermal-like precursor cells is advantageously employed on aged heart tissues that are in danger of ischemia, heart attack or loss of blood flow. In some cases, a composition of $CD34^+$/M-cadherin$^+$ mesodermal-like precursor cells is also advantageously employed on recently damaged myocardium, or on less recently damaged myocardium. As used herein "recently damaged myocardium" refers to myocardium that has been damaged within one week of treatment being started. In a preferred embodiment, the myocardium has been damaged within three days of the start of treatment. In some cases it is preferred to start treatment of the myocardium within twelve hours of the damage to the myocardium.

Arteriosclerotic peripheral arterial disease (PAD) complicates diabetes, hypertension, and hypercholesterolemia and may lead to ischemic leg pain, loss of muscular function, nonhealing foot ulcers, and, ultimately, amputation of the affected limb. Although autologous stem cell transplantation was previously thought to have potential for the treatment of PAD, the most effective precursor cell population and the duration of treatment was unknown until now. Using a preclinical murine model of PAD, the cellular fate of mononuclear bone marrow cells harvested from adult mice transgenic for an enhanced green fluorescent protein (GFP) and injected into the ischemic hind limbs of ApoE knockout mice was determined. The injected bone marrow mononuclear cells were followed by immunohistochemical analysis (and co-localization) of tissue-specific surface markers in the engrafted GFP$^{+/+}$ bone marrow cells. Following initial observations that showed that unfractionated GFP$^{+/+}$ bone marrow mononuclear cells differentiated into vascular and skeletal muscle structures, a side by-side comparison was performed of fractionated bone marrow mononuclear cells injected at a dose that was 2 orders of magnitude lower. Thus it was discovered that adult bone marrow mononuclear cells enriched for CD34$^+$ and M-cadherin$^+$ at a delivery dose of $3 \times 10^5$ cells were significantly more effective in long-term revascularization of ischemic limbs than were unfractionated bone marrow mononuclear cells or cells bearing CD34 or M-cadherin alone.

No prior study has identified or recognized the identity and value of non-satellite cell mesodermal-like precursor cells bearing both the CD34 and M-cadherin (CD34$^+$/M-cadherin$^+$) cell surface markers, or their ability to reverse many of the symptoms of ischemia.

A composition comprising an effective amount of mesodermal-like precursor cells that bear both the M-cadherin and CD34 cell surface markers is obtained, for example, from bone marrow cells or bone marrow cells that have been expanded in vitro, stem cells, embryonic endothelial cells or muscle cells, embryonic stem cell lines and hematopoietic stem cells, and is enriched using fluorescence activated cell sorter (FACS™), magnetic bead systems, magnetic-activated cell sorting (MACS™) or any other known cell enrichment techniques.

A method for treating ischemic and vascular conditions or a vascular disease in a mammal includes administering an effective amount of mesodermal-like precursor cells. The presently described in vivo mammalian findings indicate the unexpected or surprising result that symptoms of tissue ischemia(e.g., lower limb ischemia) is effectively treated by administering isolated mesodermal-like precursor cells bearing both the M-cadherin and CD34 cell markers directly into the ischemic tissue or limb.

A method for treating diseases and disorders associated with ischemia generally comprises administering to a mammal in need thereof a therapeutically effective amount of these double positive CD34$^+$/M-cadherin$^+$ mesodermal-like precursor cells sufficient to improve circulation and restore adequate levels of oxygenation to the tissues, including but not limited to the limbs and extremities.

A method for preventing, treating or reducing the severity of tissue ischemia, particularly an ischemic limb disorder, in a mammal having, or prone to, tissue ischemia includes administering to a mammal in need of such treatment a therapeutically effective amount of a cellular composition or graft comprising mesodermal-like precursor cells that are distinguished from other known stem cell populations by having both the M-cadherin and CD34 cell markers. The methods disclosed herein are practiced on mammals including companion animals, such as but not limited to, dogs and cats, as well as on human patients having an ischemic disorder, particularly an ischemic limb disorder.

A method of treating, managing, and/or preventing an ischemic disorder comprises administering to a patient in need of such treatment, management, or prevention a therapeutically or prophylactically effective amount of a pharmaceutical composition comprising CD34$^+$/M-cadherin$^+$ mesodermal-like precursor cell composition into or near a limb of the host or at or near a site impacted by ischemia.

Direct administration of the cellular composition or graft to a limb of the host at or near a site impacted by ischemia is employed in most cases. In some cases, ex vivo and in vivo procedures for expanding a population of stem and/or progenitor cells, such as are well know to the art and are, for example, as detailed in U.S. Pat. Nos. 7,344,881, 5,486,359, 5,736,396 and in PCT Application Publication No. WO/2005/112959, are similarly used for expanding the isolated CD34$^+$/M-cadherin$^+$ mesodermal-like precursor cells disclosed herein.

These CD34$^+$/M-cadherin$^+$ mesodermal-like precursor cells are myo-endothelial cell precursors. Thus these cells can differentiate into either new blood vessels or new muscle. In some applications, functional new blood vessels are induced in a tissue, particularly a limb, of a mammal, by administering to the limb, or other target tissue, a therapeutically effective amount of a cellular composition comprising CD34$^+$ M-cadherin$^+$ mesodermal-like precursor cells (i.e., cells bearing both the M-cadherin and CD34 cell markers). In some instances, the CD34$^+$ M-cadherin$^+$ mesodermal-like precursor cells are administered in the form of a graft. Such therapies are potentially useful for those undergoing cardiovascular procedures or receiving therapies that can result in ischemia, or having a condition that makes the individual more prone to ischemia. Such conditions include, but are not limited to, CAD, PAD, organ transplantation, chemotherapy or diabetes.

The CD34$^+$/M-cadherin$^+$ mesodermal-like precursor cells are administered intravascularly, intravenously, intraarterially, intraperitoneally, or via an intraluminal route. In some cases, the intraluminal route is preferred for direct delivery of the cells to a predetermined target site. Administration may be done, for example, using infusion via infusion catheter or via bolus injection at single or multiple sites.

In one exemplary treatment, CD34$^+$/M-cadherin$^+$ mesodermal-like precursor cells are obtained from the eventual recipient in an autologous transplant. In this case, bone marrow cells containing CD34$^+$/M-cadherin$^+$ mesodermal-like precursor cells are extracted from the subject prior to undergoing the procedure or receiving therapy, or before the development of or at an early stage of ischemia. The CD34$^+$/M-cadherin$^+$ mesodermal-like precursor cells are then isolated from the bone marrow of the subject, expanded in vitro if deemed necessary, and delivered to the subject at the site of potential or known ischemia. In the case of organ transplant, the delivery would be preferably concurrent with or after the transplant is performed.

A pharmaceutical composition comprises an amount of CD34$^+$/M-cadherin$^+$ mesodermal-like precursor cells isolated, for example, from bone marrow cells or bone marrow cells that have been expanded in vitro, stem cells, embryonic endothelial cells, embryonic stem cell lines or hematopoietic stem cells. The cells are suitably suspended in a pharmacologically acceptable vehicle. The cells may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions in aqueous vehicles, and may contain formulatory agents such as suspending, stabilizing and/or dispersing agents (non limiting examples being glycerol and dimethyl sufoxide (DMSO)). Nonlimiting examples of injectable dosage forms include sterile injectable liquids, e.g., solutions, emulsions and suspensions. In injectable compositions, the carrier is typically comprised of sterile pyrogen-free water, saline, various pharmaceutically acceptable buffering agents (for example phosphate, dextrose, proteins) preservatives and the like, as are known in the art, may be included in the present pharmaceutical compositions. In addition to the formulations described previously, the compounds may also be formulated as a depot preparation. Such long acting formulations may be administered by implantation (for example subcutaneously or intramuscularly) or by intramuscular injection. For example, compounds may be formulated with suitable polymeric or hydrophobic materials (for example as an emulsion in an acceptable oil (such as olive or peanut oil), polymers, ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

A therapeutically effective amount of $CD34^+/M$-cadherin$^+$ mesodermal-like precursor cells is, for example, about $10^2$ to about $10^{10}$ $CD34^+/M$-cadherin$^+$ mesodermal-like precursor cells, or about $10^2$ to about $10^9$ $CD34^+/M$-cadherin$^+$ mesodermal-like precursor cells. In some applications, a single dose of a composition containing about $3\times10^5$ is effective for long-term revascularization of ischemic limbs in a mouse. In some applications, a single dose of a composition containing about $2.5\times10^7$ is effective to reduce ischemia in a mouse tissue. The mouse animal model is considered predictive of similar results in humans and other mammals.

In various applications, $CD34^+/M$-cadherin$^+$ mesodermal-like precursor cells are used either alone or in combination with other therapies. For example, co-administration with satellite cells or other cells believed to be beneficial in preventing, treating or reducing the severity of tissue ischemia or an ischemia associated disorder in a mammal.

Thus, an exemplary method of treating, managing, and/or preventing ischemic disorders comprises administering to a patient in need of such treatment, management, or prevention a therapeutically or prophylactically effective amount of a pharmaceutical composition containing a population of $CD34^+/M$-cadherin$^+$ mesodermal-like precursor cells to a limb of the host at or near a site impacted by ischemia. $CD34^+/M$-cadherin$^+$ mesodermal-like precursor cells may be administered alone or in combination with angiogenic cytokines, such as but not limited to, platelet-derived growth factor (PDGF) vascular endothelial growth factor (VEGF) or fibroblast growth factor (FGF-2) to further stimulate both angiogenesis and vasculogenesis. Such an effective amount is effective when it stimulates the generation of myocytes or restores some vascularization in a tissue. These methods differ from prior methods in which mixed populations of stem cells and/or a variety of precursor cell types are administered together. In prior attempts at restoring damaged cardiovascular tissue or revascularization, the compositions that were administered contained a much smaller proportion of the critical cells that are specifically $CD34^+/M$-cadherin$^+$ mesodermal-like precursor cells, because their significance was unrecognized. Accordingly, the present compositions and methods are potentially much more effective than at least some prior compositions and methods for production of myocytes and/or restoring vascularization in a tissue. The specific identification of $CD34^+/M$-cadherin$^+$ mesodermal-like precursor cells reduces the number of cells required for effective treatment and also reduces potential adverse reactions.

A method for preventing, treating or reducing the severity of a vascular condition or a vascular disease in a mammal includes administering an effective amount of $CD34^+/M$-cadherin$^+$ mesodermal-like precursor cells. In vivo mammalian data, described in more detail below, indicate the unexpected finding that symptoms of tissue ischemia, especially lower limb ischemia, can be effectively treated by administering isolated $CD34^+/M$-cadherin$^+$ mesodermal-like precursor cells directly into or proximal to the ischemic tissue or limb to be treated.

Preventing, treating or reducing the severity of diseases and disorders associated with ischemia generally comprises administering to a mammal a therapeutically effective amount of a cellular composition comprising $CD34^+/M$-cadherin$^+$ mesodermal-like precursor cells sufficient to improve circulation and restore adequate levels of oxygenation to the tissues including, but not limited to, a limb of a mammal suffering from ischemia or at risk of ischemia in a limb.

Inducing functional new blood vessels in a tissue, particularly in the limb of a mammal with ischemia or an ischemia related disorder includes administering to a limb of the mammal a therapeutically effective amount of a cellular composition or graft comprising isolated and enriched $CD3^{4+}/M$-cadherin$^+$ mesodermal-like precursor cells. Such therapies are potentially useful for those undergoing a procedure (such as but not limited to, organ transplant), receiving therapies that can result in ischemia (e.g., chemotherapy), or having a condition that makes an individual prone to ischemia (e.g., diabetes). Therapeutic $CD34^+/M$-cadherin$^+$ mesodermal-like precursor cells are obtained from a donor (i.e., heterologus transplant) in some cases. In some cases it is preferred to obtain $CD34^+/M$-cadherin$^+$ mesodermal-like precursor cells from the eventual recipient (i.e., autologous transplant). In the latter case, bone marrow cells, for example are extracted from the subject prior to undergoing the procedure or receiving therapy, or preferably before the development of or at an early stage of ischemia. The $CD34^+/M$-cadherin$^+$ mesodermal-like precursor cells are isolated from the bone marrow of the subject, expanded if need be, and delivered to the subject to the site of potential or known ischemia. In the case of organ transplant, the delivery would, in some applications, be concurrent with or immediately after the transplant is performed. In some cases this procedure is practiced on a human patient having an ischemic disorder, particularly an ischemic limb disorder.

Disorders that will potentially benefit from application of a method described herein include those having at least one symptom such as decreased peripheral blood flow, increased apoptosis of cells, and necrosis in the limb tissues, relative to a normal individual (i.e., free of any ischemic limb disorder).

In accordance with the findings presented in the examples below, $CD34^+/M$-cadherin$^+$ mesodermal-like precursor cells are believed to achieve their beneficial effects of restoring blood flow and reducing cell death in ischemic tissues by differentiating into cell types that form new blood vessels and muscle cells when administered into ischemic limb tissue. While any mammal may be treated by the methods disclosed herein, in many applications, the mammal is a human.

A particularly advantageous feature of many embodiments of the instant methods is that the bone marrow stem cells are derived from the host and expanded in vitro prior to administration back into the host (i.e., allogenic). This provides the potential for cellular therapy using a patient's own cells, thereby avoiding potential complications associated with immune rejection and immunosuppressive regimens.

Isolation of $CD34^+/M$-cadherin$^+$ mesodermal-Like Precursor Cells.

The CD34+/M-cadherin+ mesodermal-like precursor cells are isolated from the bone marrow of the subject, utilizing, for example, flow cytometry by labeling cells bearing CD34 using fluorescent labeled CD34 antibodies. A similar process is done simultaneously using a labeled M-cadherin antibody that is labeled with a different fluorescent marker. In addition, should one wish to exclude a particular subgroup, for example satellite cells, by using a third and or fourth fluorescent label on Pax3 or Pax7 antibody, Pax3 or Pax7 positive satellite cells are excluded through gating. Standard flow cytometry and gating techniques known in the art are suitable for this purpose. CD34+/M-cadherin+ mesodermal-like precursor cells may be expanded in culture, and delivered to the subject to the site of potential or known ischemia. In the case of organ transplant, the delivery is preferably concurrent with or immediately (e.g., within a few hours) after the transplant is performed.

The procedures and techniques used for selecting immunogenic peptides described, for example, in "Current Protocols in Molecular Biology", Vol. 1 and 2 (Ausubel et al., eds., Green Publishing Associates, Incorporated, and John Wiley & Sons, Incorporated, New York, N.Y., 1989) Ch. 11.14, and "Antibodies: A Laboratory Manual" (Harlow and Lane, eds., Cold Spring Harbor Laboratory Press, Cold Spring Harbor, N.Y., 1988) Ch. 5, are suitably employed for selecting CD34 and M-cadherin proteins, polypeptides, peptides and fragments thereof used to elicit antibodies which are then used to identify, enrich and isolate CD34+/M-cadherin+ mesodermal-like precursor cells useful in the present methods.

The use of antibodies that selectively bind to one or more epitopes of CD34 or M-cadherin or epitopes of conserved variants of CD34 or M-cadherin and its fragments are also contemplated, particularly for use in the enrichment, purification or isolation of CD34+/M-cadherin+ mesodermal-like precursor cells. These antibodies include those available commercially. Such antibodies include, but are not limited to, polyclonal antibodies, monoclonal antibodies (mAbs), humanized antibodies, human-engineered antibodies, fully human antibodies, chimeric antibodies, single chain antibodies, Fab fragments, F(ab')2 fragments, fragments produced by a Fab expression library, anti-idiotypic (anti-Id) antibodies, catalytic antibodies, and epitope-binding fragments of any of the above.

In some applications, the antibodies, or fragments thereof, will preferentially bind to CD34 and/or M-cadherin, as opposed to other cell surface proteins. In such cases, the antibodies, or fragments thereof, selectively bind to CD34 and/or M-cadherin with a higher affinity or avidity than they bind to other cell surface proteins. An antibody "selectively binds" an antigen when it preferentially recognizes the antigen in a complex mixture of proteins and/or other macromolecules. The antibodies employed in some of the methods disclosed herein comprise an antigen-binding site that selectively binds to a particular epitope. Such antibodies may be capable of binding to different antigens, so long as the different antigens comprise that particular epitope. In some applications, homologous proteins from different species comprise the same epitope. In various applications, an antibody selectively binds an antigen when the dissociation constant ($K_D$) is 1 µM, or when the dissociation constant is 100 nM, or when the dissociation constant is 10 nM, for example.

Antibodies that selectively bind to CD34 and/or M-cadherin may be used, for example, in the detection, enrichment, purification or isolation of cells bearing these cell surface markers.

In addition to CD34 and/or M-cadherin antibodies and CD34 and/or M-cadherin kits, as are known to those of skill in the art and may be commercially available, antibodies for use in the CD34 and/or M-cadherin immunoassays disclosed herein include those that are generated de novo.

For the production of antibodies, various host animals, such as but not limited to chickens, hamsters, guinea pigs, rabbits, sheep, goats, horses, may be immunized by injection with a CD34 and/or M-cadherin protein, polypeptide, or peptide, a truncated CD34 and/or M-cadherin polypeptide, a functional equivalent of CD34 and/or M-cadherin, a mutant of CD34 and/or M-cadherin, an antigenic fragment thereof, or combinations thereof. Such host animals may include, but are not limited to, rabbits, mice, and rats, and CD34 and/or M-cadherin "knock-out" variants of the same. In addition, antibodies can be produced by immunizing female birds (chickens, for example) and harvesting the IgY antibodies present in their eggs. Various adjuvants may be used to increase the immunological response, depending on the host species, including, but not limited to, Freund's adjuvant (complete and incomplete), mineral salts such as aluminum hydroxide or aluminum phosphate, surface active substances, chitosan, lysolecithin, pluronic polyols, polyanions, peptides, oil emulsions, and potentially useful human adjuvants such as BCG (Bacille Calmette-Guerin) and *Corynebacterium parvum*. Alternatively, the immune response may be enhanced by combination and/or coupling with molecules such as keyhole limpet hemocyanin (KLH), tetanus toxoid, diphtheria toxoid, ovalbumin, cholera toxin, or fragments thereof.

Alternatively, expression as a fusion protein such as GST, HIS6, or another suitable fusion protein may be used. Polyclonal antibodies are heterogeneous populations of antibody molecules, such as those derived from the sera of the immunized animals or by mixing B-cells or monoclonal antibodies. Monoclonal antibodies, which are homogeneous populations of antibodies that arise from a single B-cell or its which selectively bind to a particular antigen or epitope, may be obtained by any technique that provides for the production of antibody molecules by continuous cell lines in culture. These include, but are not limited to, the hybridoma technique described by Kohler and Milstein (*Nature* 256:495-497, 1975), U.S. Pat. No. 4,376,110, and in "Antibodies: A Laboratory Manual", supra, Ch. 6; the human B-cell hybridoma technique described by Kozbor and Roder (*Immunol. Today* 4:72-79, 1983), and Cote et al. (*Proc. Natl. Acad. Sci. USA* 80:2026-2030, 1983), and the EBV-hybridoma technique described by Cole et al. (*Mol. Cell. Biochem.* 62:109-120, 1984), and Cole et al., (*Cancer Res.* 44:2750-2753, 1984).

A suitable animal, such as a mouse, rat, hamster, monkey, or other mammal, or an avian species, is immunized with an immunogen to produce antibody-secreting cells, including, but not limited to, B-cells, such as lymphocytes or splenocytes. In certain embodiments, lymphocytes (e.g., human lymphocytes) are immunized in vitro to generate antibody-secreting cells (Borrebaeck et al., *Proc. Natl. Acad. Sci. USA* 85:3995-3999, 1988). The hybridomas producing the monoclonal antibodies that are used in certain embodiments may be cultivated in vitro or in vivo. In some instances, the production of high titer monoclonal antibodies in vivo is the preferred method of producing antibodies for use in a testing method described herein. For some applications, antibody-secreting cells are fused with an "immortalized" cell line, such as a myeloid-type cell line, to produce hybridoma cells (see, e.g., "Antibodies: A Laboratory Manual", supra,).

For identifying cells bearing CD34 (or M-cadherin), in some cases high affinity antibodies are generated using animals that have been genetically engineered to be deficient in CD34 (or M-cadherin) production and activity. An example of such knock-out animals (often mice) are produced using established gene trapping methods, and viable animals that are genetically homozygous for the genetically engineered CD34 (or M-cadherin) mutation are generated and characterized. Given the relatedness of mammalian CD34 (and M-cadherin) amino acid sequences, the presently described homozygous knock-out mice (having never seen, and thus never been tolerized to, CD34 (or M-cadherin) are advantageously applied to the generation of antibodies against mammalian CD34 (or M-cadherin) sequences (i.e., CD34 (or M-cadherin) will be immunogenic in CD34 (or M-cadherin) homozygous knock-out animals). High affinity anti-CD34 (or anti-M-cadherin) antibodies generated from such animals are formulated into immunoassays that are used, as described herein, to identify cells that are to be used to treat patients at risk for ischemia. For example, human monoclonal antibodies are raised in transgenic animals (e.g., mice) that are capable of producing human antibodies (see, e.g., U.S. Pat. Nos. 6,075,181 and 6,114,598, and PCT Patent Application Publication No. WO 98/24893). Human immunoglobulin genes are introduced (e.g., using yeast artificial chromosomes, human chromosome fragments, or germline integration) into mice in which the endogenous Ig genes have been inactivated (see, e.g., Jakobovits et al., Nature 362:255-258, 1993, Tomizuka et al., Proc. Natl. Acad. Sci. USA 97:722-727, 2000, and Mendez et al., Nat. Genet. 15:146-156, 1997, describing the XenoMouse II® line of transgenic mice), for instance. Additional exemplary methods and transgenic mice suitable for the production of human monoclonal antibodies are described, e.g., in Jakobovits, Curr. Opin. Biotechnol. 6:561-566, 1995, Lonberg and Huszar, Int. Rev. Immunol. 13:65-93, 1995, Fishwild et al., Nat. Biotechnol. 14:845-851, 1996, Green, J. Immunol. Methods 231:11-23, 1999, and Little et al., Immunol. Today 21:364-370, 2000. Alternatively mouse monoclonal antibodies that selectively bind human CD34 (or M-cadherin) from other mammals are subject to sequential chain shuffling. Such monoclonal antibodies include but are not limited to, mouse monoclonal antibodies raised against mouse CD34 (or M-cadherin) but selectively bind to (i.e., cross-react with) human CD34 (or M-cadherin). For example, the heavy chain of a given mouse monoclonal antibody may be combined with a new repertoire of human light chains, and antibodies with the desired affinity may be selected. The light chains of the selected antibodies may then be combined with a new repertoire of human heavy chains, and antibodies with the desired affinity may be selected. In this manner, human antibodies having the desired antigen binding selectivity and affinity are obtained. Alternatively, the heavy chain of a given mouse monoclonal antibody may be combined with a new repertoire of human light chains, and antibodies with the desired affinity selected from this first round of shuffling. In addition, the light chain of the original mouse monoclonal antibody is combined with a new repertoire of human heavy chains, and antibodies with the desired affinity selected from this second round of shuffling. Then, human light chains from the antibodies selected in the first round of shuffling are combined with human heavy chains from the antibodies selected in the second round of shuffling. Thus, human antibodies having the desired antigen binding selectivity and affinity are selected.

Antibodies for use in identifying, enriching and isolating cells bearing CD34 and M-cadherin cell surface markers, as disclosed herein, may be additionally used to screen for binding to CD34 and/or M-cadherin in cell samples obtained from an individual (for example, human, mouse, dog, cat, horse), using any suitable technique that detects binding of an antibody to an antigen. In some embodiments, similar methods and assay formats are used to detect CD34 and M-cadherin on cells obtained from patients with ischemia. For example, the ability of a monoclonal antibody to bind CD34 and/or M-cadherin may be assayed by standard methods, such as electrophoresis and Western blotting (see, e.g., Ch. 10.8 in "Current Protocols in Molecular Biology", Ch. 11.14, Vol. 1 and 2 (Ausubel et al., eds., Green Publishing Associates, Incorporated, and John Wiley & Sons, Incorporated, New York, N.Y., 1989 and "Antibodies: A Laboratory Manual" (Harlow and Lane, eds., Cold Spring Harbor Laboratory Press, Cold Spring Harbor, N.Y., 1988), competitive binding ELISA assays (see, e.g., "Antibodies: A Laboratory Manual," supra, Ch. 14) the results of which are determined using a colorimeter with one or more fixed wavelengths, or a variable wavelength spectrophotometer, or an ELISA reader, or a fluorometer. In some embodiments, such assays are used to determine the presence of CD34 and M-cadherin bearing cells in patients with ischemia, to determine whether the patient is eligible for autologous cell transplantation.

A binding assay may be used to quantify the binding kinetics (e.g., rate constant) or the binding affinity (e.g., association or dissociation constant) of an antibody against CD34 or M-cadherin. The binding kinetics or binding affinity can be determined in the "solid-phase" by immobilizing antigen (e.g., CD34 or M-cadherin) on a solid support. In such assays, the immobilized antigen "captures" antibody from solution. Alternatively, binding kinetics or binding affinity may be determined using ELISA-based methods, or using biosensor-based technology, such as Biacore surface plasmon resonance technology (Biacore International AB, Uppsala, Sweden). Many such methods are known to those skilled in the art (see, e.g., "Antibody Engineering: A Practical Approach" (McCafferty et al., eds., Oxford University Press, Oxford, United Kingdom, 1996), Goldberg et al., Curr. Opin. Immunol. 5:278-281, 1993, Karlsson et al., J. Immunol. Methods 145: 229-240, 1991, Malmqvist, Curr. Opin. Immunol. 5:282-286, 1993, and Hoogenboom, supra). The kinetics or affinity of antibody binding is measured for an antibody-antigen complex in solution. Such techniques are known to those skilled in the art, including, but not limited to, the "kinetic exclusion assay" (see, e.g., Blake et al., J. Biol. Chem. 271:27677-27685, 1996, and Drake et al., Anal. Biochem. 328:35-43, 2004). Sapidyne Instruments, Incorporated (Boise, Id.), among others, provides instrumentation for performing kinetic exclusion assays. These types of assays may be used to characterize and/or select antibodies for use in identifying and enriching cells bearing both CD34 and M-cadherin. These assays may also be used to determine levels of cells bearing both CD34 and M-cadherin in tissues from patients that are thought to be at some risk, or are known to be suffering from ischemia.

The epitope to which a monoclonal antibody binds may be identified by any of a number of assays (see, e.g., Morris, Methods Mol. Biol. 66:1-9, 1996). For example, epitope mapping may be achieved by gene fragment expression assays or peptide-based assays. In a gene fragment expression assay, for example, nucleic acids encoding fragments of CD34 (or M-Cadherin) are expressed in prokaryotic cells and isolated. The ability of a monoclonal antibody to bind those fragments is assessed, e.g., by immunoblotting or immunoprecipitation. Nucleic acids encoding fragments of CD34 (or M-cadherin) are then transcribed and translated in vitro in the presence of radioactive amino acids. The radioactively labeled fragments of CD34 (or M-cadherin) may then be tested for binding to a monoclonal antibody. Fragments of CD34 (or M-cadherin) may also be generated by proteolytic fragmentation. An epitope may also be identified using libraries of random peptides displayed on the surface of phage or yeast, or a library of overlapping synthetic peptide fragments of CD34 (or M-cadherin), and testing for binding to a monoclonal antibody. An epitope may also be identified using a competition assay wherein, monoclonal antibodies may be deemed to share an epitope if each blocks the binding of the other by 50% or greater. Alternatively, to determine if two or more monoclonal antibodies bind the same epitope, epitope binning may be performed (see, e.g., Jia et al., *J. Immunol. Methods* 288: 91-98, 2004), using, for example, Luminex® 100 multiplex technology and the Luminex® 100™ analyzer (Luminex Corporation, Austin, Tex.). Immunoassays based on any of the above described technologies and devices (those named, those implied and those known to the art) are employed in various embodiments to detect CD34 and M-Cadherin bearing cells in patients that are thought to be at risk for ischemia.

Antibodies directed against CD34 (or M-cadherin), or conserved variants or peptide fragments thereof, which are discussed above, may also be used to identify, enrich and purify cell bearing CD34 and M-cadherin from patients with ischemia, as well as in diagnostic and/or prognostic assays, as described herein. Such diagnostic and/or prognostic methods may be used to detect abnormalities in the level of CD34 and M-cadherin bearing cells in a patient's body or tissues and may be performed in vivo or in vitro, such as, for example, on biopsy tissue. For example, antibodies directed to epitopes of CD34 or M-cadherin are used in vivo to detect the level of CD34 and/or M-cadherin bearing cells present in the body. Such antibodies are labeled, e.g., with a radio-opaque or other appropriate compound, and injected into a subject, in order to visualize cells bearing CD34 and M-cadherin in the body, using methods such as X-rays, CAT-scans, or MRI.

Alternatively, immunoassays or fusion protein detection assays may be utilized on biopsy and autopsy samples in vitro to permit assessment of the expression pattern of CD34 and M-cadherin bearing cells. Such assays may include the use of antibodies directed to epitopes of any of the domains of CD34 (or M-cadherin). For example, in various embodiments antibodies, or fragments thereof, are used to quantitatively or qualitatively detect CD34 or M-cadherin, conserved variants, or peptide fragments thereof. This may be accomplished, for example, by immunofluorescence techniques employing a fluorescently labeled antibody coupled with ultraviolet microscopic, flow cytometric, or fluorometric detection.

The CD34 and M-cadherin antibodies (or fragments thereof) may also be used to determine the level of cells bearing both CD34 and M-cadherin markers in a tissue sample, and may be additionally employed histologically. For example, in immunofluorescence, immunoelectron microscopy, or non-immuno assays, for in situ detection of CD34 and M-cadherin bearing cells. In situ detection may be accomplished by removing a histological specimen from a patient, and applying thereto a labeled antibody, performing some embodiments of a CD34 or M-cadherin immunoassay. The antibody (or fragment) is preferably applied by overlaying the labeled antibody (or fragment) onto a biological sample. Through the use of such a procedure, it is possible to determine not only the presence of CD34 and M-cadherin, or conserved variants or peptide fragments, but also its distribution in the examined tissue.

The binding activity of a given lot of CD34 or M-cadherin antibody may be determined using well-known techniques for detecting antibody binding. Those skilled in the art will be able to determine operative and optimal assay conditions for each determination by employing routine experimentation.

One of the ways in which the CD34 and/or M-cadherin antibody may be detectably labeled is by linking the same to an enzyme for use in an enzyme immunoassay (see, e.g., "Immunoassays: A Practical Approach" (Gosling, ed., Oxford University Press, Oxford, United Kingdom, 2000)). The enzyme that is bound to the antibody will react with an appropriate substrate, preferably a chromogenic substrate, in such a manner as to produce a chemical moiety that may be detected, for example, by spectrophotometric, fluorimetric, or visual means. These assays are read and analyzed using chromatometers, spectrophotmeters and fluorometers, respectively. Enzymes that may be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, glucose oxidase, asparaginase, beta-galactosidase, ribonuclease, urease, catalase, glucose-6-phosphate dehydrogenase, glucoamylase and acetylcholinesterase. The detection may be accomplished by colorimetric methods that employ a chromogenic substrate for the enzyme. The detection may also be accomplished using methods that employ a fluorogenic substrate in an enzyme-lined fluorescence (ELF) assay. Detection may also be accomplished by visual comparison of the extent of enzymatic reaction of a substrate in comparison with similarly prepared standards.

Additionally, detection may also be accomplished using any of a variety of other immunoassays. For example, by radioactively labeling CD34 or M-cadherin antibodies or antibody fragments, it is possible to detect CD34 and M-cadherin bearing cells through the use of a radioimmunoassay (RIA). The radioactive isotope may be detected, for example, by using a gamma or scintillation counter, or by autoradiography. Such antibodies or fragments may also be labeled with a fluorescent compound. When a fluorescently labeled antibody is exposed to light of the proper wavelength, it may be detected due to fluorescence. Exemplary fluorescent labeling compounds include, but are not limited to, fluorescein isothiocyanate, rhodamine, phycoerythrin, phycocyanin, allophycocyanin, o-phthaldehyde, and fluorescamine. Such antibodies may also be detectably labeled using a fluorescence emitting metal, such as 152Eu, or others of the lanthanide series. These metals may be attached to an antibody or fragment using such metal chelating groups as diethylenetriaminepentacetic acid (DTPA) or ethylenediaminetetraacetic acid (EDTA).

A CD34 and/or M-cadherin antibody, or fragment thereof, also may be detectably labeled by coupling it to a chemiluminescent compound. The presence of the chemiluminescent-tagged antibody or fragment is detected by luminescence that arises during the course of a chemical reaction. Examples of useful chemiluminescent labeling compounds include, but are not limited to, luminol, isoluminol, theromatic acridinium ester, imidazole, acridinium salt and oxalate ester. Likewise, a bioluminescent compound may be used to label the CD34 and/or M-cadherin antibodies, in some cases. Bioluminescence is a type of chemiluminescence found in biological systems, in which a catalytic protein increases the efficiency of the chemiluminescent reaction. The presence of a bioluminescent antibody or fragment is once again detected by luminescence. Exemplary bioluminescent compounds for purposes of labeling include, but are not limited to, luciferin, luciferase and aequorin (green fluorescent protein; see, e.g., U.S. Pat. Nos. 5,491,084, 5,625,048, 5,777,079, 5,795,737, 5,804,387, 5,874,304, 5,968,750, 5,976,796, 6,020,192, 6,027,881, 6,054,321, 6,096,865, 6,146,826, 6,172,188 and 6,265,548).

CD34 and M-cadherin bearing cells are identified and enriched or isolated using any of a variety of cell sorting technologies known to those of skill in the art. For example, preparative scale immunoprecipitations are used in some applications to detect the presence of cells bearing CD34 and M-cadherin. Monodispersed magnetic beads are also available as a support material which offers certain advantages over polydisperse agarose beads. Magnetic beads have the ability to bind extremely large protein complexes and the complete lack of an upper size limit for such complexes, as unlike agarose beads which are sponge-like porous particles of variable size, magnetic beads are small, solid and (in the case of monodisperse magnetic beads) spherical and uniform in size. The lower overall binding capacity of magnetic beads for immunoprecipitation make it much easier to match the quantity of antibody needed for diagnostic immunoprecipitations precisely with the total available binding capacity on the beads which results in decreased background and fewer false positives. The increased reaction speed of the immunoprecipitations using magnetic bead technologies results in superior results when the analyte protein is labile due to the reduction in protocol times and sample handling requirements which reduces physical stresses on the samples and reduces the time that the sample is exposed to potentially damaging proteases. Agarose bead-based immunoprecipitations also may be performed more quickly using small spin columns to contain the agarose resin and quickly remove unbound sample or wash solution with a brief centrifugation (Celis, J. E., Lauridsen, J. B., and Basse, B. (1994) Determination of antibody specificity by Western blotting and immunoprecipitation. In: Celis, J. E. (ed.), Cell Biology. A Laboratory Handbook, Academic Press, New York, Vol. 2, pp. 305-313. Mason, D. W., and Williams, A. F. (1986) Kinetics of antibody reactions and the analysis of cell surface antigens. In: Weir, D. M., Herzenberg, L. A., Blackwell, C., and Herzenberg, L. A. (ed.), Handbook of Experimental Immunology, Blackwell, Oxford, vol. 1, chapter 38). Alternatively, CD34 and M-Cadherin bearing cells may be identified and enriched or isolated or using flow cytometry, fluorescence activated cell sorting (FACS™) as well as those methods based on magnetic beads such as Magnetic-activated cell sorting (MACS™), or any other suitable technique.

The principle of flow cytometry is that a beam of light (usually a laser) of a single wavelength is directed onto a hydro-dynamically-focused stream of fluid. A number of detectors are aimed at the point where the stream passes through the light beam: one in line with the light beam (Forward Scatter or FSC) and several perpendicular to it (Side Scatter (SSC) and one or more fluorescent detectors). Each suspended particle from 0.2 to 150 micrometers passing through the beam scatters the light in some way, and fluorescent chemicals found in the particle or attached to the particle may be excited into emitting light at a higher wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle. FSC correlates with the cell volume and SSC depends on the inner complexity of the particle (i.e., shape of the nucleus, the amount and type of cytoplasmic granules or the membrane roughness). Some flow cytometers eliminate the need for fluorescence and use only light scatter for measurement. Other flow cytometers form images of each cell's fluorescence, scattered light, and transmitted light. Modern flow cytometers are able to analyse several thousand particles every second, in "real time," and can actively separate and isolate particles having specified properties. A flow cytometer is similar to a microscope, except that, instead of producing an image of the cell, flow cytometry offers "high-throughput" automated quantification of set parameters. To analyze solid tissues, a single-cell suspension must first be prepared.

A flow cytometer has five main components: (1) a flow cell—liquid stream (sheath fluid), which carries and aligns the cells so that they pass single file through the light beam for sensing; (2) an optical system, commonly used are lamps (mercury, xenon); high-power water-cooled lasers (argon, krypton, dye laser); low-power air-cooled lasers (argon (488 nm), red-HeNe (633 nm), green-HeNe, HeCd (UV)); diode lasers (blue, green, red, violet) resulting in light signals; (3) a detector and Analogue-to-Digital Conversion (ADC) system, which generates FSC and SSC as well as fluorescence signals from light into electrical signals that can be processed by a computer; (4) an amplification system—linear or logarithmic; (5) a computer for analysis of the signals. Modern instruments often have multiple lasers and fluorescence detectors (as many as 4 lasers and 18 fluorescence detectors in commercially available models). Increasing the number of lasers and detectors allows for multiple antibody labeling, and can more precisely identify a target population by their phenotype. Certain instruments can even take digital images of individual cells, allowing for the analysis of fluorescent signal location within or on the surface of cells. The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to hematology. Plots are often made on logarithmic scales. Because different fluorescent dyes' emission spectra overlap, signals at the detectors have to be compensated electronically as well as computationally. Often, data acquired using the flow cytometer can be re-analyzed elsewhere, freeing up the machine for other people to use.

Fluorescence-activated cell sorting (FACS™) is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest. While scientists often use the term FACS™ for all types of sorting and non-sorting applications, it is not a generic term for flow cytometry.

For fluorescence-activated cell sorting, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell's being in a droplet. Just before the stream breaks into droplets, the flow passes through a fluorescence measuring station where the fluorescent character of each cell is measured. An electrical charging ring is placed just at the point where the stream breaks into droplets. A charge is placed on the ring based on the immediately-prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. The fluorescence labels that can be used, depend on the lamp or laser used to excite the fluorochromes and on the detectors available: These labels include but are not limited to those for the blue argon laser (488 nm) which is an air cooled laser and therefore less expensive to operate. It is the most commonly available laser on single laser machines. Another is green (usually labelled FL1): fluroscine isothiocyanate) (FITC, Alexa Fluor 488, GFP, CFSE, CFDA-SE, DyLight 488, still another is orange (usually FL2): PE, PI. Red channel (usually FL3): PerCP, PE-Alexa Fluor 700, PE-Cy5 (TRI-COLOR), PE-Cy5.5. Infrared (usually FL4; not provided by all FACS machines as standard): PE-Alexa Fluor 750, PE-Cy7. When using a red diode laser (635 nm) APC, APC-Cy7, Alexa Fluor 700, Cy5, Draq-5, TMA (Tissue Metachlorian Antigen). When using a violet laser (405 nm), Pacific Orange, Amine Aqua, Pacific Blue, DAPI, Alexa Fluor 405. (see for example, Flow Cytometry First Principles by Alice Longobardi Givan (ISBN 0471382248), Practical Flow Cytometry by Howard M. Shapiro (ISBN 0471411256), Flow Cytometry for Biotechnology by Larry A. Sklar (ISBN 0195152344), Handbook of Flow Cytometry Methods by J. Paul Robinson, et al. (ISBN 0471596345), Current Protocols in Cytometry, Wiley-Liss Pub. (ISSN 1934-9297), Flow Cytometry in Clinical Diagnosis, v4, (Carey, McCoy, and Keren, eds), ASCP Press, 2007. (ISBN 0891895485), Ormerod, M. G. (ed.) (2000) Flow cytometry—A practical approach. 3rd edition. Oxford University Press, Oxford, UK. Ormerod, M. G. (1999) Flow Cytometry. 2nd edition. Bios Scientific Publishers, Ltd. Oxford. Flow Cytometry—a Basic Introduction. Michael G. Ormerod, 2008. (ISBN 978-0955981203).

Magnetic-activated cell sorting (MACS®) is a method for separation of various cell populations depending on their surface antigens (CD molecules). Mixtures of cells to be separated are incubated with magnetic beads coated with antibodies against a particular surface antigen. Thus cells expressing the antigen attach to the magnetic beads. Afterwards the cell solution is transferred on a column placed in a strong magnetic field and the cells attached to the beads (expressing the antigen) stay on the column, while other cells (not expressing the antigen) flow through. Using this method, the cells are separated positively or negatively with respect to the particular antigen(s). In positive selection the cells expressing the antigen(s) of interest, which attached to the magnetic column, are washed out to a separate vessel, after removing the column from the magnetic field. This method is useful for isolation of a particular cell type, for instance $CD34^+$ or M-cadherin$^+$ cells. In negative selection the antibody used is against surface antigen(s) which are known to be present on cells that are not of interest. After administration of the cells/magnetic beads solution onto the column the cells expressing these antigens bind to the column and fraction that goes through is collected, as it contains almost no cells with undesired antigens. Magnetic beads conjugated to an antibody against an antigen of interest are not always available, but it is possible to use magnetic beads coated with anti-fluorochrome antibodies and then incubate these beads with fluorescent-labeled antibodies against the antigen of interest and may thus serve for cell separation with respect to the antigen. Thus, it can be appreciated that a wide variety technologies are currently available to implement the isolation and enrichment of CD34 and M-cadherin bearing cells for the prevention or treatment of ischemia.

EXAMPLES

Animals: All mice examined were purchased, bred, and manipulated under protocols approved by the Animal Welfare Committee of the University of Texas Health Science Center, Houston, Tex. C57BL/6 mice transgenic for an enhanced variant of the jellyfish green fluorescent protein (GFP) were a generous gift from Prof. M. Okabe (RIKEN, Kobe, Japan), were used as bone marrow cell donors. Thus all donor derived cells could be identified by the expression of GFP.

Collection of Bone Marrow Cells. Eight to 12 month-of-age GFP$^{+/+}$ mice were euthanized by $CO_2$ inhalation and tibia and femur bones were removed from both hind limbs. To collect the bone marrow, the bone shafts were flushed with PBS containing 10% FBS (Cambrex, East Rutherford, N.J.) using a 26 gauge needle. To remove cell clumps, the cell suspensions were passed through a 100-μm nylon cell strainer (BD Falcon, San Jose, Calif.) and centrifuged at 1000×rpm for 5 min at 4° C. The cell pellets were resuspended in a lysing reagent (BD Biosciences, San Jose, Calif.) to remove red blood cells (RBCs), washed with PBS, and passed through 40-μm nylon cell strainer (BD Falcon).

Generation of ischemia: Twelve month-of-age C57BL/6J apolipoprotein E homozygous knockout (ApoE$^{-/-}$) mice, that lack functional apolipoprotein E, and as a result develop spontaneous hypercholesterolemia and atherosclerosis, were used in an established mouse model of limb ischemia. The ApoE$^{-/-}$ knockout mice were anesthetized with oxygen enriched with 2% isoflurane. The hind limbs were shaved and under a dissecting microscope a longitudinal skin incision was made in the mid-region of the hind limb to expose the left femoral artery. The proximal portion of the common femoral artery was then ligated twice at adjacent sites with the use of #6 nylon sutures.

Intra-Arterial Application of Bone Marrow Cells: A 1 mL syringe with a 27 gauge needle attached was used to slowly inject treatment cells or control PBS into the mice in the common femoral artery immediately distal to the ligation site in the ischemic limbs. The treatment group consisted of fifteen mice (n=15) that received $2.5 \times 10^7$ bone marrow cells and a control group containing thirteen mice (n=13) that received an equivalent volume of cell free PBS. Following the intra-arterial delivery of the bone marrow cells, the incision site was repaired, and the animal was returned to the cage to recover and monitored daily for surgical complications and any discomfort.

Histological and Immunochemical Analysis

Collection and Histologic Preparation of Ischemic and Normal Limbs. Recipient ApoE$^{-/-}$ knockout mice were euthanized by $CO_2$ asphyxiation at several time points: 30 min and 3, 7, 14, 21 and 30 days post BMC transplantation surgery. The hind limbs were removed, dissected free of skin, and fixed in 10% formalin solution (Sigma-Aldrich, St Louis, Mo.) for 48 hours at 4° C. The limbs were then decalcified in 10% EDTA/PBS (pH 7.2, Sigma-Aldrich) at 4° C. for 10-15 days. Decalcification was confirmed by a Faxitron X-ray system (Faxitron X-ray, LLC, Lincolnshire, Ill.). The decalcified limbs were incubated in 10% sucrose-PBS overnight at 4° C. and then incubated in 30% sucrose-PBS for an additional 2 days. The limbs were then cut transversely into 5 segments (thigh 2, lower leg 2, proximal foot 1) and each section was placed into a vinyl specimen mold and covered with cryo-protective compound, Tissue-Tek® O.C.T., frozen on dry ice, wrapped in aluminum foil, and stored until sectioning at −80° C. Cryosections (6-10 μM each) were prepared from the frozen limbs and air-dried after mounting on glass slides. Each section was fixed in cold acetone for 5 min, dried, and washed with PBS. GFP-positive tissue cells were visualized with a Leica DM LB fluorescent microscope (Meyer Instruments, Houston, Tex.). In order to reduce detection of auto-fluorescence, the FITC/Texas red dual filter set was used to visualize authentic green fluorescence emission by GFP. In addition, Alexa Fluor-594 conjugated anti-GFP antibodies (Molecular Probes, Invitrogen™, Carlsbad, Calif.) were used to confirm GFP expression. DAPI (Chemicon, Temecula, Calif.) was used to stain cell nuclei in all tissues.

Example 1

Distribution of Engrafted GFP$^{+/+}$ Bone Marrow Cells

Figure 1:
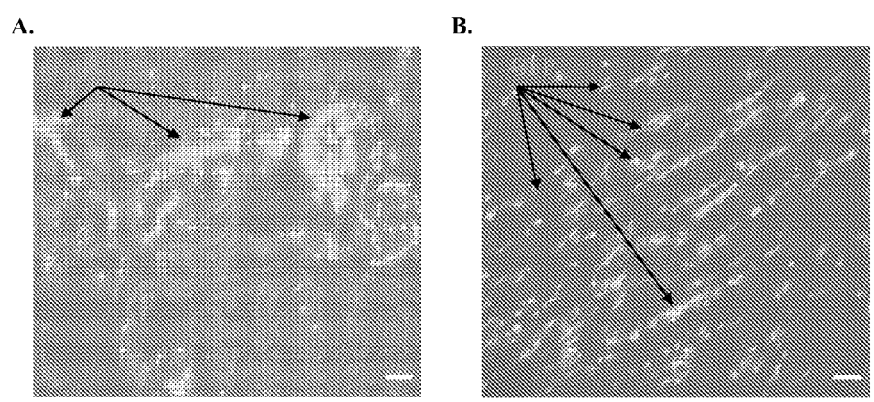
FIG. 1 shows the distribution of adult $GFP^{+/+}$ bone marrow mononuclear cells (BMCs) in the ischemic legs of $ApoE^{-/-}$ knockout mice at 7 and 21 days post transplantation.

In order to track the distribution of donor bone marrow cells, freshly harvested unfractionated mononuclear bone marrow cells from adult mice transgenic for enhanced GFP variant were used for intra-arterial infusions into the ischemic limbs of recipient Apo E$^{-/-}$ knockout mice, which share the C57BL/6 background. Preliminary studies showed that >90% of nucleated bone marrow cells from GFP$^{+/+}$ mice displayed authentic green fluorescence when studied under epifluorescence microscopy using a dual FITC/Texas Red band pass filter system, distinct from the markedly reduced auto-fluorescence of tissues such as elastic membranes within arterial vessel walls (data not shown). In microscopic sections prepared from of decalcified limbs harvested 30 min after intra-arterial injection of GFP$^{+/+}$ bone marrow cells (n=3). GFP$^{+/+}$ bone marrow cells were found in the transverse limb sections to accumulate in cellular aggregates (<25 cells) between skeletal muscle bundles above and below the knee and proximal foot but in greater abundance along the margins of the surgical incision site. At 7 days after transplantation, GFP positive cells were present at all levels analyzed (thigh, lower leg, and proximal foot) with trend for higher number of GFP positive cells and tissue structures to locate in proximity to the vasculature (FIG. 1A). GFP positive cells were also observed in the vascular lumen in the bone cavity (data not shown). With exception of the foot pad, GFP positive cells forming tissue structures resembling arterioles and skeletal muscle fibers were found to be dispersed between the muscles fibers at all levels of the ischemic limb (FIG. 1B).

Example 2

Immunohistochemistry

Leg samples were fixed in formalin, decalcified, and then transversely cut (6-10 μm) into sections. For immunohistochemical analysis, tissue sections were permeabilized with 0.2% Triton X-100/PBS for 10 min at RT, followed by treatment with a proteolytic enzyme mixture (GeneTex) for 20 min at 37° C. Image-iT FX signal enhancer (Molecular Probes) was applied to each section according to the manufacturer's instruction. Subsequently, tissue sections were incubated with blocking buffer containing 5% normal donkey serum (Abcam, Inc. Cambridge, Mass.) for 1 hour at RT and incubated with primary antibody against GFP (Invitrogen™), CD34 (Abcam, Inc.), von Willebrand factor (Abcam, Inc.), CD31 (Abcam, Inc.), laminin-β2 (Chemicon), CD105 (Abcam, Inc.), or α-smooth muscle actin (GeneTex) overnight at 4° C. Sections were washed in PBS 3 times for 10 min and incubated with Alexa Fluor-594 donkey anti-rat IgG, donkey anti-goat IgG, or donkey anti-rabbit IgG for 60 min at RT. The fluorescence signals were visualized with a Leica DM LB fluorescent microscope (Meyer Instruments).

Each section was examined immunohistochemically with primary antibodies against CD34, von Willebrand factor, CD31, CD105, or M-cadherin, respectively. The sections were incubated with corresponding secondary antibodies, and fluorescent signals were visualized with a Leica DM LB fluorescent microscope.

Example 3

Differentiation into Small Arteries and Skeletal Muscle Fibers

Cross sections from the decalcified ischemic legs obtained from recipient mice as early as 7 days and continuing at 14 days after surgery and treatment show DAP+ cells that were dividing and GFP positive cells formed curvilinear cord-like structures at 7 days (FIG. 2a A) and at 14 days (FIG. 2b E). These cells (as indicated by thick arrows) also stained positive for CD34 at 7 days (cells indicated by thick arrows in FIG. 2a B) and at 14 days (cells indicated by thick arrows in FIG. 2b F). Cells from this tissue did not stain positive for CD31 at 7 days (FIG. 2a C), but did stain positive for CD31 expression at 14 days as shown in FIG. 2G and indicated by thick arrows. Similarly cells expressing CD105 were not present at 7 days after the treatment/surgery (FIG. 2a D) but were present at 14 days after the treatment/surgery as shown in FIG. 2b H with CD105 expressing cells indicated by the thicker arrows.

At 21 and 28 days after treatment these GFP positive cells had developed into endothelium-like cell layer, beneath which were found cells staining positive for α-smooth muscle cell actin (FIGS. 3a-b). This is consistent with de novo formation of arterioles located between resident (non-fluorescent) skeletal muscle fibers and in subcutaneous tissue, and characterized by the presence of endothelial and vascular smooth muscle cells at 21 days (as seen in FIG. 3a B) and at 28 days (as seen in FIG. 3a B). In addition to the de novo formation of small blood vessels, occasional, GFP positive cells were determined to be incorporated into the endothelial (lumen-bound) layer of pre-existing, non-fluorescent small arteries (FIG. 3a A and B) also seen in the same region and shown in FIG. 3a B are cells of small arteries that express α-SMC actin (indicated by the thicker arrows).

Cross sections from treated ischemic legs obtained from recipient mice at 21 days after treatment showed isolated skeletal muscle fiber formation from GFP$^{+/+}$ bone marrow cells was in transverse sections from ischemic limbs above and below the knee (FIG. 3b C). The same was true in 28 day samples (FIG. 3b E). Skeletal myofiber formation from allogenic GFP$^{+/+}$ bone marrow cells was notable at 21 days post treatment (FIG. 3b D) but was more distinct at 28 days (FIG. 3b F). De novo formed myo fibers in clusters surrounded by a basment membrane that stained positive for laminin β2 (indicated by the thicker arrows) were occasionally observed at 21 days (FIG. 3b D) and which were common by 28 days (FIG. 3b F).

Example 4

Imaging of Hind Limb Blood Flow

At 3-day intervals following surgery and treatment until the time that the mice were sacrificed, at 30 days post treatment, laser doppler flow imaging was performed on the ischemic and non-ligated contralateral limbs to establish the degree of blood flow recovery in ischemic and control limbs. A laser doppler imaging device (Perimed, Inc. North Royalton, Ohio) was used to measure cutaneous (body surface) blood flow in the ischemic and contralateral limbs of the mice immediately before the surgery and treatment, 30 minutes after-surgery, and at 3-day intervals until the mice were euthanized at 30 days post surgery. To reduce perfusion variation caused by ambient temperature and other changes, mice were placed on a heating pad at 37° C. for 30 min before undergoing imaging. Each hind limb was scanned 3 times to verify the reproducibility of blood flow signals in the limbs and average blood flow values were calculated for the ischemic and contralateral limbs. The degree of ischemia and flow recovery after surgery was expressed as the ratio of the perfusion of the ischemic to non-ischemic limb, thereby normalizing measurements for differences in individual baseline flow.

Representative laser doppler flow images illustrate normal blood flow prior to ligation (FIG. 4A), the loss of blood flow at 1 day after the surgery (FIG. 4B) and the gradual improvement during the observation time after creation of hind limb ischemia and treatment with bone marrow cells, at 12 days (FIG. 4C) and at 27 days after surgery/treatment (FIG. 4D). Beginning at 21 days after surgery, mice injected with unfractionated bone marrow cells (BMC) showed significant flow recovery (expressed as percentage of the average blood flow in the contralateral non-manipulated limb) compared with PBS control treated mice, with further improvement observed by day 27 (41.9%±13.9% and 61.8%±15%, respectively, PBS group (n=13) vs. GFP$^{+/+}$ BMC (n=15), *p<0.05, (FIG. 4E).

Example 5

Angiogenic Cytokines

Blood samples were obtained at the time of euthanasia by cardiac puncture with a 25G needle. The samples were placed at 4° C. overnight followed by centrifugation for 20 min at 2000×g. Serum (150 µl/mouse) samples obtained on the third and fourteenth day post-bone marrow cell treatment were examined using the TranSignal™ Angiogenesis Antibody Array (Panomics, Affymetrix, Santa Clara, Calif.) according to the manufacturer's instruction. Serum samples were incubated with capture antibodies specific to angiogenesis activator or inhibitor proteins. A biotin/streptavidin system and chemiluminescence was used to visualize the antibody-protein complexes on the array. The signals were quantified by densitometry with a Kodak imaging system.

Blood, collected from animals treated with bone marrow cells or PBS after creation of hind limb ischemia, was examined as described for levels of cytokines with known regulatory functions in angiogenesis and immune response. Densitometry was performed for assessment of protein concentrations expressed as ratio of blood in mice injected with bone marrow cells and PBS, respectively (n=3 each). In serum collected 3 days after surgery it was determined that mice injected with bone marrow cells had increased plasma levels of VEGF, FGF2, TGF-α, TGF-β, IL-4 and TNF-α compared to PBS treated mice and with additional differences in cytokine levels observed at 14 days (FIG. 5). No elevation of the cytokines was seen in mock control treated animals.

Thus, it was demonstrated that donor bone marrow cells injected intra-arterially at a dose of 2.5×10$^7$ cells into ischemic limbs of Apo E$^{-/-}$ mice developed into new blood vessels and skeletal muscle cells, associated with increased circulation levels of cytokines; and by 21 days after surgery significantly enhanced blood flow in ischemic hind limbs compared to a control injection of PBS alone.

Having demonstrated that intravascular administration of 2.5×10$^7$ unfractionated GFP$^{+/+}$ bone marrow mononuclear cells was effective in facilitating cell-based revascularization and having determined that donor derived GFP cells accumulated in the vascular and muscular region throughout the ischemic leg, immunostaining on leg cross-sections using a panel of myoendothelial marker revealed that a fraction of GFP cells stained positive for the endothelial progenitor marker CD34 and for the skeletal cell marker M-cadherin.

Example 6

Mouse Hindlimb Ischemia Model and Cell Transplantation

Twelve-month-old C57BL/6J ApoE$^{-/-}$ mice were anesthetized with oxygen enriched with 2% isoflurane. A longitudinal incision was made in the thigh, and the proximal portion of the common left femoral artery and vein were occluded by 2 adjacent ligatures. Unfractionated GFP-positive mouse bone marrow mononuclear cells (2.5×10$^7$ cells in 150 µl of PBS) were delivered via intrafemoral injection. Mice were sacrificed at 7 days for tissue analysis by immunohistochemistry using epifluorescent microscopy. In another group of mice, fractionated and unfractionated bone marrow mononuclear cells (3×10$^5$ cells in 150 µl of PBS) were delivered in the same manner as described above; at 60 days after cell delivery, mice were euthanized by $CO_2$ inhalation and leg samples were taken, fixed in formalin, decalcified, and then transversely cut (6-10 µm) into sections. Each section was examined immunohistochemically with primary antibodies against CD34, von Willebrand factor, CD31, CD105 or M-cadherin, respectively. The sections were incubated with corresponding secondary antibodies, and fluorescent signals were visualized with a Leica DM LB fluorescent microscope (FIGS. 6-8). Significant staining was seen with antibodies that bound CD34 (FIG. 7) and M-cadherin (FIG. 8), Based on these findings both CD34 and M-cadherin-positive cells were identified in freshly isolated bone marrow mononuclear cells through multi-parameter flow analysis (FIG. 9). Mononuclear cells from bone marrow were separated into a single-cell suspension and incubated with antibodies (30 minutes at 4° C.) against hematopoietic, myogenic, endothelial and mesenchymal antigens, such as CD45, Sca-1, CD34, M-cadherin, VEGFR2, Tie2, CXCR4, CD73, CD90, CD105, CD44 and CD166. About 1×10$^6$ cells stained for each antibody were analyzed using a FACS LSRII and Cellquest™ software. Multicolor fluorescence cell sorting was performed on a FACSAir™ dual laser fluorescence cell sorter. In these experiments, all bone marrow mononuclear cell fractions were pooled and used immediately after harvesting for injection into the ischemic limbs. FIG. 9A is a scattergram of these cells with the lower polygon encompasses the live cells present in the bone marrow cell population. Analysis of the live cells in the sample identified cells that were bound by labeled-antibodies selective for CD34 (eBioscience, San Diego, Calif.) and alternatively labeled-antibodies selective for M-cadherin (H-7 1, Santa Cruz Biotechnology, Santa Cruz, Calif.). The scattergram shown in FIG. 9B shows that many of the cells expressed CD34, but few express M-cadherin and even fewer expressed both CD34 and M-cadherin simultaneously. This double positive population of cells is encompassed by the inserted box in FIG. 9B.

Figure 10A:
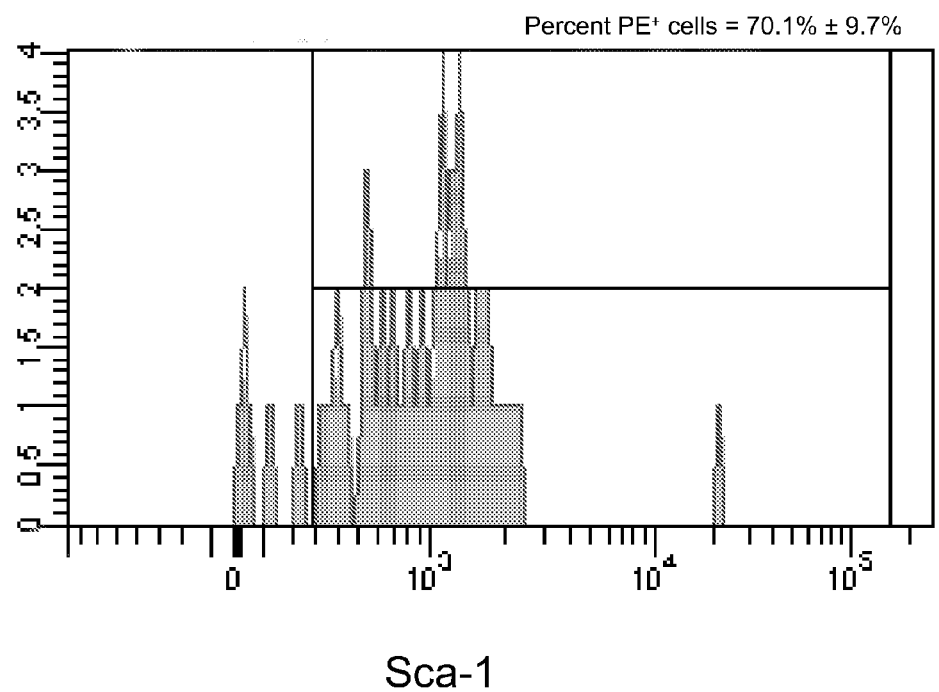
Figure 10B:
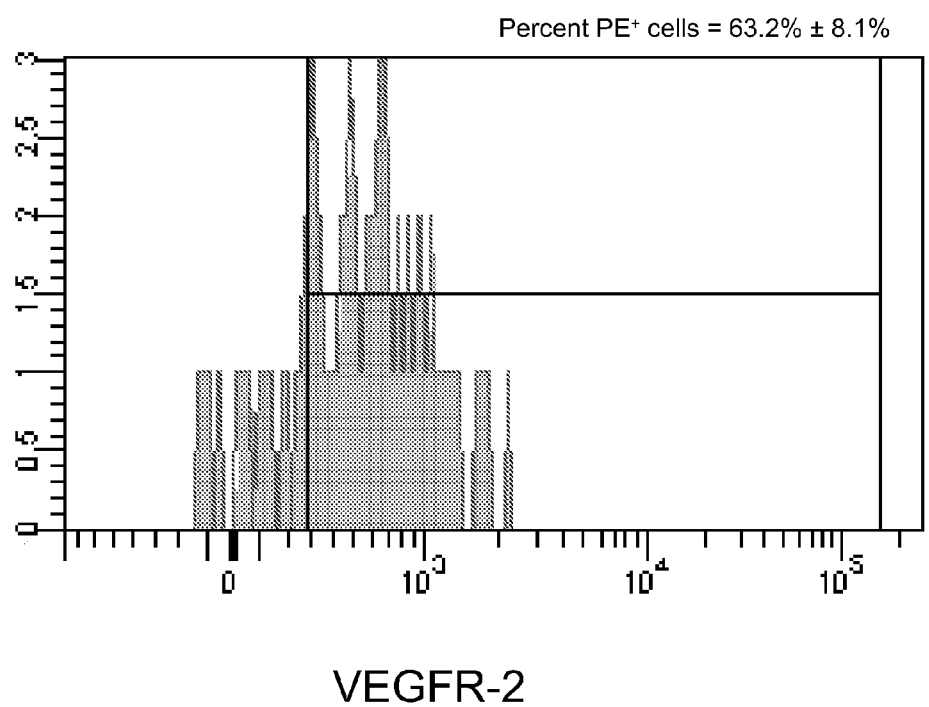
Figure 10C:
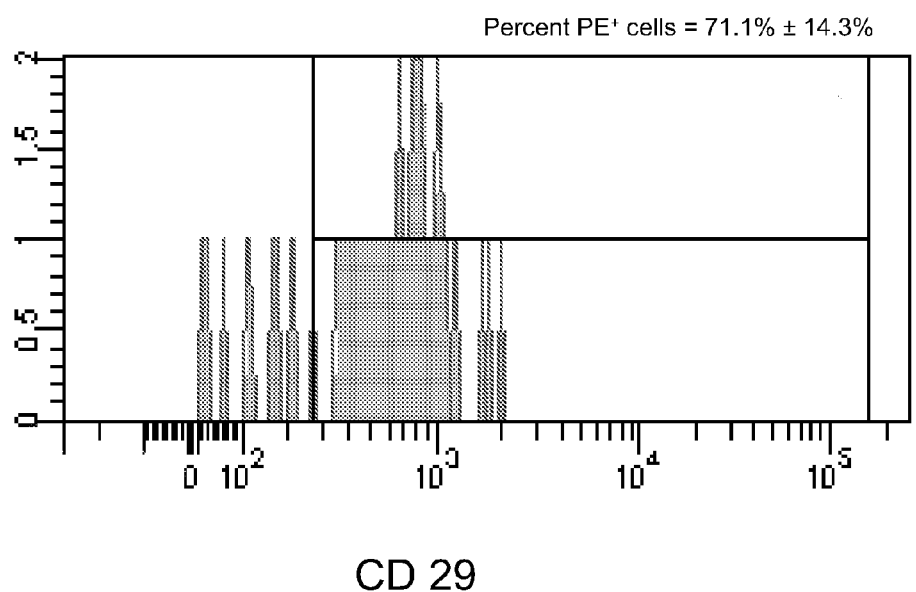
Figure 10D:
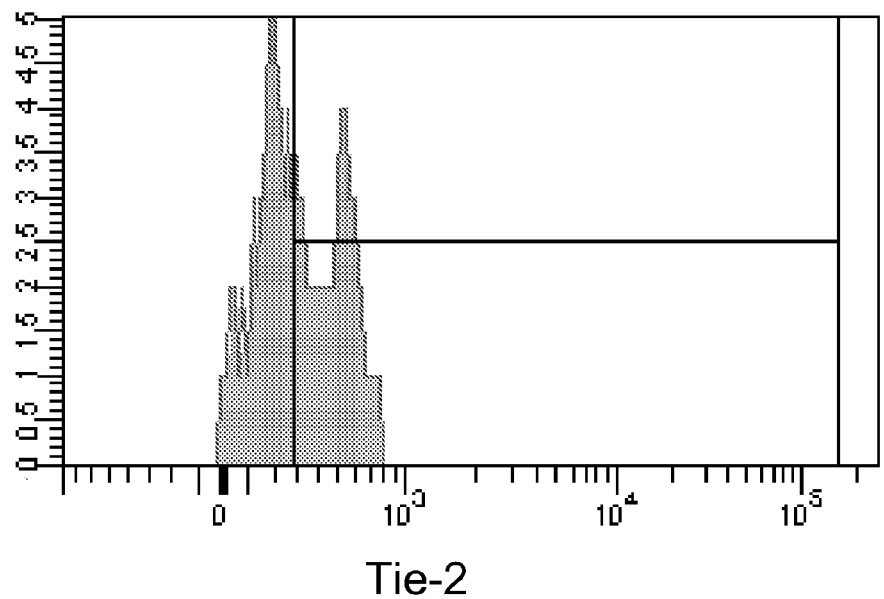
Figure 10E:
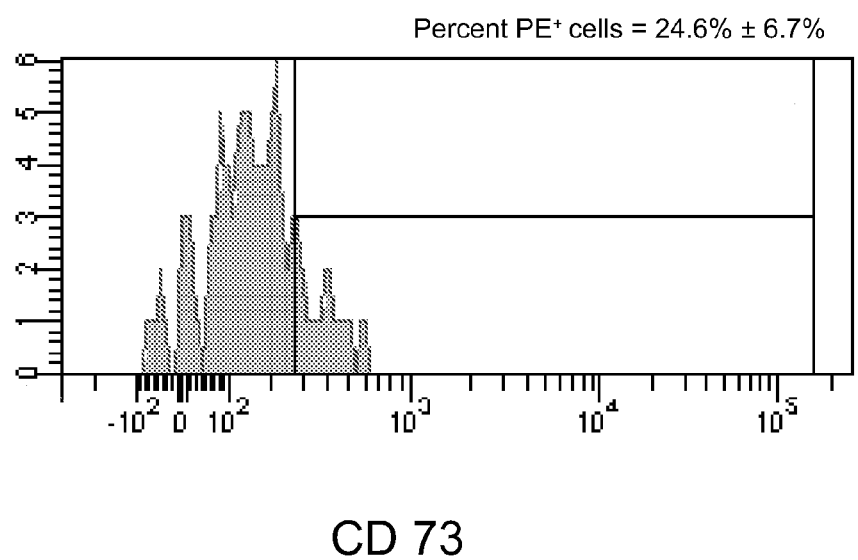
Figure 10F:
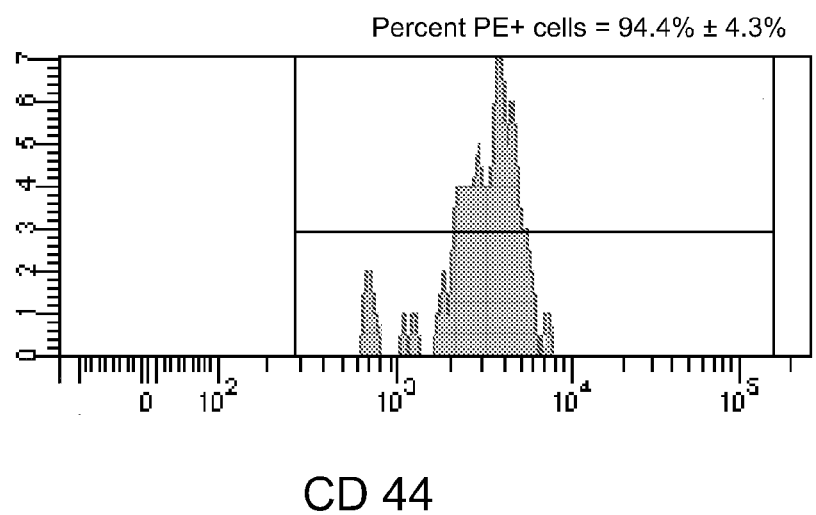
Figure 10G:
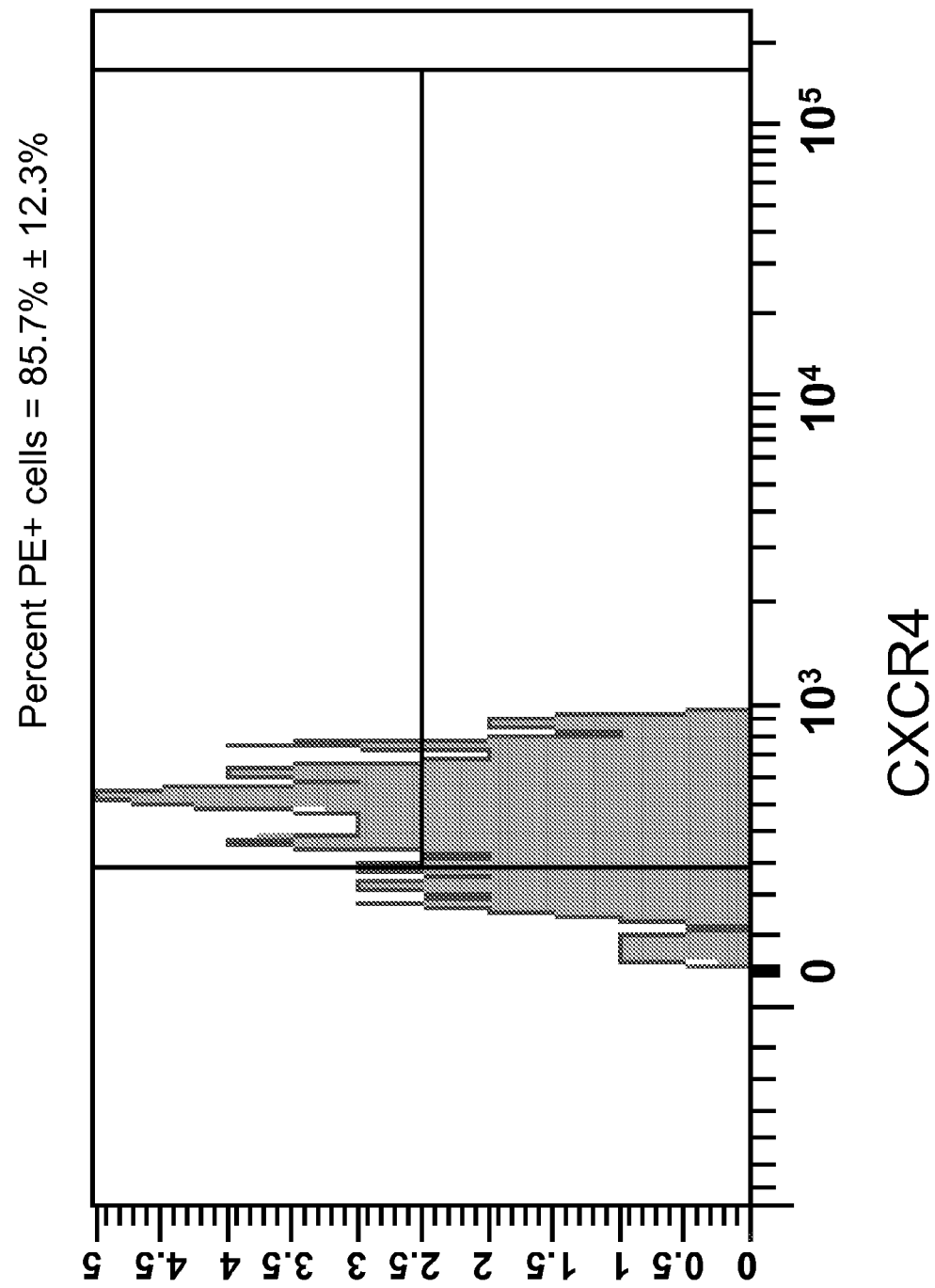

The double-positive CD34$^+$/M-cadherin$^+$ cell population was a rare subset of bone marrow mononuclear cells (0.02%±0.003%: FIG. 9B), which is enriched in Sca-1 (FIG. 10A) and other endothelial progenitor cell markers, including VEGFR$_2$ (FIG. 10B) and Tie-2 (FIG. 10C). In addition, the M-cadherin/CD34-positive population was enriched in mesenchymal cell markers CD29 (FIG. 10C) and CD73 (FIG. 10E) and in the key stem cell mobilization molecules, CD44 (FIG. 10F) and CXCR4 (FIG. 10G).

To demonstrate the efficacy of the fractionated CD34$^+$/M-cadherin$^+$ donor bone marrow mononuclear cells when injected into ischemic hind limbs, unfractionated bone marrow mononuclear cells, fractions enriched in CD34$^+$ or M-cadherin$^+$ alone, and double-positive CD34$^+$/M-cadherin$^+$ cells were obtained by cell sorting from adult C57BL/6J mouse bone marrow and injected intra-arterially into ApoE$^{-/-}$ mice as described previously (n=8 in each group).

Example 7

Laser Doppler Perfusion Imaging

Four bone marrow mononuclear cell populations (CD34$^+$, M-cadherin$^+$, CD34$^+$/M-cadherin$^+$, and unfractionated cells) were isolated from adult C57BL/6J mice and were injected intra-arterially into ischemic hindlimbs of ApoE$^{-/-}$ mice (n=8 in each group, as described previously) at a dose of 3×10$^5$ (in 150 µl of PBS). To assess the revascularization efficacy of fractionated and unfractionated bone marrow mononuclear cells, laser Doppler perfusion imaging was performed at 7-day intervals for up to 60 days after injection of the bone marrow mononuclear cell fractions. Color-coded images were recorded. Individual flow data were computed by calculating the average perfusion of each ischemic limb normalized to blood flow in the contra-lateral (non-manipulated) limb. At the end of the 60-day observation period, the mice were sacrificed and the hindlimbs were harvested for histological analysis. Clinical symptoms of toe necrosis or sudden death were recorded for each treatment group and are presented in the table below.

| Experimental Group | Toe Necrosis | Sudden Death |
|---|---|---|
| CD34$^+$/M-cad$^+$ BMCs (n = 9) | 0 | 0 |
| CD34$^+$/M-cad$^-$ BMCs (n = 11) | 2 (18%) | 1 (9%) |
| CD34$^-$/M-cad$^+$ BMCs (n = 9) | 1 (11%) | 2 (22%) |
| Unselected BMCs (n = 9) | 3 (33%) | 2 (22%) |

FIGS. 11 and 12 summarize laser Doppler imaging results, visually in FIG. 11 wherein color images reveal that blood flow, now represented by light areas in the images, was restored preferentially to the ischemic (IS) limbs of mice treated with CD34$^+$/M-cadherin$^+$ BMCs. FIG. 12 quantitates and illustrates this effect graphically for the 4 treatment groups. FIG. 12 shows that CD34+/M-cadherin+ bone marrow mononuclear cells effectively restore blood flow to the ischemic hindlimb as early as 14 days after cell delivery compared with unfractionated bone marrow mononuclear cells (69.5%±12.4% vs. 45.3%±14.6%, n=8, P<0.01) and that this significant effect in the double-positive versus the unfractionated group persisted up to 60 days. These findings demonstrate that a relatively rare population of adult bone marrow mononuclear cells, i.e., those that are double-positive CD34$^+$/M-cadherin$^+$ cell surface markers, have considerable myoendothelial regenerative potential and a constellation of cell surface markers reminiscent of mesodermal cell lineages. In addition to the potential to develop diverse lineages (including endothelial, smooth muscle, and skeletal muscle cells), these mesodermal-like precursor cells generate a higher intensity and longer duration of revascularization compared with bone marrow mononuclear cells enriched in CD34$^+$ or M-cadherin$^+$ cells alone and that such cells are potentially useful for treating patients suffering from ischemia or ischemia related disorders, and for other diagnostic and therapeutic uses.

Statistical Analysis: To determine statistical difference in blood flow between the PBS and allogenic bone marrow cell treated animals at the different sacrifice time points, ANOVA testing was used, followed by a the Student-Newman-Keul's test to locate comparisons yielding statistical differences at a p level of <0.05.

Another process used to identify and characterize bone marrow mononuclear cells in a group of mice (n=4) is shown in FIG. 13. Bone marrow cells were obtained as described above and by using forward light scattering characteristics, mononuclear cells were identified (scattergram A). The mononuclear cells were then stained with propidium iodide (PI), which intercalates into double-stranded nucleic acids within dead cell, but not living cells, because the intact cell membranes of live cells exclude PI (scattergram B). Thus, the failure to stain with PI identifies a cell as viable. These viable cells were then further analyzed for staining with Alexa Flour® 647 (Invitrogen™ Corporation, Carlsbad, Calif.)-labeled antibodies selective for mouse IgG2a (C), a anti-mouse 2$^{nd}$ antibody control (D), and M-cadherin antibody (E). Viable cells were also stained with FITC-labeled CD34 antibody (F). The mean percent±SEM of viable bone marrow mononuclear cell that stained with mouse IgG2a was 2.50±0.25%. The mean percent of viable bone marrow mononuclear cell that stained with the anti-mouse 2$^{nd}$ antibody control was 1.37±0.39%. The mean percent of viable bone marrow mononuclear cell that stained with M-cadherin antibody was 5.25±0.83%. The mean percent of viable bone marrow mononuclear cell that stained with CD34 antibody was 5.00±0.13%.

FIG. 14 illustrates the results of further immunophenotyping of double positive CD34$^+$/M-cadherin$^+$ cells. The larger scattergrams along the top illustrate the identification and characterization of CD34$^+$ bone marrow mononuclear cells when stained with a second labeled antibody. The smaller interior boxes were drawn to represent double positive cells, i.e. cells that express both CD34 and the ligand recognized by the second antibody. These larger scattergrams illustrate that isolated CD34$^+$ cells did not contain many cells that also stained with labeled mouse IgG2a antibodies (see scattergram A, top left graph, interior box) or that were bound by the anti-mouse 2$^{nd}$ antibody control (see scattergram B, top center graph, interior box: control), but that some did stain with M-cadherin antibodies (see scatter gram C see top right graph, interior box). This final group of cells represents double positive CD34$^+$/M-cadherin$^+$ cells and it is these cells that were further analyzed for additional staining, the result of which appear in the lower group of smaller graphs (D). Immunophenotyping of these double positive CD34$^+$/M-cadherin$^+$ cells using staining with labeled-antibody selective for various cell surface markers is shown in the smaller graphic representations at the bottom of the page (D). Double positive CD34$^+$/M-cadherin$^+$ cells were stained, using labeled-antibody selective for, as shown on the top row, left to right: IgG2a, CD31, CD14, Sca-1, VEGFR2, PDGFα, and CD38; as shown on the middle row, left to right: IgG2b, CXCR4, CD45, CD11b, and CD117; as shown on the bottom row, left to right: IgG1, CD133, Tie2, and CD73.

The resulting graphic representations (D) show that the percentage of double positive CD34$^+$/M-cadherin$^+$ cells that also express: IgG2a was 0%; CD31 was 88%; CD14 was 18%; Sca-1 was 2%; VEGFR2 was 1%; PDGFa was 13%; CD38 was 54%; IgG2b was 0%; CXCR4 was 88%; CD45 was 92%; CD11b was 92%; CD117 was 35%; IgG1 was 0%; CD133 was 48%; Tie2 was 11%; and CD73 was 18%.

In a preferred embodiment of identification of M-cadherin$^+$ and CD34$^+$ subsets included isotype- and fluorochrome-matched control antibodies for CD34 and M-cadherin antibodies that were used in parallel. Flow cytometric analysis of freshly isolated viable BMCs in a scatter plot of BMCs collected from C57BL6/J mice with the P1 gate being used to discriminate doublets (shown in FIG. 15 panel A). Propidium iodium (PI) was used to exclude dead cells ($PI^+$ cells) from further analysis (shown in FIG. 15 panel B). Indirect staining with M-cadherin antibody (BD Biosciences, San Diego, Calif.) revealed a small subpopulation of M-cadherin$^+$ cells (5.30±0.63%, n=4) as compared to those that stained positive with mouse isotype control IgG2a antibodies (1.42±0.29%: eBioscience, San Diego, Calif.). CD34$^+$ BMC population (8.86±0.58%) was detected by an FITC-conjugated anti-CD34 monoclonal antibody (eBioscience, San Diego, Calif.) as shown in FIG. 15 panel C). And a distinct double-positive population of CD34$^+$/M-cadherin$^+$ BMCs (4.28±0.60%, shown if FIG. 16 panel A) was identified by flow cytometry after co-staining BMCs with CD34 and M-cadherin antibodies.

Example 8

Reverse Transcription-Polymerase Chain Reaction (RT-PCR)

This distinct double-positive population of CD34$^+$/M-cad$^+$ BMCs (4.28±0.60%, FIG. 16 panel A) was identified by flow cytometry after co-staining BMCs with CD34 and M-cad antibodies. Additional validation of expression of mouse CD34 and M-cadherin by sorted CD34$^+$/M-cadherin$^+$ BMCs was confirmed by RT-PCR. Total RNA extracted from mouse and human cells was subjected to RT-PCR analysis. RNA isolation was performed according to the protocol provided by the manufacturer (RNeasy Plus Micro Kit, QIAGEN, Germantown, Md.). The purity of RNA was estimated by $A_{260}/A_{280}$ ratio (NanoDrop 1000 Spectrophotometer, Thermo Scientific, Waltham, Mass.). Total RNA from sorted CD34$^-$/M-cadherin$^-$, CD34$^+$/M-cadherin$^-$, CD34$^-$/M-cadherin$^+$, CD34$^+$/M-cadherin$^+$ BMC fractions (C57BL6/J mice), C2C12 myoblast cell line (ATCC), human Rh30 cell line (kindly provided by Dr. P. Houghton, Nationwide Children's Hospital), and human CD34$^+$ bone marrow mononuclear cells (Stem Cell Technologies, Vancouver, Canada) were reverse transcribed with the oligo dT primer and superscript III first strand synthesis system (Invitrogen). PCR was subsequently carried out with mouse or human CD34, M-cadherin and GAPDH (as an internal control) specific primer pairs that were designed using Primer-Blast provided by NCBI and platinum Taq DNA polymerase (Invitrogen). The sizes of PCR products were determined by comparison to a 100 bp DNA ladder (Invitrogen) under UV light after 1-2% agarose gel electrophoresis.

The mouse myoblast cell line, C2C12, known for expressing both CD34 and M-cadherin (Beauchamp, et al., Expression of CD34 and Myf5 defines the majority of quiescent adult skeletal muscle satellite cells. J Cell Biol; 151:1221-1234, 2000) was used as a positive control for RT-PCR (FIG. 16 panel B). In addition, M-cadherin expression by CD34$^+$ human bone marrow mononuclear cells (BMMNCs) was also established using RT-PCR. Using specific human M-cadherin forward and reverse primer pairs, a definite PCR product was identified indicating the existence of M-cadherin transcript in human CD34 BMMNCs (FIG. 16 panel C), thus clearly humans also possess a CD34$^+$/M-cadherin$^+$ cell population. As positive control, a human Rh30 cell line which is known to express M-cadherin was used (Charrasse, et al. Variation in cadherins and catenins expression is linked to both proliferation and transformation of Rhabdomyosarcoma. Oncogene; 23:2420-2430, 2004).

Additional analysis using RT-PCR analysis of human CD34$^+$ peripheral blood cells and human CD34$^+$ cord blood cells revealed the presence of a CD34$^+$/M-cadherin$^+$ cell population in each. Thus in addition to bone marrow, it is possible to utilize human peripheral blood cells and cord blood cells as a source from which to isolate CD34$^+$/M-cadherin$^+$ multipotent mononuclear cells for use in the presently disclosed methods and treatments. The use of peripheral blood cells as a source of autologous CD34$^+$/M-cadherin$^+$ cell for treatment of ischemia is particularly promising, as it is less invasive and safer than harvesting patient bone marrow.

Example 9

Hematopoietic Progenitor Assays

The multipotent clonogenic potential of CD34$^+$/M-cadherin$^+$ BMCs population was examined in colony-forming unit (CFU) assays. CD34$^+$/M-cadherin$^+$ sorted cells were cultured using CollagenCult Medium Kit (StemCell Technologies) per the manufacturer's protocol. The cells were suspended in a medium/collagen solution containing cytokines (10 ng/mL interleukin-3, 10 ng/mL interleukin-6, 50 ng/mL SCF) and $2.2 \times 10^4$ cells were seeded onto tissue culture plates that were incubated under 5% $CO_2$ (37° C., ≥95% humidity). At 21 days, maximum colony size was assessed, and colony-forming cells of the granulocyte/macrophage lineages were identified by morphologic criteria. Collagen gels were dehydrated, and May-Grünwald-Giemsa stains were performed to identify cellular components.

The multipotent clonogenic potential of CD34$^+$/M-cadherin$^+$ BMCs population was examined in colony-forming unit (CFU) assays. FIG. 17 shows the proliferative potential and enriched hematopoietic colony-forming activity (i.e. CFU-G, CFU-M and CFU-GM) of CD34$^+$/M-cadherin$^+$ BMCs grown in collagen-based semi-solid medium supplemented with SCF, IL-3, and IL-6. This finding suggests that this cell type is a hematopoietic progenitor population with multilineage development capability.

Example 10

Conditioned Medium from CD34$^+$/M-cadherin$^+$ Cells Enhances Angiogenesis In Vitro Under Hypoxic Conditions To demonstrate the ability of CD34$^+$/M-cadherin$^+$ cells to drive angiogenesis of endothelial cells in vitro, the well accepted assay known as tube formation was utilized. Mouse BMCs were collected as previously described and sorted for CD34$^+$/M-cadherin$^+$ cells. Approximately $7 \times 10^5$ CD34$^+$/M-cadherin$^+$ cells/well were seeded in a 24-well plate with DMEM (10% FBS, 1% PS) and incubated (37° C., 5% $CO_2$) overnight. DMEM was then removed, and serum-free DMEM was added to the wells and allowed to incubate for an additional 48 hours. CD34$^+$/M-cad$^+$ CM was collected and used to perform endothelial tube formation assays.

A collagen-based reduced growth factor membrane matrix (Geltrex™, Invitrogen) was coated (50 µl/cm$^2$) onto 24-well plates. A thin-gel method was used to ensure endothelial cell differentiation. The plates were then incubated for 30 minutes to allow the gel to solidify. Approximately $3.5 \times 10^5$ SVEC4-10 mouse endothelial cells were resuspended in 200 µl/cm$^2$ of nonsupplemented DMEM (control) or CD34$^+$/M-cadherin$^+$ CM with the addition of 1% FBS final concentration. SVEC4-10 cells were seeded into 24-well plates and placed in an incubator (37° C., 20% $O_2$ 5% $CO_2$) to allow tube formation to develop. Tube formation was documented every hour until a pronounced difference between control and CM was observed. Additionally, this tube formation assay was repeated with SVEC4-10 cells under hypoxic conditions (37° C., 1% $O_2$, 5% $CO_2$). The cells were placed in serum-free media for 24 hours in a hypoxia chamber (Galaxy 14S, New Brunswick, Edison, N.J.). After starvation, cells were prepared as above, and tube formation was carried out in the hypoxia chamber. Tube formation was documented at 4, 6, and 8 hours incubation.

Digital images were taken using an inverted microscope (Olympus IX71, Leeds Instruments, Irving, Tex.) at a 40× magnification for all assay conditions. Assays were performed in triplicate; images were taken in 3 different fields/well, and the analysis was performed by using NIH Image J software. The total tube length (tube defined as structures measuring ≥100 μm formed by the body of 3 cells or more) was measured as μm/mm². Results were standardized as a percent of control (set at 100%). Data were expressed as mean±standard error of mean (SEM). One-way analysis of variance (ANOVA) with the Mann-Whitney post hoc test was used to determine statistical significance within and between groups (GRAPHPAD Prism 5). $P<0.05$ was considered statistically significant.

Nutrient-starved mouse endothelial cells (SVEC4-10) incubated with $CD34^+$/M-cadherin$^+$ CM under normoxic conditions (20% $O_2$, 5% $CO_2$, 37° C.) effectively migrated towards each other, directionally aligned themselves, and formed a complex tubular network as early as 3 hours after seeding on the matrix (as shown in FIG. 18 panel A). The total length of the tubes was increased more than 208% when compared to tubes formed in control endothelial cells incubated with basal DMEM (as shown in FIG. 19, panel A).

To further test the angiogenic effects of $CD34^+$/M-cadherin$^+$ CM during ischemia, we preconditioned nutrient-starved mouse endothelial cells under hypoxic conditions (1% $O_2$, 5% $CO_2$, 37° C.) cells for 24 hours prior to incubating them with $CD34^+$/M-cadherin$^+$ CM. The presence of $CD34^+$/M-cadherin$^+$ CM stimulated the formation of tubular structures, although there were fewer capillary-like networks formed than were seen in endothelial cells treated with $CD34^+$/M-cadherin$^+$ CM under normoxic conditions (as shown in FIG. 18 panel B). In contrast, the control medium-treated endothelial cells did not form typical capillary structures or networks under the same experimental conditions (as shown in FIG. 18 panel B). Total tube length of endothelial cells stimulated by $CD34^+$/M-cadherin$^+$ CM, under hypoxic conditions, was increased by 466% (4 hr), 693% (6 hr) and 1095% (8 hr), respectively, as compared with control treatment (as shown in FIG. 19 panel B). These findings are consistent with the in vivo results shown elsewhere in the disclosure in which significant restoration of blood flow perfusion and greater arteriogenesis in the ischemic legs of ApoE$^{-/-}$ mice.

Example 11

CD34$^+$/M-cadherin$^+$ BMCs Secrete a Unique Array of Cytokines and Growth Factors Conditioned medium obtained from cultures of unselected BMCs or CD34$^+$/M-cadherin$^+$ BMCs was collected 48 hrs after cells were seeded into culture dishes. The expression level of cytokines in CM was analyzed by using a dot-blot cytokine array. Approximately 2×10$^5$ unselected BMCs or CD34$^+$/M-cadherin$^+$ BMCs were seeded in separate 10 mm culture dishes in Iscove's Modified Dulbecco's Medium (IMDM, Invitrogen) supplemented with 10% fetal bovine serum (FBS) and 1% penicillin-streptomycin for 24 hrs, and then changed to serum-free IMDM for an additional 24 hrs. Conditioned medium (CM) was collected, filtered to eliminate cell debris, and frozen at −80° C.

A dot-blot cytokine array kit was used according to the manufacturer's instructions (RayBiotech, Inc., Norcross, Ga.). In short, after a brief membrane blocking step, CM was added, and the membrane was incubated overnight at 4° C. After a series of washes, the membrane was incubated with biotinylated anticytokine antibodies and horseradish peroxidase conjugated-streptavidin-followed by signal detection using ECL-Hyperfilm. Cytokine expression levels were measured using ImageJ software and analyzed with RayBio Analysis Tool S.09 (RayBiotech, Inc.).

The in-vitro release of cytokines and growth factors by CD34$^+$/M-cadherin$^+$ BMCs and unselected BMCs was assessed. We quantified the secretion of multiple pro-angiogenic and proliferative factors by using a cytokine antibody array (results are shown in FIG. 20). Of the 20 cytokines measured, basic fibroblast growth factor (bFGF), epidermal growth factor (EGF), and hepatocyte growth factor (HGF) were significantly increased in the CM of CD34$^+$/M-cadherin$^+$ cells as compared to CM from unselected BMCs. Additionally, CD34$^+$/M-cadherin$^+$ cells released significantly higher levels of Flt-3 ligand (FLT3-L) and vascular endothelial growth factor receptor 3 (VEGFR$_3$). Both of these growth factors have been shown to be involved in survival, proliferation, and differentiation of early progenitor cells and endothelial vessels. Furthermore, the CM of CD34$^+$/M-cad$^+$ cells had significantly higher levels of resistin, a cardioprotective protein that has been shown to be expressed in bone marrow cells and adipose tissue. Levels of CXCL-10 (CRG-2), which has been shown to recruit human mesenchymal stem cells (MSCs), were significantly higher in CD34$^+$/M-cadherin$^+$ CM than in CM of unselected BMCs. Together, these results provide clear evidence that CD34$^+$/M-cadherin$^+$ cells secrete a variety of pro-survival and proangiogenic cytokines that can contribute to the formation of a functional vascular network.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. For example, although the foregoing description focuses primarily on multi-potent progenitor cells obtained from autologous or heterologous bone marrow and co-expressing both CD34 and M-cadherin (CD34$^+$/M-cadherin$^+$) cell markers, it should also be understood that similar progenitor cells may also be obtained by expanding bone marrow cells in vitro, or from stem cells, embryonic endothelial cells or muscle cells, embryonic stem cell lines and hematopoietic stem cells, or any other suitable source, and used in the same manner as bone marrow derived cells. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of enhancing blood flow in a tissue of a mammal, comprising:
   administering to said tissue a therapeutically effective amount of a composition comprising isolated multipotent mammalian mononuclear cells, wherein said cells are derived from bone marrow, and at least 95% of said cells express both CD34 and M-cadherin cell surface markers, and wherein said tissue is atherosclerotic.

2. The method of claim 1, wherein at least 99% of the isolated multipotent mammalian mononuclear cells express both CD34 and M-cadherin cell surface markers.

3. The method of claim 1, wherein less than 10% of the isolated multipotent mammalian mononuclear cells expressing both CD34 and M-cadherin cell surface markers also express Pax3 or Pax7.

4. The method of claim 1, wherein the isolated multipotent mammalian mononuclear cells are autologous.

5. The method of claim 1, wherein said administering comprises delivering a dose of said composition directly to an ischemic tissue site or an adjacent site in said mammal, wherein said dose comprises $10^2$-$10^{10}$ cells bearing both CD34 and M-cadherin cell surface markers.

6. The method of claim 1, wherein said administered multipotent mammalian mononuclear cells induce functional new blood vessels in said tissue.

7. The method of claim 1, wherein said mammal has at least one symptom of ischemia in said tissue, and said administered multipotent mammalian mononuclear cells improve said at least one symptom.

8. The method of claim 1, wherein said tissue comprises myocardium.

9. The method of claim 1, wherein said tissue is vascular tissue in a limb of the mammal.

10. The method of claim 1, further comprising administering an angiogenic cytokine to said tissue.

11. The method of claim 1, wherein the isolated multipotent mammalian mononuclear cells are heterologous to said mammal.

* * * * *